United States Patent
Richter et al.

(10) Patent No.: US 10,815,224 B2
(45) Date of Patent: Oct. 27, 2020

(54) MONOCYCLIC HETEROARYL SUBSTITUTED COMPOUNDS

(71) Applicant: Bristol-Myers Squibb Company, Princeton, NJ (US)

(72) Inventors: Jeremy M. Richter, Yardley, PA (US); Xiaojun Zhang, Furlong, PA (US); Eldon Scott Priestley, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/317,232

(22) PCT Filed: Jul. 13, 2017

(86) PCT No.: PCT/US2017/041873
§ 371 (c)(1),
(2) Date: Jan. 11, 2019

(87) PCT Pub. No.: WO2018/013772
PCT Pub. Date: Jan. 18, 2018

(65) Prior Publication Data
US 2019/0248771 A1  Aug. 15, 2019

Related U.S. Application Data

(60) Provisional application No. 62/362,081, filed on Jul. 14, 2016.

(51) Int. Cl.
C07D 413/10 (2006.01)
C07D 417/14 (2006.01)
(Continued)

(52) U.S. Cl.
CPC .............. *C07D 413/10* (2013.01); *A61P 7/02* (2018.01); *C07D 403/04* (2013.01);
(Continued)

(58) Field of Classification Search
CPC .. C07D 413/10; C07D 403/10; C07D 417/10; C07D 417/14; A61P 7/02
(Continued)

(56) References Cited

U.S. PATENT DOCUMENTS 4,567,269 A * 1/1986 Gerster ................ C07D 215/38
546/167
4,797,148 A * 1/1989 Hagen .................... A01N 43/42
504/247
(Continued)

FOREIGN PATENT DOCUMENTS

EP         0224823 A2    6/1987
WO    WO200031049 A1   6/2000
(Continued)

OTHER PUBLICATIONS

Sheaffer; PLoS ONE, Jun. 9, 2016, 11, e0155909, 18 pages. DOI:10.1371/journal.pone.0155909 (Year: 2016).*
(Continued)

*Primary Examiner* — Daniel R Carcanague
(74) *Attorney, Agent, or Firm* — Mary K. VanAtten

(57) ABSTRACT

Disclosed are compounds of Formulas (I), (II), (III), (IV), (V), (VI), (VII), or (VIII): (I) (II) (III) (IV) (V) (VI) (VII) (VIII) or a stereoisomer, tautomer, pharmaceutically acceptable salt, solvate or prodrug thereof, wherein $R_3$ is a monocyclic heteroaryl group substituted with zero to 3 $R_{3a}$; and $R_1$, $R_2$, $R_{3a}$, $R_4$, and n are defined herein. Also disclosed are methods of using such compounds as PAR4 inhibitors, and pharmaceutical compositions comprising such compounds. These compounds are useful in inhibiting or preventing platelet aggregation, and are useful for the treatment of a thromboembolic disorder or the primary prophylaxis of a thromboembolic disorder.

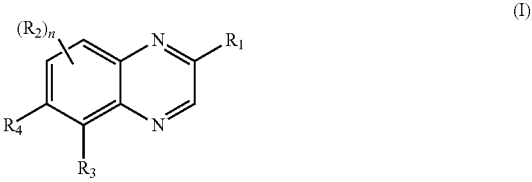

(I)

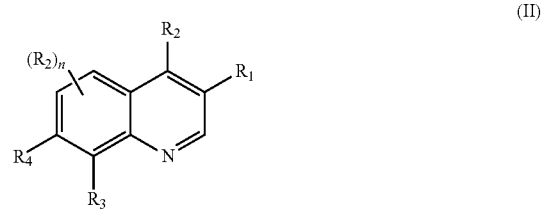

(II)

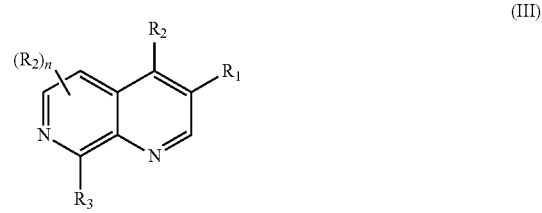

(III)

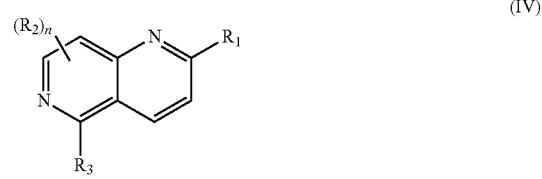

(IV)

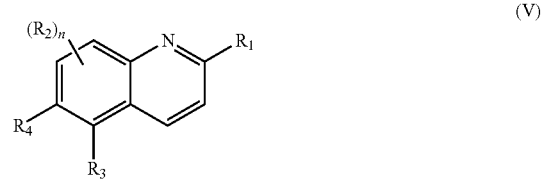

(V)

(Continued)

-continued

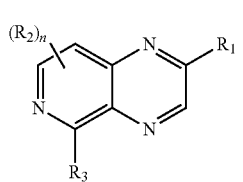
(VI)

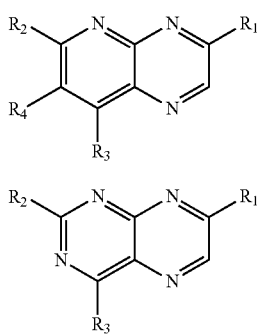

(VII)

(VIII)

10 Claims, No Drawings

(51) Int. Cl.
| | |
|---|---|
| *C07D 403/04* | (2006.01) |
| *C07D 413/04* | (2006.01) |
| *C07D 471/04* | (2006.01) |
| *C07D 417/04* | (2006.01) |
| *A61P 7/02* | (2006.01) |
| *C07D 403/10* | (2006.01) |
| *C07D 417/10* | (2006.01) |

(52) U.S. Cl.
CPC ......... *C07D 403/10* (2013.01); *C07D 413/04* (2013.01); *C07D 417/04* (2013.01); *C07D 417/10* (2013.01); *C07D 417/14* (2013.01); *C07D 471/04* (2013.01)

(58) Field of Classification Search
USPC ........................................................ 544/284
See application file for complete search history.

(56) References Cited

U.S. PATENT DOCUMENTS

| | | | |
|---|---|---|---|
| 5,110,347 A | 5/1992 | Selby | |
| 5,633,218 A * | 5/1997 | Spedding | A01N 43/30 504/228 |
| 9,518,064 B2 | 12/2016 | *Martel et al. | |
| 9,688,695 B2 | 6/2017 | *Banville et al. | |
| 9,862,730 B2 | 1/2018 | *Lawrence et al. | |
| 10,047,103 B2 | 8/2018 | *Banville et al. | |
| 10,214,544 B2 | 2/2019 | *Banville | |
| 2014/0213580 A1 | 7/2014 | Cao et al. | |
| 2015/0329538 A1* | 11/2015 | Cee | C07D 471/04 514/210.21 |
| 2018/0214445 A1 | 8/2018 | Zhang et al. | |
| 2018/0305376 A1 | 10/2018 | Banville et al. | |
| 2019/0292176 A1* | 9/2019 | Zhang | C07D 417/04 |
| 2019/0300520 A1* | 10/2019 | Fu | C07D 513/04 |
| 2019/0315774 A1* | 10/2019 | Zhang | A61P 7/02 |

FOREIGN PATENT DOCUMENTS

| | | |
|---|---|---|
| WO | WO2004043929 A1 | 5/2004 |
| WO | WO2007149395 A2 | 12/2007 |
| WO | WO2008141065 A1 | 11/2008 |
| WO | WO2012054874 A1 | 4/2012 |
| WO | WO2013130660 A1 | 9/2013 |
| WO | WO2013163241 A1 | 10/2013 |
| WO | WO2013163279 A1 | 10/2013 |
| WO | WO2013163244 A8 | 4/2014 |
| WO | WO2015077550 A1 | 5/2015 |
| WO | WO2016134450 A1 | 9/2016 |
| WO | WO2017019828 A1 | 2/2017 |
| WO | WO-2018013770 A1 * | 1/2018 ........... C07D 417/04 |
| WO | WO2018013774 A1 | 1/2018 |
| WO | WO2018013776 A1 | 1/2018 |
| WO | WO2018/013770 | 1/2019 |

OTHER PUBLICATIONS

French; British Journal of Pharmacology 2016, 173, 2952-2965. DOI:10.1111/bph.13455 (Year: 2016).*
U.S. Appl. No. 16/317,248, Zhang et al., filed Jan. 11, 2019.
U.S. Appl. No. 16/317,258, Zhang et al., filed Jan. 11, 2019.
Alabaster, et al., "2(1H)-Quinolinones with Cardiac Stimulant Activity. 1, Synthesis and Biological Activities of (Six-Membered Heteroaryl)-Substituted Derivatives", Journal of Medicinal Chemistry, vol. 31(10), pp. 2048-2056 (1988).
Kuang, et al., "Discovery of a highly potent series of oxazole-based phosphodiesterase 4 inhibitors", Bioorganic & Medicinal Chemistry Letters, vol. 17, pp. 5150-5154 (2007).
Kuang, et al., "Discovery of oxazole-based PDE4 inhibitors with picomolar potency", Bioorganic and Medicinal Chemistry Letters, vol. 22, pp. 2594-2597 (2012).
Suzuki et al., "Novel Synthesis of 7-Fluoro-8-(trifluoromethyl)-1H-1,6-naphthyridin-4-one Derivatives: Intermolecular Cyclization of an N-Silyl-1-azaallyl Anion with Perfluoroalkene and Subsequent Intramolecular Skeletal Transformation of the Resulting Pentasubstituted Pyridines", Journal of Organic Chemistry, vol. 72(15), pp. 5878-5881 (2007).

* cited by examiner

MONOCYCLIC HETEROARYL SUBSTITUTED COMPOUNDS

CROSS REFERENCE TO RELATED APPLICATIONS

This application is a 371 application of PCT/US2017/041873 filed Jul. 13, 2017 which is entitled to priority pursuant to 35 U.S.C. § 119(e) to U.S. provisional patent application No. 62/362,081, filed Jul. 14, 2016, which is incorporated herein in its entirety.

FIELD OF THE INVENTION

The present invention generally relates to monocyclic heteroaryl substituted compounds useful as inhibitors of platelet aggregation. Provided herein are monocyclic heteroaryl substituted compounds, compositions comprising such compounds, and methods of their use. The invention further pertains to pharmaceutical compositions containing at least one compound according to the invention that are useful in preventing or treating thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., *Nature*, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., *N. Eng. J. Med.*, 366(1):20-33 (2012). Thus, there remains a need to discover new antiplatelet agents with increased efficacy and reduced bleeding side effects.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", *J. Med. Chem.*, 44(22):3746-3749 (2001) discloses in the abstract that the compound

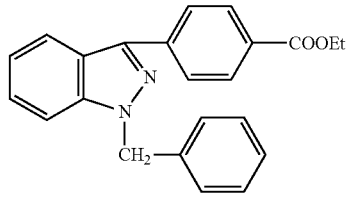

58

"was found to be a selective and potent inhibitor or protease-activated receptor type 4 (PAR4)-dependent platelet activation." Compound 58 is also referred to as YD-3 in Wu, C-C. et al., "Selective Inhibition of Protease-activated Receptor 4-dependent Platelet Activation by YD-3", *Thromb. Haemost.*, 87:1026-1033 (2002). Also, see Chen, H. S. et al., "Synthesis and antiplatelet activity of ethyl 4-(1-benzyl-1H-indazol-3-yl)benzoate (YD-3) derivatives", *Bioorg. Med. Chem.*, 16:1262-1278 (2008).

EP1166785 A1 and EP0667345 disclose various pyrazole derivatives which are useful as inhibitors of platelet aggregation.

The PCT publications WO2013/163279, WO2013/163244, and WO2013/163241 disclose various PAR4 antagonists which are useful as inhibitors of platelet aggregation.

There still remains a need for compounds useful as inhibitors of platelet aggregation.

Applicants have found potent compounds that have activity as PAR4 inhibitors. These compounds are provided to be useful as pharmaceuticals with desirable potency, stability, bioavailability, therapeutic index, and toxicity values that are important to their drugability.

SUMMARY OF THE INVENTION

It has been found that monocyclic heteroaryl substituted compounds in accordance with the present invention are PAR4 antagonists which inhibit platelet aggregation in gamma-thrombin induced platelet aggregation assays.

Accordingly, the present invention provides monocyclic heteroaryl substituted compounds that are PAR4 antagonists and are useful as selective inhibitors of platelet aggregation, including stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment or prophylaxis of a thromboembolic disorder.

Other features and advantages of the invention will be apparent from the following detailed description and claims.

DETAILED DESCRIPTION

The first aspect of the present invention provides at least one compound of Formulas (I), (II), (III), (IV), (V), (VI), (VII), or (VIII):

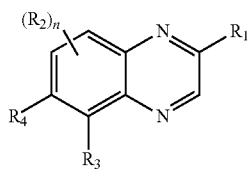

(I)

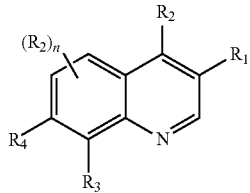

(II)

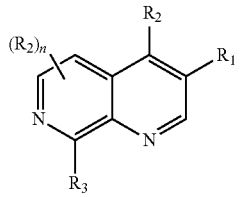

(III)

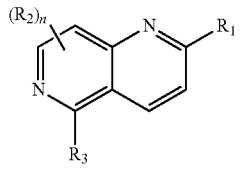

(IV)

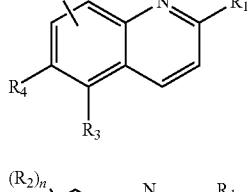

(V)

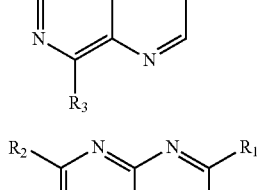

(VI)

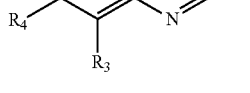

(VII)

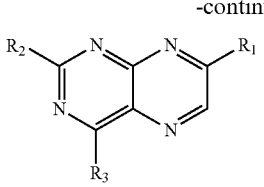

(VIII)

or a salt thereof; wherein:

$R_1$ is F, Cl, —OH, $C_{1-4}$ alkyl, $C_{1-4}$ fluoroalkyl, $C_{2-4}$ alkenyl, $C_{2-4}$ alkynyl, $C_{3-7}$ cycloalkyl, $C_{3-7}$ fluorocycloalkyl, $C_{1-3}$ alkoxy, $C_{1-3}$ fluoroalkoxy, $C_{2-4}$ hydroxyalkoxy, $C_{3-6}$ cycloalkoxy, ($C_{1-3}$ alkoxy)-($C_{1-3}$ alkylene), ($C_{1-3}$ alkoxy)-($C_{1-3}$ fluoroalkylene), ($C_{1-3}$ deuteroalkoxy)-($C_{1-3}$ deuteroalkylene), ($C_{1-3}$ fluoroalkoxy)-($C_{1-3}$ alkylene), ($C_{1-3}$ fluoroalkoxy)-($C_{1-3}$ fluoroalkylene), —$(CH_2)_{1-3}$O(phenyl), —$(CH_2)_{1-3}NR_aR_a$, —C(O)O($C_{1-6}$ alkyl), —C(O)$NR_aR_a$, —C(O)$NR_bR_b$, —$NH_2$, —NH($C_{1-6}$ alkyl), —N($C_{1-6}$ alkyl)$_2$, azetidin-1-yl, pyrrolidin-1-yl, furanyl, pyranyl, piperidin-1-yl, morpholin-4-yl, piperazin-1-yl, —$S(O)_2$($C_{1-3}$ alkyl), —$S(O)_2NR_aR_a$, or $C_{1-3}$ alkylthio;

$R_2$, at each occurrence, is independently H, F, Cl, Br, —OH, —CN, $C_{1-4}$ alkyl, $C_{1-4}$ fluoroalkyl, $C_{1-4}$ hydroxyalkyl, $C_{1-4}$ aminoalkyl, $C_{2-4}$ alkenyl, $C_{2-4}$ alkynyl, $C_{3-7}$ cycloalkyl, $C_{3-7}$ fluorocycloalkyl, $C_{1-6}$ alkoxy, $C_{1-3}$ fluoroalkoxy, $C_{1-3}$ alkylthio, ($C_{1-3}$ alkoxy)-($C_{1-3}$ alkylene), ($C_{1-3}$ fluoroalkoxy)-($C_{1-3}$ alkylene), —C(O)$NH_2$, —C(O)NH ($C_{1-6}$ alkyl), —C(O)N($C_{1-6}$ alkyl)$_2$, —C(O)$NR_bR_b$, —CH(OH)($C_{3-6}$ cycloalkyl), —CH(OH)(phenyl), —$S(O)_2$($C_{1-3}$ alkyl), —$S(O)_2NR_aR_a$, or a cyclic group selected from phenyl, 5- to 6-membered heteroaryl, and 5- to 7-membered heterocycle, wherein said cyclic group is substituted with zero to 5 substituents independently selected from F, Cl, $C_{1-3}$ alkoxy, and —CN;

$R_3$ is a monocyclic group selected from thiophenyl, pyrazolyl, thiazolyl, isothiazolyl, thiadiazolyl, pyridinyl, imidazolyl, furyl, oxazolyl, pyrrolyl, pyrimidinyl, pyridazinyl, pyrazinyl, tetrazolyl, triazolyl, oxadiazolyl, isoxazolyl, isothiadiazolyl, and isoxadiazolyl, each monocyclic group substituted with zero to 3 $R_{3a}$;

$R_{3a}$, at each occurrence, is independently H, F, Cl, —CN, —OH, $C_{1-6}$ alkyl, $C_{2-6}$ alkenyl, $C_{1-6}$ fluoroalkyl, $C_{1-6}$ hydroxyalkyl, $C_{1-6}$ alkoxy, $C_{1-3}$ fluoroalkoxy, $C_{1-6}$ alkylthio, —$(CH_2)_m$-$C_{3-7}$ cycloalkyl, —$(CH_2)_m$-aryl, —$(CH_2)_m$-heteroaryl, —$(CH_2)_m$-heterocyclyl, —$(CH_2)_{1-3}$ $NR_aR_a$, —$(CH_2)_{1-3}$ NHS(O)$_2$(aryl), ($C_{1-3}$ alkoxy)-($C_{1-6}$ alkoxy), —C(O)OH, —C(O)O($C_{1-6}$ alkyl), —C(O)$NR_aR_a$, —C(O) $NR_bR_b$, —$S(O)_2NR_aR_a$, —$S(O)_2NR_bR_b$, —C(O)($C_{1-4}$ alkyl), —C(O)aryl, —C(O)heteroaryl, —C(O)($C_{3-7}$ cycloalkyl), —$S(O)_2$($C_{1-4}$ alkyl), —$S(O)_2$aryl, —$S(O)_2$heteroaryl, —$S(O)_2$ ($C_{3-7}$ cycloalkyl), —$NR_aR_a$, or —$NR_bR_b$, wherein each of said cycloalkyl, heterocyclyl, aryl, and heteroaryl is substituted with zero to 5 substituents independently selected from F, Cl, —OH, oxo, —CN, $C_{1-3}$ alkyl, $C_{1-3}$ fluoroalkyl, $C_{1-4}$ hydroxyalkyl, $C_{1-3}$ alkoxy, $C_{1-3}$ fluoroalkoxy, $C_{1-6}$ alkylthio, —$NH_2$, —NHC(O)($C_{1-6}$ alkyl), $C_{1-3}$ hydroxyalkoxy, COOH, —C(O)O($C_{1-6}$ alkyl) —C(O) $NR_aR_a$, —C(O)$NR_bR_b$, —$S(O)_2NR_aR_a$, —$S(O)_2NR_bR_b$, —C(O)($C_{1-4}$ alkyl), —C(O)aryl, —C(O)heteroaryl, —C(O) ($C_{3-7}$ cycloalkyl), —$S(O)_2$($C_{1-4}$ alkyl), —$S(O)_2$aryl, —$S(O)_2$heteroaryl, —$S(O)_2$ ($C_{3-7}$ cycloalkyl), —$NR_aR_a$, or —$NR_bR_b$;

$R_4$ is H, F, Cl, or —$CH_3$;

$R_a$, at each occurrence, is independently H, $C_{1-3}$ alkyl, $C_{1-3}$ fluoroalkyl, $C_{3-6}$ cycloalkyl, aryl, or heteroaryl:

two $R_b$ along with the nitrogen atom to which they are attached form a 4- to 7-membered heterocyclo ring:

m, at each occurrence, is zero, 1, or 2; and n, at each occurrence, is zero, 1, or 2.

One embodiment provides a compound of Formula (I) having the structure of Formula (Ia):

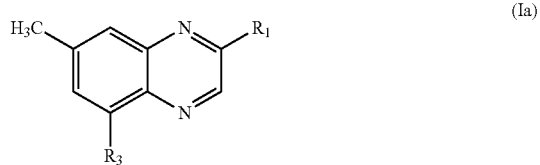

or a salt thereof.

One embodiment provides at least one compound of Formulas (I), (II), (III), (IV), (V), (VI), or (VIII) or a salt thereof, wherein:

$R_1$ is methyl, —OCH$_3$, —OCHF$_2$, —OCH$_2$CH$_3$, or —CH$_2$OCH$_3$; $R_2$ is $C_{1-3}$ alkyl; $R_3$ is a monocyclic group selected from thiophenyl, isoxazolyl, pyrazolyl, thiazolyl, isothiazolyl, thiadiazolyl, pyridinyl, imidazolyl, furyl, oxazolyl, pyrrolyl, pyrimidinyl, tetrazolyl, triazolyl, oxadiazolyl, isoxazolyl, isothiadiazolyl, and isoxadiazolyl, each monocyclic group substituted with zero to 3 $R_{3a}$; $R_{3a}$, at each occurrence, is independently H, —CH$_3$, —C(CH$_3$)$_3$, —CF$_3$, —CH$_2$OH, —CH=CH$_2$, cyclopropyl, cyclohexyl, —CH$_2$(phenyl), —C(O)(hydroxymethyl piperidinyl). —C(O)(cyclohexyl), —C(O)NHCH$_2$CH$_3$, —C(O)NH (methoxy phenyl), piperidinyl, pyrazolyl, methyl pyrazolyl, indole, phenyl substituted with zero to 3 substituents independently selected from F, Cl, —OH, —CH$_3$, —CHF$_2$, —CF$_3$, and —OCF$_3$; or pyridinyl substituted with zero to 2 substituents independently selected from —OH, —CH$_3$, and —OCH$_3$; and n is zero, 1, or 2.

One embodiment provides a compound of Formulas (I), (II), (III), (IV), (V), (VI), (VII), or (VIII) or a salt thereof, wherein: $R_1$ is —OCH$_3$, —OCHF$_2$, or —CH$_2$OCH$_3$; $R_2$ is —CH$_3$; $R_3$ is a monocyclic group selected from thiophenyl, isoxazolyl, pyrazolyl, thiazolyl, isothiazolyl, thiadiazolyl, pyridinyl, imidazolyl, furyl, oxazolyl, pyrrolyl, pyrimidinyl, tetrazolyl, triazolyl, oxadiazolyl, isoxazolyl, isothiadiazolyl, and isoxadiazolyl, each monocyclic group substituted with zero to 3 $R_{3a}$; $R_{3a}$, at each occurrence, is independently H, —CH$_3$, —C(CH$_3$)$_3$, —CF$_3$, —CH$_2$OH, —CH=CH$_2$, cyclopropyl, cyclohexyl, —CH$_2$(phenyl), —C(O)(hydroxymethyl piperidinyl), —C(O)(cyclohexyl), —C(O)NHCH$_2$CH$_3$, —C(O)NH(methoxy phenyl), piperidinyl, pyrazolyl, methyl pyrazolyl, indole, phenyl substituted with zero to 3 substituents independently selected from F, Cl, —OH, —CH$_3$, —CHF$_2$, —CF$_3$, and —OCF$_3$; or pyridinyl substituted with zero to 2 substituents independently selected from —OH, —CH$_3$, and —OCH$_3$; and n is zero, 1, or 2. Included in this embodiment is a compound of Formula (Ia) or a salt thereof.

One embodiment provides a compound of Formula (I) or a salt thereof, wherein: $R_1$ is —OCHF$_2$ or —CH$_2$OCH$_3$; $R_2$ is —CH$_3$; $R_{3a}$, at each occurrence, is independently H, —CH$_3$, —C(CH$_3$)$_3$, —CF$_3$, —CH$_2$OH, —CH=CH$_2$, cyclopropyl, cyclohexyl, —CH$_2$(phenyl), —C(O)(hydroxymethyl piperidinyl), —C(O)(cyclohexyl). —C(O)NHCH$_2$CH$_3$, —C(O)NH(methoxy phenyl), piperidinyl, pyrazolyl, methyl pyrazolyl, indole, phenyl substituted with zero to 3 substituents independently selected from F, C$_1$, —OH, —CH$_3$, —CHF$_2$, —CF$_3$, and —OCF$_3$; or pyridinyl substituted with zero to 2 substituents independently selected from —OH, —CH$_3$, and —OCH$_3$; and n is zero, 1, or 2. Included in this embodiment is a compound of Formula (Ia) or a salt thereof.

One embodiment provides a compound of Formula (I) or a salt thereof, wherein: $R_1$ is —OCHF$_2$ or —CH$_2$OCH$_3$; $R_2$ is —CH$_3$; $R_3$ is thiazolyl substituted with zero to 2 $R_{3a}$; and $R_{3a}$, at each occurrence, is independently H, —CH$_3$, —C(CH$_3$)$_3$, —CF$_3$, —CH$_2$OH, —CH=CH$_2$, cyclopropyl, cyclohexyl, —CH$_2$(phenyl), —C(O)(hydroxymethyl piperidinyl), —C(O)(cyclohexyl), —C(O)NHCH$_2$CH$_3$, —C(O)NH(methoxy phenyl), piperidinyl, pyrazolyl, methyl pyrazolyl, indole, phenyl substituted with zero to 3 substituents independently selected from F, Cl, —OH, —CH$_3$, —CHF$_2$, —CF$_3$, and —OCF$_3$; or pyridinyl substituted with zero to 2 substituents independently selected from —OH, —CH$_3$, and —OCH$_3$. Included in this embodiment is a compound of Formula (Ia) or a salt thereof.

One embodiment provides a compound of Formula (I) or a salt thereof, wherein: $R_1$ is —OCHF$_2$; $R_2$ is —CH$_3$; $R_3$ is isoxazolyl, pyrazolyl, thiazolyl, isothiazolyl, or thiadiazolyl, each substituted with zero to 2 $R_{3a}$; and $R_{3a}$, at each occurrence, is independently —CH$_3$, —C(CH$_3$)$_3$, —CF$_3$, —CH$_2$OH, —CH=CH$_2$, cyclopropyl, cyclohexyl, —CH$_2$(phenyl), —C(O)(hydroxymethyl piperidinyl), —C(O)(cyclohexyl), —C(O)NHCH$_2$CH$_3$, —C(O)NH(methoxy phenyl), piperidinyl, pyrazolyl, methyl pyrazolyl, indole, phenyl substituted with zero to 3 substituents independently selected from F, Cl, —OH, —CH$_3$, —CHF$_2$, —CF$_3$, and —OCF$_3$; or pyridinyl substituted with zero to 2 substituents independently selected from —OH, —CH$_3$, and —OCH$_3$. Included in this embodiment is a compound of Formula (Ia) or a salt thereof.

One embodiment provides a compound of Formula (I) or a salt thereof, wherein: $R_1$ is —OCH$_3$, —OCHF$_2$, or —CH$_2$OCH$_3$; $R_2$ is H, F, Cl, Br, —OH, —CN, $C_{1-3}$ alkyl, $C_{1-3}$ fluoroalkyl, $C_{1-3}$ hydroxyalkyl, or $C_{1-3}$ aminoalkyl; $R_3$ is a monocyclic group selected from thiophenyl, isoxazolyl, pyrazolyl, thiazolyl, isothiazolyl, thiadiazolyl, pyridinyl, imidazolyl, furyl, oxazolyl, pyrrolyl, pyrimidinyl, tetrazolyl, triazolyl, oxadiazolyl, isoxazolyl, isothiadiazolyl, and isoxadiazolyl, each monocyclic group substituted with zero to 3 $R_{3a}$; $R_{3a}$, at each occurrence, is independently H, —CH$_3$, —C(CH$_3$)$_3$, —CF$_3$, —CH$_2$OH, —CH=CH$_2$, cyclopropyl, cyclohexyl, —CH$_2$(phenyl), —C(O)(hydroxymethyl piperidinyl). —C(O)(cyclohexyl), —C(O)NHCH$_2$CH$_3$, —C(O)NH(methoxy phenyl), piperidinyl, pyrazolyl, methyl pyrazolyl, indole, phenyl substituted with zero to 3 substituents independently selected from F, Cl, —OH, —CH$_3$, —CHF$_2$, —CF$_3$, and —OCF$_3$; or pyridinyl substituted with zero to 2 substituents independently selected from —OH, —CH$_3$, and —OCH$_3$; and n is zero, 1, or 2.

One embodiment provides a compound of Formulas (I), (II), (III), (IV), (V), (VI), (VII), or (VIII) or a salt thereof, wherein $R_3$ is:

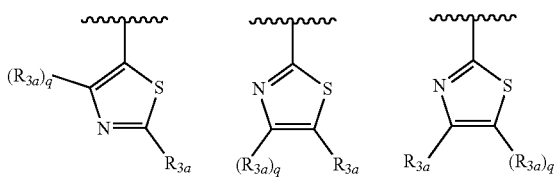

-continued

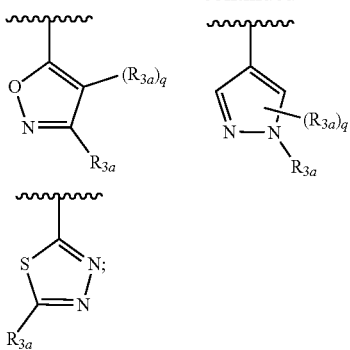

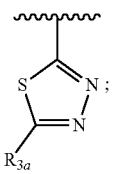 or q is zero or 1; and $R_1$, $R_2$, $R_4$, $R_{3a}$, and n are defined in the first aspect. Included in this embodiment are compounds of Formula (Ia).

One embodiment provides a compound of Formula (I) or a salt thereof, wherein: or a salt thereof, wherein $R_3$ is:

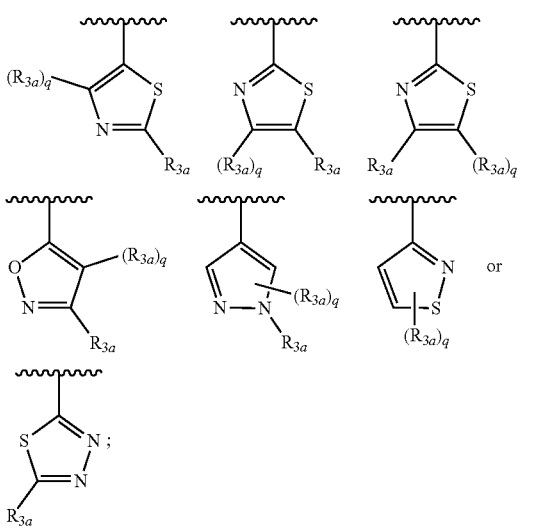

$R_4$ is H; n is zero or 1; q is zero or 1; and $R_1$, $R_2$, and $R_{3a}$ are defined in the first aspect.

One embodiment provides a compound of Formula (I) or a salt thereof, wherein: or a salt thereof, wherein $R_1$ is —OCH$_3$, —OCHF$_2$, or —CH$_2$OCH$_3$; $R_3$ is:

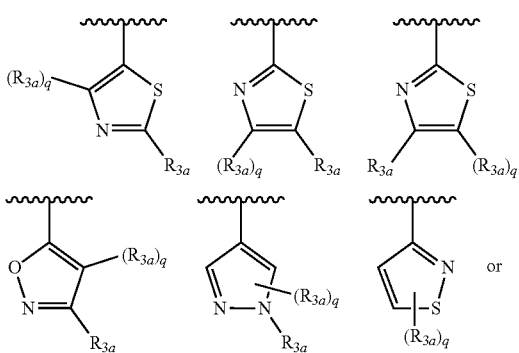

-continued

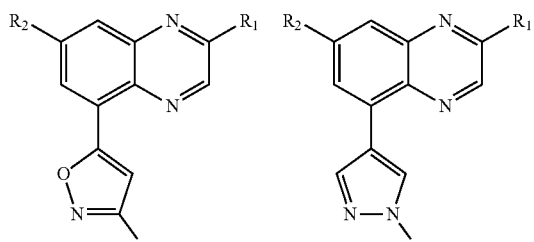

$R_4$ is H; n is zero or 1; q is zero or 1; and $R_1$, $R_2$, and $R_{3a}$ are defined in the first aspect.

One embodiment provides a compound of Formula (Ia) selected from:

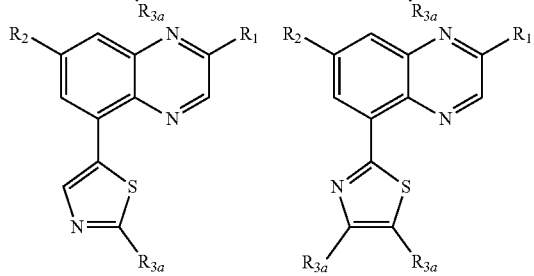

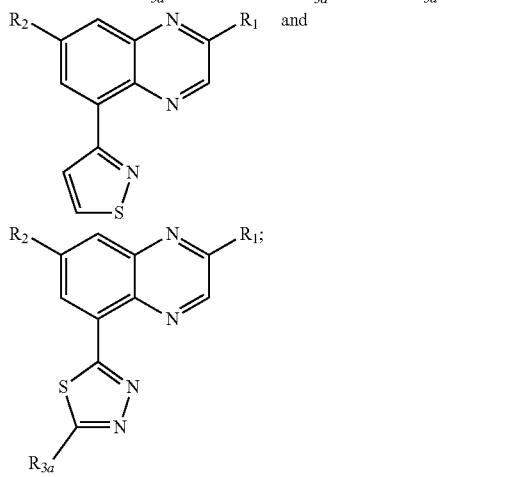

wherein: $R_1$ is —OCH$_3$, —OCHF$_2$, or —CH$_2$OCH$_3$; $R_2$ is —CH$_3$; and $R_{3a}$, at each occurrence, is independently H, —CH$_3$, —C(CH$_3$)$_3$. —CF$_3$, —CH$_2$OH, —CH=CH$_2$, cyclopropyl, cyclohexyl, —CH$_2$(phenyl), —C(O)(hydroxymethyl piperidinyl), —C(O)(cyclohexyl). —C(O)NHCH$_2$CH$_3$, —C(O)NH(methoxy phenyl), piperidinyl, pyrazolyl, methyl pyrazolyl, indole, phenyl substituted with zero to 3 substituents independently selected from H, F, Cl, —OH, —CH$_3$, —CHF$_2$, —CF$_3$, and —OCF$_3$; or pyridinyl substituted with zero to 2 substituents independently selected from —OH, —CH$_3$, and —OCH$_3$. Included in this embodiment are compounds in which $R_1$ is —OCHF$_2$. Included in this embodiment is a compound of Formula (Ia) or a salt thereof.

One embodiment provides a compound of Formula (Ia) selected from:

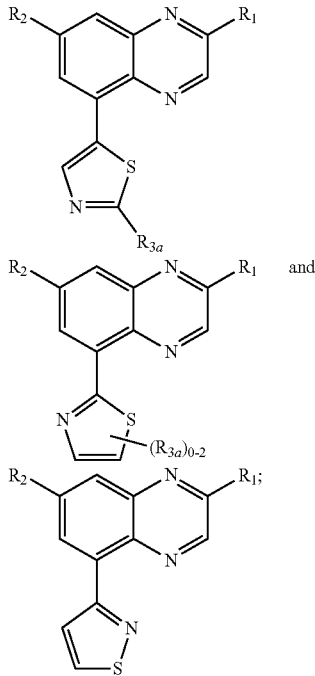

wherein: $R_1$ is —OCH$_3$, —OCHF$_2$, or —CH$_2$OCH$_3$; $R_2$ is —CH$_3$; and $R_{3a}$, at each occurrence, is independently H, —CH$_3$, —C(CH$_3$)$_3$, —CF$_3$, —CH$_2$OH, —CH═CH$_2$, cyclopropyl, cyclohexyl, —CH$_2$(phenyl), —C(O)(hydroxymethyl piperidinyl), —C(O)(cyclohexyl), —C(O)NHCH$_2$CH$_3$, —C(O)NH(methoxy phenyl), piperidinyl, pyrazolyl, methyl pyrazolyl, indole, phenyl substituted with zero to 3 substituents independently selected from F, Cl, —OH, —CH$_3$, —CHF$_2$, —CF$_3$, and —OCF$_3$; or pyridinyl substituted with zero to 2 substituents independently selected from —OH, —CH$_3$, and —OCH$_3$.

One embodiment provides a compound of Formula (Ia) selected from:

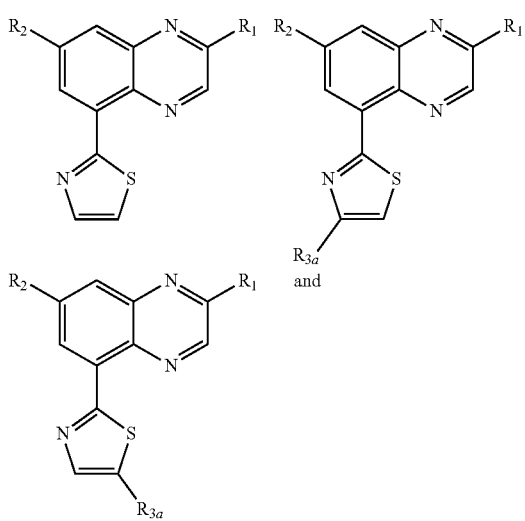

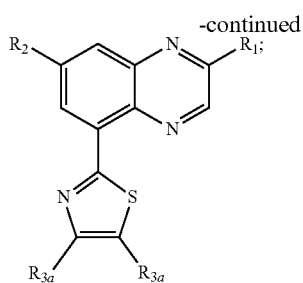

wherein: $R_1$ is —OCH$_3$, —OCHF$_2$, or —CH$_2$OCH$_3$; $R_2$ is —CH$_3$; and $R_{3a}$, at each occurrence, is independently H, —CH$_3$, —C(CH$_3$)$_3$, —CF$_3$, —CH$_2$OH, —CH═CH$_2$, cyclopropyl, cyclohexyl, —CH$_2$(phenyl), —C(O)(hydroxymethyl piperidinyl), —C(O)(cyclohexyl), —C(O)NHCH$_2$CH$_3$, —C(O)NH(methoxy phenyl), piperidinyl, pyrazolyl, methyl pyrazolyl, indole, phenyl substituted with zero to 3 substituents independently selected from F, Cl, —OH, —CH$_3$, —CHF$_2$, —CF$_3$, and —OCF$_3$; or pyridinyl substituted with zero to 2 substituents independently selected from —OH, —CH$_3$, and —OCH$_3$.

One embodiment provides a compound selected from 5-(2-methoxy-7-methylquinoxalin-5-yl)-3-phenylisoxazole (1); 2-(difluoromethoxy)-7-methyl-5-(1-phenyl-1H-pyrazol-4-yl)quinoxaline (2); 5-(2-(difluoromethoxy)-7-methylquinoxalin-5-yl)-2-phenylthiazole (3); 2-(2-(difluoromethoxy)-7-methylquinoxalin-5-yl)-5-methylthiazole (4); 3-(2-(difluoromethoxy)-7-methylquinoxalin-5-yl)isothiazole (5); 3-(2-(2-(difluoromethoxy)-7-methylquinoxalin-5-yl)-4-methylthiazol-5-yl)phenol (6); 5-benzyl-2-(2-(difluoromethoxy)-7-methylquinoxalin-5-yl)thiazole (7); 2-(2-(difluoromethoxy)-7-methylquinoxalin-5-yl)-4-vinylthiazole (8); 2-(2-(difluoromethoxy)-7-methylquinoxalin-5-yl)-4-methyl-5-(1H-pyrazol-5-yl)thiazole (9); 4-cyclopropyl-2-(2-(difluoromethoxy)-7-methylquinoxalin-5 yl)thiazole (10); 2-(2-(2-(difluoromethoxy)-7-methylquinoxalin-5 yl) 4-methylthiazol-5-yl)-4-fluorophenol (11); 2-(2-(2-(difluoromethoxy)-7-methylquinoxalin-5-yl)-4-methylthiazol-5-yl)-3-fluorophenol (12); 2-(2-(difluoromethoxy)-7-methylquinoxalin-5-yl)-5-yl)piperidin-1-yl)thiazole (13); 5-(2-(2-(difluoromethoxy)-7-methylquinoxalin-5-yl)thiazol-5-yl)pyridin-3-ol (14); 2-(2-(2-(difluoromethoxy)-7-methylquinoxain-5-yl)-4-methylthiazol-5-yl)phenol (15); 2-(2-(difluoromethoxy)-7-methylquinoxalin-5-yl)-5-(2-(trifluoromethyl)phenyl)thiazole (16): 5-cyclohexyl-2-2(difluoromethoxy)-7-methylquinoxalin-5 yl)thiazole (17); 2-(2-(methoxymethyl)-7-methylquinoxalin-5-yl)-5-phenylthiazole (18); 2-(2-(2-(difluoromethoxy)-7-methylquinoxalin-5-yl)thiazol-5-yl)-6-fluorophenol (19); 2-(2-(2-(difluoromethoxy)-7-methylquinoxalin-5-yl)thiazol-5-yl)-4-methylphenol (20); 2-(2-(2-(difluoromethoxy)-7-methylquinoxalin-5-yl)thiazol-5-yl)-4-fluorophenol (21); 2-(2-(2-(difluoromethoxy)-7-methylquinoxalin-5-yl)thiazol-5-yl)-4-chlorophenol (22); 2-(2-(2-(difluoromethoxy)-7-methylquinoxalin-S y)thiazol-5 yl)-6-chlorophenol (23); 2-(2-(2-(difluoromethoxy)-7-methylquinoxalin-5 yl)thiazol-5 yl)-3-fluorophenol (24); 3-(2-(2-(difluoromethoxy)-7-methylquinoxalin-5-yl)thiazol-5-yl)-4-fluorophenol (25); 3-(2-(2-(difluoromethoxy)-7-methylquinoxalin-5-yl)thiazol-5-yl)-5-fluorophenol (26); 3-(2-(2-(difluoromethoxy)-7-methylquinoxalin-5-yl)thiazol-5 v)-4-(trifluoromethoxy)phenol (27): 2-(2-(difluoromethoxy)-7-methylquinoxalin-5-yl)-5-phenylthiazole (28); 2-(2-(difluoromethoxy)-7- methylquinoxalin-5-yl)-5-(pyri din-3-yl)thiazole (29); 2-(2-(2-(difluoromethoxy)-7-methylquinoxalin-5-yl)thiazol-5-yl)phenol (30); N-ethyl-2-(2-methoxy-7-methylquinoxalin-5 yl)thiazole-5-carboxamide (31); 2-(2-(difluoromethoxy)-7-methylquinoxalin-5-yl)-N-(4-methoxyphenyl)thiazole-4-carboxamide (32); (2-(2-(difluoromethoxy)-7-methylquinoxalin-5-yl)thiazol-4-yl) (4-(hydroxymethyl)piperidin-1-yl)methanone (33): 2-(2-(difluoromethoxy)-7-methylquinoxalin-5-yl)thiazole (34); 2-(2-(difluoromethoxy)-7-methylquinoxalin-5-yl)-5-phenyl-1,3,4-thiadiazole (35); 2-(2-(difluoromethoxy)-7-methylquinoxalin-5-yl)-4-methylthiazole (36); 2-(2-(difluoromethoxy)-7-methylquinoxalin-5-yl)-5-(1H-indol-7-yl)thiazole (37); 2-(2-(difluoromethoxy)-7-methylquinoxalin-5-yl)-5-(1H-indol-4-yl)thiazole (38); (2-(2-(difluoromethoxy)-7-methylquinoxalin-5-yl)thiazol-5-yl)methanol (39); 2-(2-(difluoromethoxy)-7-methylquinoxalin-5-yl)-5-(1H-pyrazol-5-yl)thiazole (40); 4-(tert-butyl)-2-(2-(difluoromethoxy)-7-methylquinoxalin-5-yl)thiazole (41); 2-(2-(difluoromethoxy)-7-methylquinoxalin-5-yl)-5-(1H-indol-6-yl)thiazole (42); 2-(2-(difluoromethoxy)-7-methylquinoxalin-5-yl)-5-(pyridin-4-yl)thiazole (43); 2-(2-(difluoromethoxy)-7-methylquinoxalin-5-yl)-5-(pyridin-2-yl)thiazole (44); 5-(2-(difluoromethyl)phenyl)-2-(2-methoxy-7-methylquinoxalin-5-yl)thiazole (45); 2,3-difluoro-5-(2-(2-methoxy-7-methylquinoxalin-5-yl)thiazol-5-yl)phenol (46); cyclohexyl(2-(2-methoxy-7-methylquinoxalin-5-yl)-4-(trifluoromethyl)thiazol-5-yl)methanone (47); 2-(2-methoxymethyl)-7-methylquinoxalin-5-yl)-5-(1H-pyrazol-5-yl)thiazole (48); 3-(2-(2-(methoxymethyl)-7-methylquinoxalin-5-yl)thiazol-5-yl)phenol (49); 4-fluoro-2-(2-(2-(methoxymethyl)-7-methylquinoxalin-5-yl)thiazol-5-yl)phenol (50); 3-(2-(2-(difluoromethoxy)-7-methylquinoxalin-5-yl)thiazol-5-yl)phenol (51); 2-(2-methoxy-7-methylquinoxalin-5-yl)-5-(5-methoxypyridin-2-yl)thiazole (52); and 2-(2-(methoxymethyl)-7-methylquinoxalin-5-yl)-5-(5-methoxypyridin-2-yl)thiazole (53).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless the) are otherwise limited in specific instances) either individually or as part of a larger group.

Throughout the specification, groups and substituents thereof may be chosen by one skilled in the field to provide stable moieties and compounds.

In accordance with a convention used in the art.

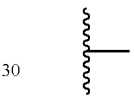

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —NH$_2$.
The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "aminoalkyl" as used herein is intended to include both branched and straight-chain saturated aliphatic hydrocarbon groups substituted with one or more amino groups. For example, "$C_{1-4}$ aminoalkyl" is intended to include $C_1$, $C_2$, $C_3$, and $C_4$ alkyl groups substituted with one or more amino groups. Representative examples of aminoalkyl groups include, but are not limited to, —CH$_2$NH$_2$, —CH$_2$CH$_2$NH$_2$, and —CH$_2$CH(NH$_2$)CH$_3$.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and C$_{1-4}$ hydroxyalkyl.

The term "hydroxy-deuteroalkyl" includes both branched and straight-chain saturated alkyl groups substituted with one or more hydroxyl groups and one or more deuterium atoms. Representative examples of hydroxy-deuteroalkyl groups include, but are not limited to, —CD$_2$OH and —CH(CD$_3$)$_2$OH.

The term "hydroxy-fluoroalkyl" includes both branched and straight-chain saturated alkyl groups substituted with one or more hydroxyl groups and one or more fluorine atoms. Representative examples of hydroxy-fluoroalkyl groups include, but are not limited to, —CF$_2$OH and —CF$_2$CH$_2$OH.

As used herein, "alkylene" refers to a bivalent alkyl radical having the general formula —(CH$_2$)$_n$—, where n is 1 to 10. Non-limiting examples include methylene, dimethylene, trimethylene, tetramethylene, pentamethylene, and hexamethylene. For example, "C$_{1-6}$ alkylene" denotes straight and branched chain alkylene groups with one to six carbon atoms. Further, for example, "C$_{0-4}$ alkylene" denotes a bond and straight and branched chain alkylene groups with one to four carbon atoms.

As used herein, "deuteroalkylene" refers to an alkylene group in which one or more hydrogen atoms have been replaced with deuterium atoms. For example, "C$_{1-6}$ deuteroalkylene" denotes straight and branched chain deuteroalkylene groups with one to six carbon atoms.

As used herein, "fluoroalkylene" refers to an alkylene group substituted with one or more fluorine atoms. For example, "C$_{1-6}$ fluoroalkylene" denotes straight and branched chain fluoroalkylene groups with one to six carbon atoms.

The term "alkenyl" refers to a straight or branched chain hydrocarbon radical containing from 2 to 12 carbon atoms and at least one carbon-carbon double bond. Exemplary such groups include ethenyl or allyl. For example, "C$_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "C$_{2-6}$ alkynyl" denotes straight and branched chain alkynyl groups with two to six carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "C$_{3-6}$ cycloalkyl" denotes cycloalkyl groups with three to six carbon atoms.

The term "fluorocycloalkyl" refers to a cycloalkyl group in which one or more hydrogen atoms are replaced by fluoro group(s).

The term "cycloalkylalkylene" refers to a cycloalkyl group attached through an alkylene group to the patent molecular moiety. For example, "(C$_{3-6}$ cycloalkyl)-(C$_{0-2}$ alkylene)" denotes a C$_{3-6}$ cycloalkyl group attached through a bond or a C$_{1-2}$ alkylene to the parent molecular moiety.

The term "alkoxy," as used herein, refers to an alkyl group attached to the parent molecular moiety through an oxygen atom, for example, methoxy group (—OCH$_3$). For example, "C$_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "C$_{1-4}$ fluoroalkoxy" is intended to include C$_1$, C$_2$, C$_3$, and C$_4$ fluoroalkoxy groups.

The term "hydroxyalkoxy" represent a hydroxyalkyl group as defined above attached through an oxygen linkage (—O—). For example, "C$_{1-4}$ hydroxyalkoxy" is intended to include C$_1$, C$_2$, C$_3$, and C$_4$ hydroxyalkoxy groups.

The term "cycloalkoxy," as used herein, refers to a cycloalkyl group attached to the parent molecular moiety through an oxygen atom, for example, cyclopropoxy group (—O(cyclopropyl)).

The term "alkoxyalkoxy" as used herein, refers to an alkoxy group attached through an alkoxy group to the patent molecular moiety. For example, "(C$_{1-3}$ alkoxy)-(C$_{1-6}$ alkoxy)" denotes a C$_{1-3}$ alkoxy group attached through a C$_{1-6}$ alkoxy group to the parent molecular moiety.

The term "alkoxyalkylene" as used herein, refers to an alkoxy group attached through an alkylene group to the patent molecular moiety. For example, "(C$_{1-3}$ alkoxy)-(C$_{1-3}$ alkylene)" denotes a C$_{1-3}$ alkoxy group attached through a C$_{1-3}$ alkylene to the parent molecular moiety.

The term "fluoroalkoxyalkylene" as used herein, refers to a fluoroalkoxy group attached through an alkylene group. For example, "(C$_{1-2}$ fluoroalkoxy)-(C$_{1-2}$ alkylene)" denotes a C$_{1-2}$ fluoroalkoxy group attached through a C$_{1-2}$ alkylene to the parent molecular moiety.

The term "alkoxy-fluoroalkylene" as used herein, refers to an alkoxy group attached through a fluoroalkylene group to the patent molecular moiety. For example, "(C$_{1-3}$ alkoxy)-(C$_{1-3}$ fluoroalkylene)" denotes a C$_{1-3}$ alkoxy group attached through a C$_{1-3}$ fluoroalkylene to the parent molecular moiety.

The term "deuteroalkoxy-deuteroalkylene" as used herein, refers to a deuteroalkoxy group attached through a deuteroalkylene group to the patent molecular moiety. For example, "(C$_{1-3}$ deuteroalkoxy)-(C$_{1-3}$ deuteroalkylene)" denotes a C$_{1-3}$ deuteroalkoxy group attached through a C$_{1-3}$ deuteroalkylene to the parent molecular moiety.

The term "alkylthio," as used herein, refers to an alkyl group attached to the parent molecular moiety through a sulfur atom, for example, methylthio group (—SCH$_3$). For example, "C$_{1-3}$ alkylthio" denotes alkylthio groups with one to three carbon atoms.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "benzyl," as used herein, refers to a methyl group in which one of the hydrogen atoms is replaced by a phenyl group.

The term "aryloxy," as used herein, refers to an aryl group attached through an oxygen group.

The term "phenoxy," as used herein, refers to a phenyl group attached through an oxygen group (—O-phenyl).

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolidinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridinyl, furopyridinyl, dihydroisoindolyl, and tetrahydroquinolinyl.

The term "heteroaryloxy," as used herein, refers to a heteroaryl group attached through an oxygen group to the patent molecular moiety.

The term "arylalkylene" refers to an aryl group attached through an alkylene group to the patent molecular moiety. For example, "aryl($C_{1-2}$ alkylene)" refers to an aryl group attached through a $C_{1-2}$ alkylene to the parent molecular moiety.

The term "heteroarylalkylene" refers to a heteroaryl group attached through an alkylene group to the patent molecular moiety. For example, "heteroaryl($C_{1-2}$ alkylene)" refers to a heteroaryl group attached through a $C_{1-2}$ alkylene to the parent molecular moiety.

The term "aryloxyalkylene" refers to an aryloxy group attached through an alkylene group to the patent molecular moiety. For example, "aryloxy-($C_{1-2}$ alkylene)" refers to an aryloxy group attached through a $C_{1-2}$ alkylene to the parent molecular moiety.

The term "heteroaryloxyalkylene" refers to a heteroaryloxy group attached through an alkylene group to the patent molecular moiety. For example, "heteroaryloxy-($C_{1-2}$ alkylene)" refers to a heteroaryloxy group attached through a $C_{1-2}$ alkylene to the parent molecular moiety.

The compounds of the present invention can be provided as amorphous solids or crystalline solids. Lyophilization can be employed to provide the compounds as amorphous solids.

It should further be understood that solvates (e.g., hydrates) of the Compounds of Formulas (I), (II), (III), (IV), (V), (VI), (VII), or (VIII) are also within the scope of the present invention. The term "solvate" means a physical association of a compound of Formulas (I), (II), (III), (IV), (V), (VI), (VII), or (VIII) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

In addition, compounds of Formulas (I), (II), (III), (IV), (V), (VI), (VII), or (VIII), subsequent to their preparation, can be isolated and purified to obtain a composition containing an amount by weight equal to or greater than 99% of a compound of Formulas (I), (II), (III), (IV), (V), (VI), (VII), or (VIII) ("substantially pure"), which is then used or formulated as described herein. Such "substantially pure" compounds of Formulas (I), (II), (III), (IV), (V), (VI), (VII), or (VIII) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Biology

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, P-selectin or CD40L release, or thrombosis and hemostasis models). In certain embodiments, platelet activation is measured by changes in the platelet cytoplasm, by changes of the platelet membrane, by changes in the levels of analytes released by platelets, by the changes in the morphology of the platelet, by the ability of platelets to form thrombi or platelet aggregates in flowing or stirred whole blood, by the ability of platelets to adhere to a static surface which is derivatized with relevant ligands (e.g., von Willebrand Factor, collagen, fibrinogen, other extracellular matrix proteins, synthetic fragments of any of the proteins, or any combination thereof), by changes in the shape of the platelets, or any combinations thereof. In one embodiment, platelet activation is measured by changes in the levels of one or more analytes released by platelets. For example, the one or more analytes released by platelets can be P-selectin (CD62p), CD63, ATP, or any combination thereof. In a particular embodiment, platelet activation is measured by the level of binding of fibrinogen or GPIIbIIIa antibodies to platelets. In other embodiments, platelet activation is measured by the degree of phosphorylation of vasodilator-stimulated phosphoprotein (VASP) upon platelet activation. In yet other embodiments, platelet activation is measured by the level of platelet-leukocyte aggregates. In certain embodiments, platelet activation is measured by proteomics profiling. The term "PAR4 antagonist" also includes a compound that inhibits both PAR1 and PAR4.

Preferably, compounds of the invention have $IC_{50}$ values in the PAR4 FLIPR Assay (described hereinafter) of about 10 µM, preferably 1 µM or less, more preferably 100 nM or less, and even more preferably 10 nM or less.

In some embodiments, the present invention provides a pharmaceutical composition, which includes a pharmaceutically acceptable carrier and a therapeutically effective amount of a compound of Formulas (I), (II), (III), (IV), (V), (VI), (VII), or (VIII), preferably, a compound selected from one of the examples, more preferably, Examples 1 to 53, or stereoisomers, tautomers, pharmaceutically acceptable salts, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-platelet agent or a combination thereof. Preferably, the anti-platelet agent (s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are a FXa inhibitor, a thrombin inhibitor, or a FXIa inhibitor. Preferably, the FXa inhibitors are apixaban, rivaroxaban, or edoxaban. Preferably, the thrombin inhibitor is dabigatran.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets: (h) improved therapeutic index with less propensity for bleeding; and (h) factors that improve manufacturing costs or feasibility.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition," as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy*, 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The pharmaceutical composition is administered using methods known in the art. Preferably, the compound is administered orally, rectally, nasally, by inhalation, topically or parenterally, e.g., subcutaneously, intraperitoneally, intramuscularly, and intravenously. The compound is optionally formulated as a component of a cocktail of therapeutic drugs to treat a thromboembolic disorder. In one embodiment, the pharmaceutical composition is administered orally.

The therapeutic compounds described herein are formulated into pharmaceutical compositions utilizing conventional methods. For example, a PAR4 antagonist is formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art. The compositions of the invention are also useful for parenteral administration, such as intravenous, subcutaneous, intramuscular, and intraperitoneal. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

The activity of the PAR4 antagonists of the present invention can be measured in a variety of in vitro assays. Exemplary assays are shown below.

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored.

AYPGKF is a known PAR4 agonist. An alternative PAR4 agonist is H-Ala-Phe(4-F)-Pro-Gly-Trp-Leu-Val-Lys-Asn-Gly-NH$_2$. As shown in Example B of WO2013/163279, H-Ala-Phe(4-F)-Pro-Gly-Trp-Leu-Val-Lys-Asn-Gly-NH$_2$ was validated as a PAR4 agonist in the FLIPR assay. A side-by-side comparison of the IC$_{50}$ values of ~180 compounds were performed using AYPGKF versus H-Ala-Phe(4-F)-Pro-Gly-Trp-Leu-Val-Lys-Asn-Gly-NH$_2$. The results demonstrated a strong correlation between the two assays. Additionally, H-Ala-Phe(4-F)-Pro-Gly-Trp-Leu-Val-Lys-Asn-Gly-NH$_2$ has improved agonist activity as compared to AYPGKF with an EC$_{50}$ that is 10 fold lower than the EC$_{50}$ for AYPGKF in the FLIPR assay. H-Ala-Phe(4-F)-Pro-Gly-Trp-Leu-Val-Lys-Asn-Gly-NH$_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown below. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

The compounds of the current invention can be tested in vitro for their ability to inhibit platelet aggregation induced by alpha-thrombin as shown below. Alpha-thrombin activates both PAR1 and PAR4. The ability of a selective PAR4 antagonist of the present invention to inhibit platelet aggregation can be measured using a standard optical aggregometer.

The compounds of the current invention can be tested in vitro for their ability to inhibit platelet aggregation induced by tissue factor as shown below. The conditions in this assay mimic the physiological events during thrombus formation. In this assay, platelet aggregation in human PRP is initiated by the addition of tissue factor and $CaCl_2$. Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

The activity of the PAR4 antagonists of the present invention can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrically-induced carotid arterial thrombosis, $FeCl_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention.

Assays

Materials
1) PAR1 and PAR4 Agonist Peptides
SFFLRR is a known high affinity PAR1 selective agonist peptide. (Reference: Seiler, S. M., "Thrombin receptor antagonists", *Seminars in Thrombosis and Hemostasis*, 22(3):223-232 (1996).) The PAR4 agonist peptides AYPGKF and H-Ala-Phe(4-F)-Pro-Gly-Trp-Leu-Val-Lys-Asn-Gly-$NH_2$ were synthesized. H-Ala-Phe(4-F)-Pro-Gly-Trp-Leu-Val-Lys-Asn-Gly-$NH_2$ showed improved PAR4 agonist activity over AYPGKF in the FLIPR assay ($EC_{50}$ value of 8 μM for H-Ala-Phe(4-F)-Pro-Gly-Trp-Leu-Val-Lys-Asn-Gly-$NH_2$ and 60 μM for AYPGKF) and in washed platelet aggregation assay ($EC_{50}$ value of 0.9 μM for H-Ala-Phe(4-F)-Pro-Gly-Trp-Leu-Val-Lys-Asn-Gly-$NH_2$ and 12 μM for AYPGKF).
2) PAR4 Expressing Cells
HEK293 cells stably expressing PAR4 were generated by a standard method of transfection of human PAR4 (F2R23) cDNA expression vector and selected based on PAR4 protein expression or mRNA expression. Those cells demonstrated functional responses to PAR4 agonist peptide-induced intracellular calcium elevation using FLIPR® (Fluorometric Imaging Plate Reader. Molecular Devices Corp.). These cells also express endogenous PAR1 and can elicit calcium signal upon stimulation with PAR1 agonist peptide. Therefore, the same cells were also used to determine selectivity against PAR1 and agonist activity for both receptors. Cells from HEK293 PAR4 Clone 1.2A (BMS Arctic ID 383940) were propagated and used for calcium mobilization studies.
3) Preparation of Platelet Rich Plasma (PRP)
Human blood was collected in 3.8% sodium citrate at a ratio of 1 ml per 9 ml blood and centrifuged in a Sorvall® RT6000B centrifuge at 900 revolution per minute (rpm) at room temperature (RT) for 15 minutes. PRP was collected and used for aggregation assay. Refludan (Berlex Labs, Wayne, N.J.), a recombinant hirudin, at a final concentration of 1 unit/mL was added to the sample to selectively prevent PAR1 activation induced by residual alpha-thrombin contamination. The remaining blood sample was centrifuged at 2500 rpm at room temperature for 5 minutes to collect platelet-poor plasma (PPP).
4) Preparation of Washed Platelets (WP)
Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at $\sim 2.5 \times 10^8$/ml in Tyrode's Buffer (137 mM NaCl, 2 mM KCl, 1.0 mM $MgCl_2$, 1 mM $CaCl_2$, 5 mM glucose, 20 mM HEPES pH 7.4).

FLIPR Assay in PAR4-Expressing HEK293 Cells

FLIPR-based calcium mobilization assay in HEK293 cells was used to measure PAR4 antagonism, agonism, and selectivity against PAR1. The activity of the PAR4 antagonists of the present invention were tested in PAR4 expressing cells by monitoring H-Ala-Phe(4-F)-Pro-Gly-Trp-Leu-Val-Lys-Asn-Gly-$NH_2$-induced intracellular calcium mobilization. Counter screens for agonist activity and PAR1 antagonist activity were also performed. Briefly, PAR1/PAR4-expressing HEK293 cells were grown in DMEM (Life Technology, Grand Island, N.Y.) containing 1090% heat-inactivated FBS, 1% Penicillin-Streptomycin, 10 μg/mL blasticidin, and 100 μg/mL Zeocin at 37° C. with 5% $CO_2$. Cells were plated overnight prior to the experiment in a black 384-well Purecoat Amine clear bottom plate (Becton Dickinson Biosciences, San Jose, Calif.) at 10,000 cells/well in 30 μL growth medium and incubated in a humidified chamber at 37° C. with 5% $CO_2$ overnight. Prior to compound addition, the cell medium was replaced with 40 μL of 1× calcium and magnesium-containing Hank's Balanced Saline Solution (HBSS) (with 20 mM HEPES) and 1:1000 diluted fluorescent calcium indicator (Codex Biosolutions, Gaithersburg, Md.). After a 30 minute incubation period at 37° C., and a further 30 minute incubation and equilibration period at room temperature, 20 μL test compound (diluted in 1×HBSS buffer) was added at various concentrations at 0.17% dimethyl sulfoxide (DMSO) final concentration. Changes in fluorescence intensity were measured using a Functional Drug Screening System (FDSS, Hamamatsu, Japan) to determine agonist activities. The cells were then incubated for 30 minutes at room temperature followed by addition of 20 μL of agonist peptide for antagonist activity measurement. The PAR4 agonist peptide (H-Ala-Phe(4-F)-Pro-Gly-Trp-Leu-Val-Lys-Asn-Gly-$NH_2$) and the PAR1 agonist peptide (SFFLRR) were routinely tested to ensure a proper response at the $EC_{50}$ value in the assay (~5 μM for PAR4 agonist peptide and ~2 μM for PAR1 agonist peptide). Compound potency was derived from 11-point concentration-response curves.

Gamma Thrombin Induced Platelet Aggregation Assays

The ability of the compounds of the current invention to inhibit platelet aggregation induced by gamma-thrombin was tested in a 96-well microplate aggregation assay format. Briefly, 90 μL of PRP or washed platelets were pre-incubated for 5 minutes at 37° C. with 3-fold serially diluted test compound, which was prepared as a 100-fold stock solution in dimethyl sulfoxide (DMSO). Aggregation was initiated by addition of 10 µL of gamma-thrombin (Haematologic Technologies, Inc. Essex Junction, Vt.) at 50-100 nM final concentration, which was titrated daily to achieve 80% platelet aggregation. The plate was then placed into a SpectraMax® Plus Plate Reader (Molecular Devices) at 37° C. Platelet aggregation was monitored at a wavelength of 405 nm using a kinetic analysis mode. Prior to the first data collection time point, the plate was shaken for 10 seconds to allow thorough mixing. Data was subsequently collected every 10 seconds for up to 7 minutes total. Data was collected using SoftMax® 5.4.1 software and exported to Microsoft Excel for analysis. The optical density (OD) values at the time point that achieved 75% platelet activation by agonist alone were used for analysis. The OD value from a PRP sample without any treatment served as $OD_{maximum}$, and the OD value from a PPP sample containing no platelets served as the $OD_{minimum}$. Inhibition of platelet aggregation (IPA) was calculated based on the formula: % IPA=(100−100*[$OD_{compound}$−$OD_{minimum}$]/[$OD_{maximum}$−$OD_{minimum}$]).

The $IC_{50}$ value of the test compound was calculated by fitting the % IPA values to the one-site concentration response equation: $Y=A+(B-A)/(\{1+(C/X)^D\})$, using XLfit for 32 bit Excel® Version 2 Build 30 (ID Business Solutions Limited).

The aggregation assays were also employed to test the selectivity of the compound against other platelet receptors by using SFFLRR for PAR1, collagen (Chrono-Log, Havertown, Pa.) for collagen receptors, ADP for P2Y1 and P2Y12 and U46619 (Cayman Chemical, Ann Arbor, Mich.) for thromboxane receptors.

Alpha-Thrombin Induced Platelet Aggregation Assays

The ability of PAR4 antagonists to inhibit platelet aggregation induced by alpha-thrombin can be tested using human washed platelets. The antagonists are pre-incubated with washed platelets for 20 min. Aggregation is initiated by addition of 1.5 nM alpha-thrombin (Haematologic Technologies, Essex Junction, Vt.) to 300 µl of washed platelets at stirring speed of 1000 rpm. Platelet aggregation is monitored using an Optical Aggregometer (Chrono-Log, Havertown, Pa.) and the area under the curve (AUC) at 6 min was measured. $IC_{50}$ values are calculated using vehicle control as 0% inhibition.

Tissue Factor-Induced Platelet Aggregation Assay

The ability of PAR1 or PAR4 antagonists to inhibit platelet aggregation induced by endogenous thrombin can be tested in a tissue factor driven aggregation assay. Aggregation is initiated by addition of $CaCl_2$ and recombinant human tissue factor, which results in the generation of thrombin through activation of the coagulation pathway in the plasma. Anticoagulant agents such as corn trypsin inhibitor (Haematologic Technologies, Essex Junction, Vt.) at 50 µg/ml and PEFABLOC® FG (Centerchem, Norwalk, Conn.) are also added to the sample to prevent fibrin clot formation during the time of the study. Platelet aggregation is monitored using standard instrumentation including optical aggregometer or impedance aggregometer.

The following table sets out the results obtained employing various compounds of the invention tested in the PAR4 FLIPR assay.

TABLE

| Ex. No. | PAR4 FLIPR assay ($IC_{50}$, nM) |
|---|---|
| 1 | 80 |
| 2 | 790 |
| 3 | 330 |
| 4 | 520 |
| 5 | 940 |
| 6 | 1.0 |
| 7 | 95 |
| 8 | 100 |
| 9 | 5.0 |
| 10 | 300 |
| 11 | 7.5 |
| 12 | 8.1 |
| 13 | 12 |
| 14 | 170 |
| 15 | 5.9 |
| 16 | 110 |
| 17 | 75 |
| 18 | 6.2 |
| 19 | 5.9 |
| 20 | 31 |
| 21 | 8.8 |
| 22 | 18 |
| 23 | 14 |
| 24 | 8.3 |
| 25 | 15 |
| 26 | 23 |
| 27 | 20 |
| 28 | 43 |
| 29 | 60 |
| 30 | 8.8 |
| 31 | 450 |
| 32 | 2300 |
| 33 | 570 |
| 34 | 760 |
| 35 | 25 |
| 36 | 64 |
| 37 | 60 |
| 38 | 820 |
| 39 | 2000 |
| 40 | 23 |
| 41 | 450 |
| 42 | 81 |
| 43 | 330 |
| 44 | 79 |
| 45 | 25 |
| 46 | 14 |
| 47 | 53 |
| 48 | 3.1 |
| 49 | 19 |
| 50 | 5.7 |
| 51 | 7.1 |
| 52 | 550 |
| 53 | 290 |
| — | — |

Methods of Preparation

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis*, 4th Edition. Wiley-Interscience (2006)).

Compounds of Formula I of this invention can be obtained by palladium catalyzed cross coupling of aryl halides of Formula Ia with organometallic species $R_3$-M as shown in Scheme 1.

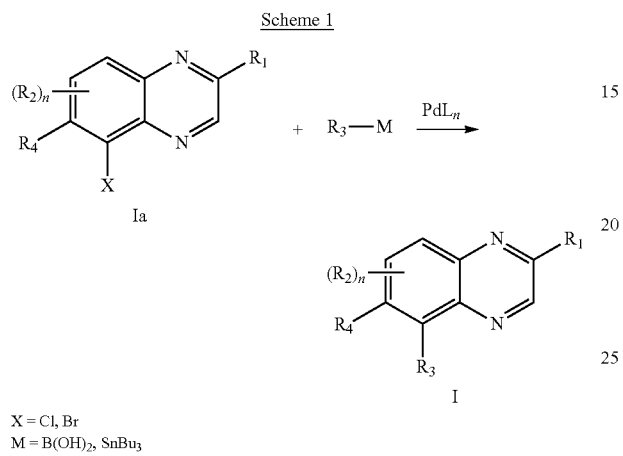

X = Cl, Br
M = B(OH)$_2$, SnBu$_3$

Alternatively, compounds of Formula I can also be prepared from palladium catalyzed cross coupling of arylboronic acids of Formula Ib with halides $R_3$—X shown in Scheme 2.

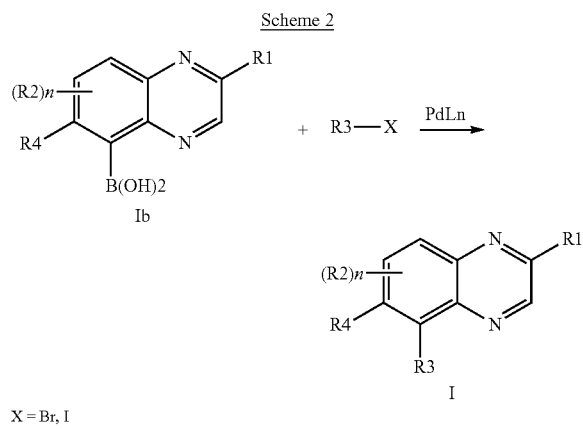

X = Br, I

One way to prepare the quinoxalines of Formula Ia and Ib is through the condensation reaction of the diamine Ic with ketoaldehyde Id, as shown in Scheme 3. In general, the condensation will give two regioisomers that may be separated by chromatography. Structure of Formula Ia can be converted to boronic acid Ib via Suzuki-Miyaura reaction.

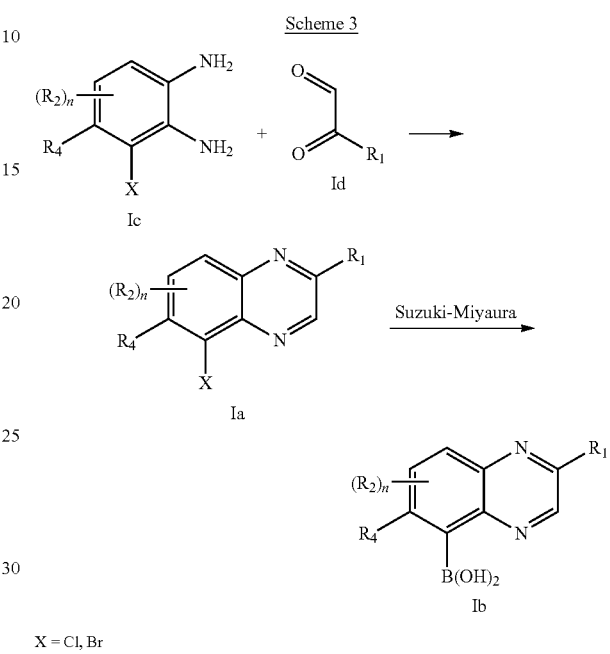

X = Cl, Br

A regio specific synthesis of quinoxalines of Formula Ia and Ib is shown in Scheme 4. A properly protected ortho-nitro aniline Ie is alkylated with methyl bromoacetate to yield compound If. Deprotection of compound If and reduction of compound Ig should initiate cyclization to give rise to compound Ih. Compound Ih can be oxidized to quinoxaline-2-one of Formula Ii, which can be converted to the intermediate Ij with oxophosphorus halides. The halides in compound Ij can be displaced with a nucleophile containing an $R_1$ group to compound Ia, and compounds of Formula Ia can be converted to corresponding boronic acids of Formula Ib via Suzuki-Miyaura reaction. Intermediate Ii could also be converted to Ik by condensation reaction with sodium chlorodifluoroacetate in the presence of a base such as $K_2CO_3$. The difluoroalkoxy can be displaced with a nucleophile containing an $R_1$ group to compound Ia.

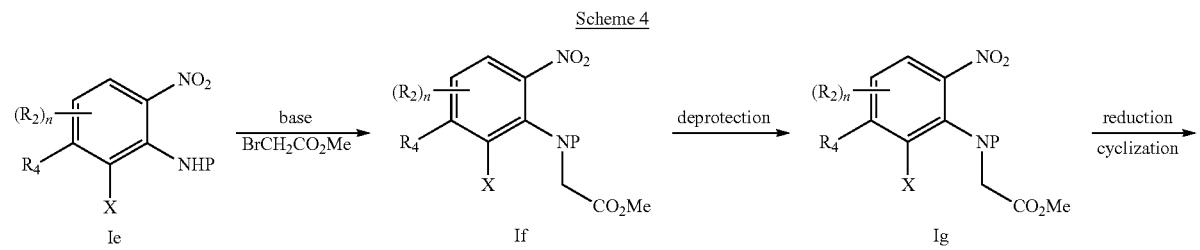

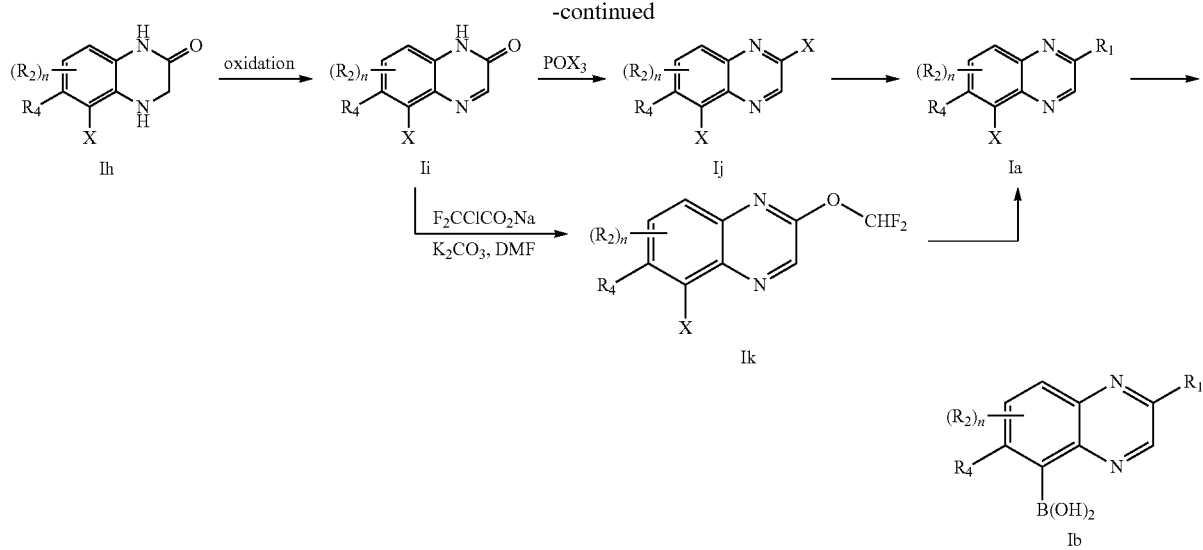

X = Cl, Br

Compounds of Formula II of this invention can be obtained as shown in Scheme 5. Compound IIa can be condensed with dicarbonyl IIb to give compound IIc. Acid catalyzed cyclization provides the key bromide IId. Palladium catalyzed cross coupling reaction with an appropriate boronic acid furnishes compound II.

Compounds of Formula III of this invention can be obtained as shown in Scheme 6. Compound IIIa can be condensed with dimethylacetal IIIb to give compound IIIc. Acid catalyzed cyclization and triflate formation provides the key coupling partner IIId. Palladium catalyzed cross coupling reaction with an appropriate boronic acid furnishes the compound of Formula III Scheme 5

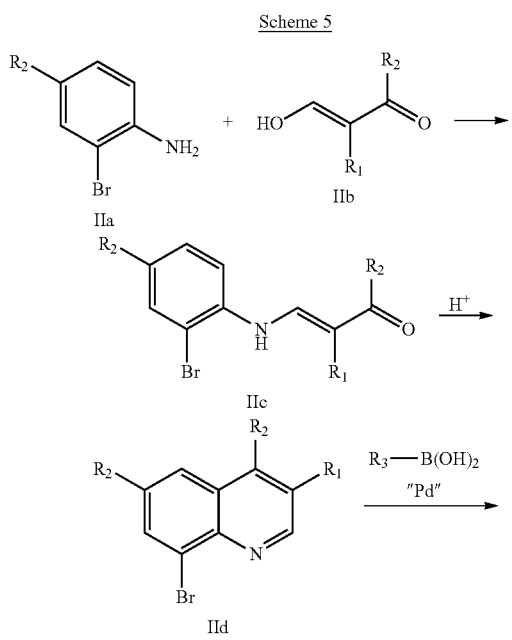

Scheme 6

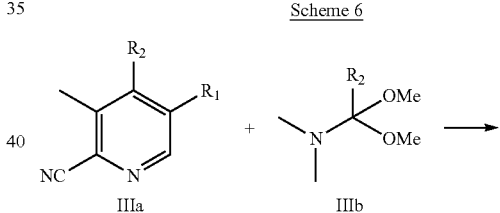

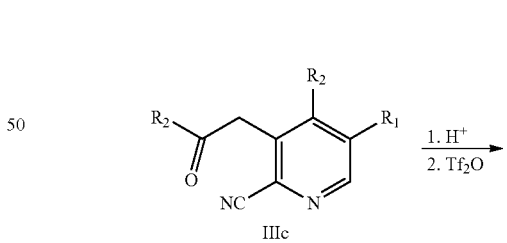

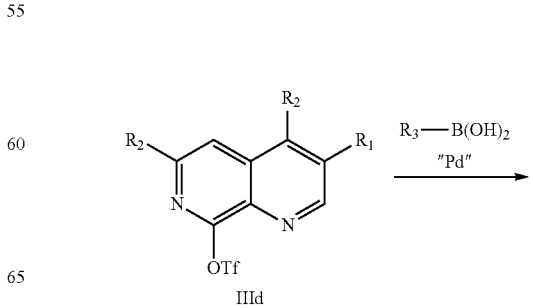

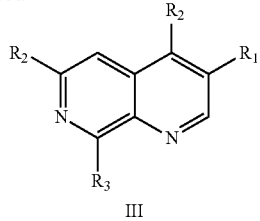

III

Compounds of Formula IV of this invention can be obtained as shown in Scheme 7. Compound IVa can be condensed with dimethylacetal IVb to give compound IVc. Acid catalyzed cyclization and triflate formation provides the key coupling partner IVd. Palladium catalyzed cross coupling reaction with an appropriate boronic acid furnishes the compound of Formula IV.

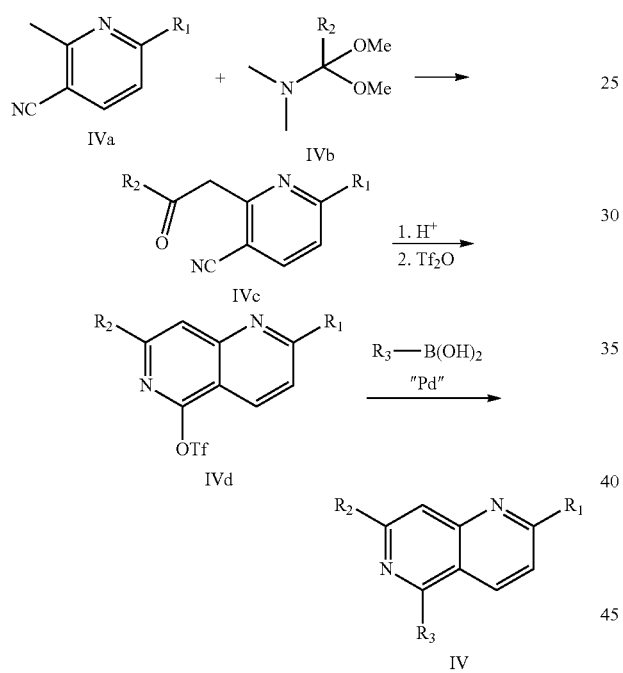

Scheme 7

Compounds of Formula V of this invention can be obtained as shown in Scheme 8. Compound Va can be condensed with acid chloride Vb to give compound Vc. Acid catalyzed cyclization and carbonyl alkylation provides the key bromide Vd. Palladium catalyzed cross coupling reaction with an appropriate boronic acid furnishes the compound of Formula V.

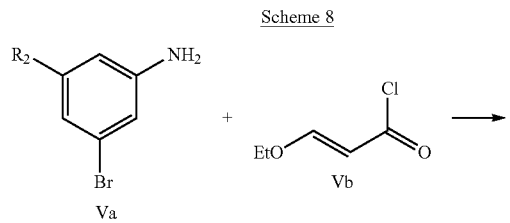

Scheme 8

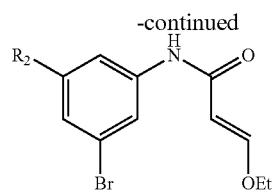

Vc

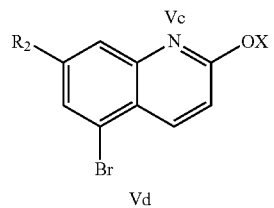

Vd

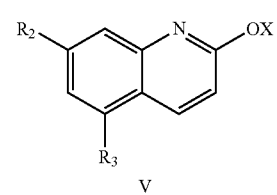

V

Compounds of Formula VI of this invention can be obtained as shown in Scheme 9. Compound VIa can be condensed with dicarbonyl compound VIb to give compound VIc. Palladium catalyzed cross coupling reaction with an appropriate boronic acid furnishes the compound of Formula VI.

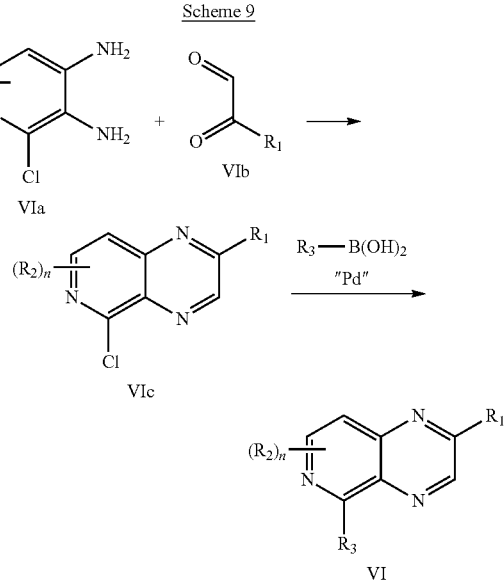

Scheme 9

In this invention, compounds of Formula VII can be obtained through the synthetic route shown in Scheme 10. Beginning with aryl chloride VIIa, palladium catalyzed cross coupling of various boronic acids or stannanes yields substituted anilines of structure VIIb. Nitration of compound VIIb and reduction of compound VIIc allows access to compounds of Formula VIId. Base mediated condensation of dianiline VIId with substituted bromo-ketones provides heterocycles of Formula VIIe. A final palladium-catalyzed cross coupling with aryl boronic acids or stannanes then furnishes the compounds of Formula VII.

Scheme 10

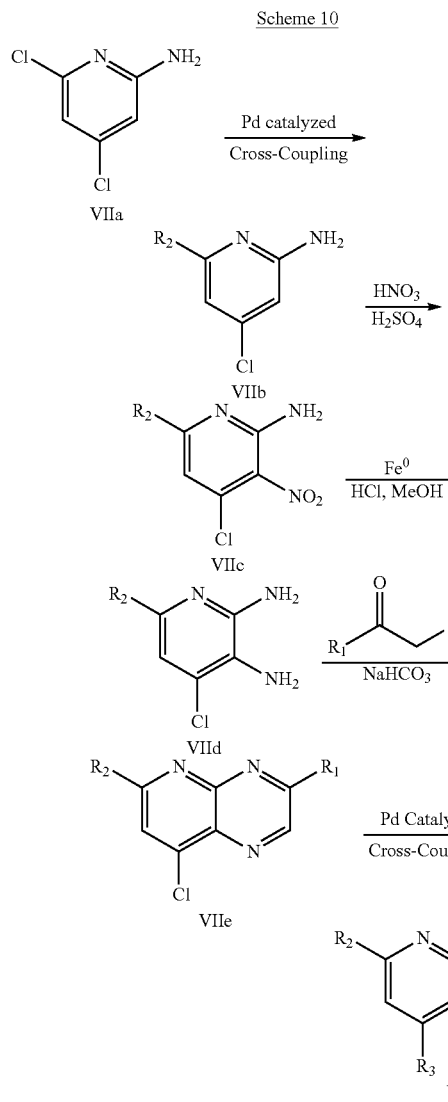

Compounds of Formula VIII of this invention can be obtained by palladium catalyzed cross coupling of aryl boronic acids or stannanes with aryl chloride VIIIc as shown in Scheme 11. Compound VIIIa can be condensed with amidines to give compound VIIIb. Phosphorous oxychloride conversion of compound VIIIb to aryl chloride VIIIc followed by palladium-catalyzed cross coupling with aryl boronic acids or stannanes furnishes the compound of Formula VIII.

Scheme 11

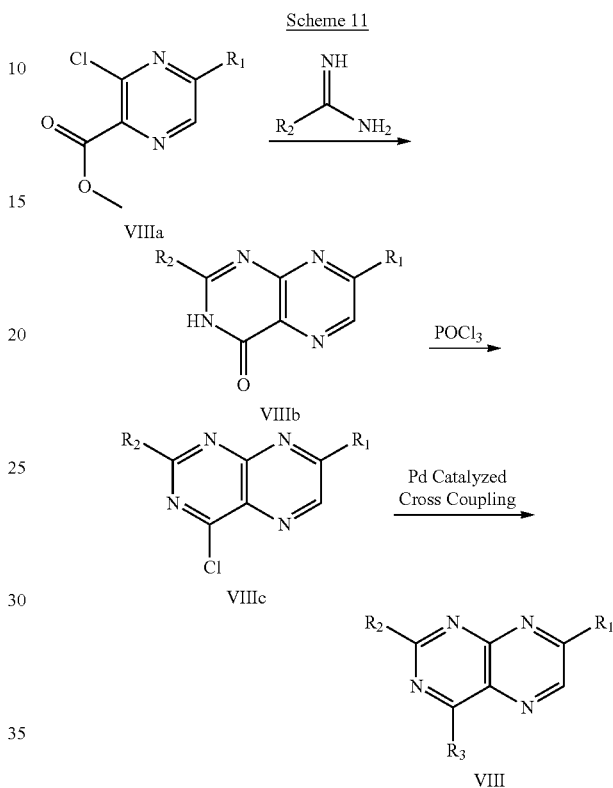

Compounds of formula I of this invention can be obtained by palladium catalyzed cross coupling of aryl halides with aryl boronic ester X as shown in Scheme 12. I can be brominated to give Xa. I or Xa can be reacted with aryl halides or aryl boronic acids under palladium catalyzed conditions to give additional compounds of formula I. Alternatively, Xa can be reacted with amines under palladium catalyzed conditions to give other compounds of formula I.

Scheme 12

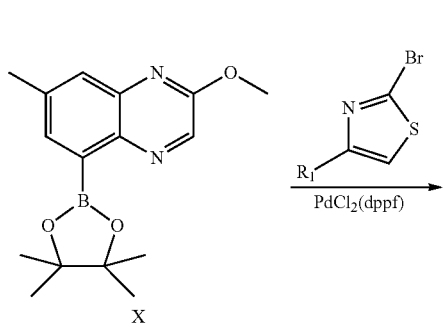

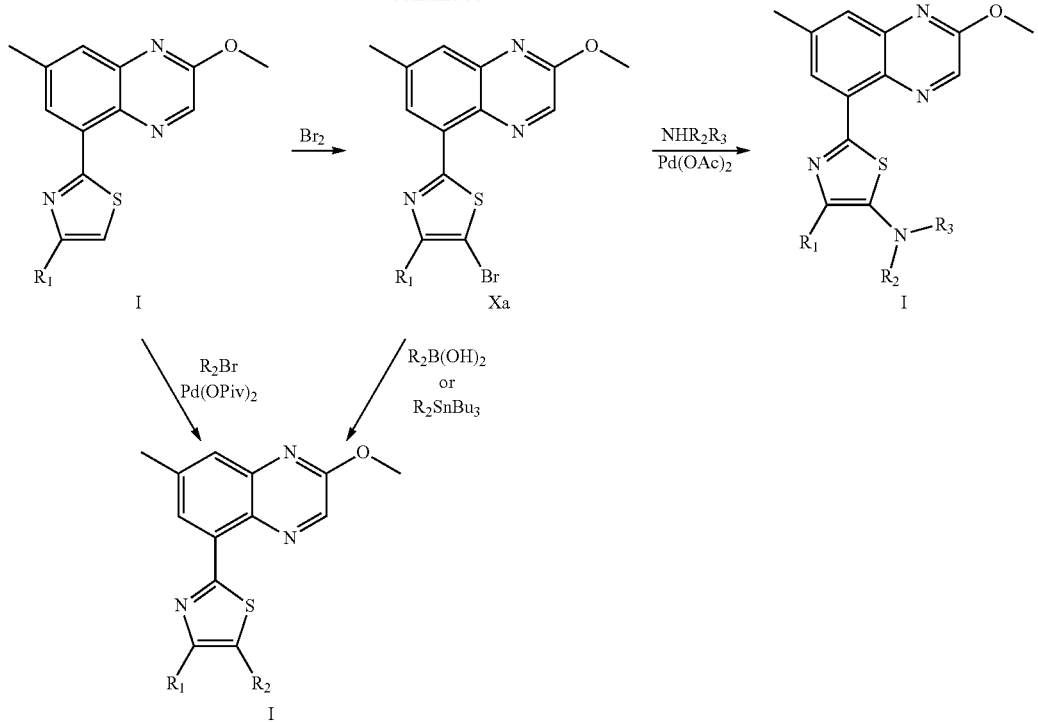

Alternatively, compounds of formula I can be prepared as in Scheme 13. Intermediate Xb can be converted to the thioamide Xc, which can undergo a condensation reaction with alpha halo ketones to form compounds of formula I.

Compounds of formula I can alternatively be prepared as shown in Scheme 14. Xb can undergo a palladium catalyzed cross coupling with aryl stannane to give Xd, which can undergo a palladium catalyzed cross coupling reaction with aryl boronic acids to give compounds of formula I.

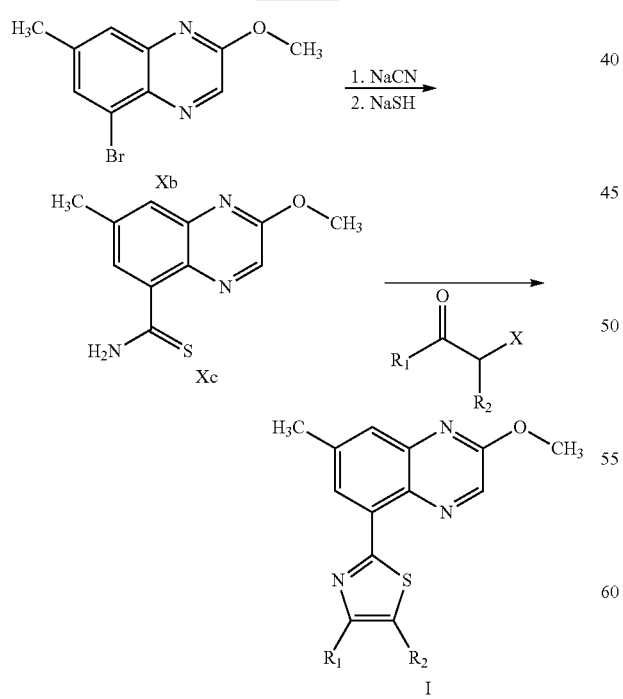

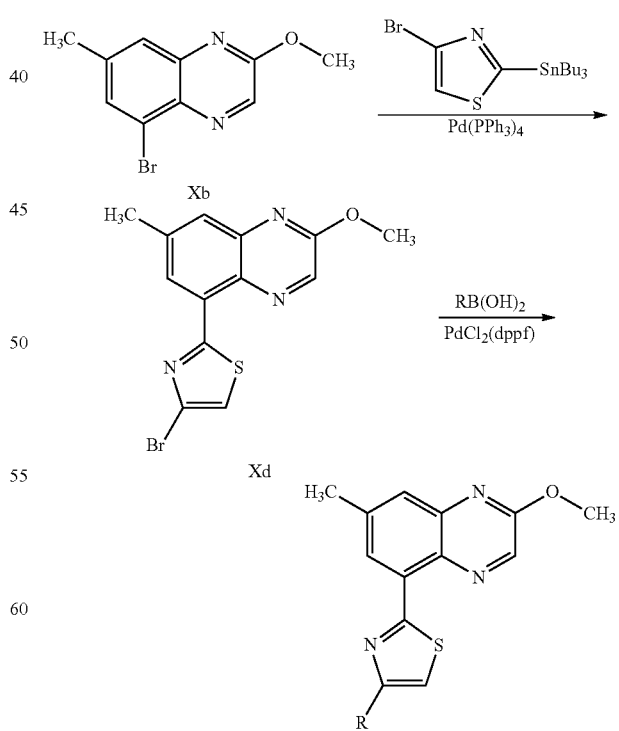

General Methods

The following methods were used in the exemplified Examples, except where noted otherwise.

Products were analyzed by reverse phase analytical HPLC carried out on a Shimadzu Analytical HPLC system running Discovery VP software using one of the following methods:

Method A: PHENOMENEX® Luna C18 column (4.6×50 mm or 4.6×75 mm) eluted at 4 mL/min with 2, 4 or 8 min gradient from 100% A to 100% B (A: 10% methanol, 89.9% water, 0.1% TFA; B: 10% water, 89.9% methanol, 0.1% TFA, UV 220 nm).

Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA. UV 220 nm).

Method C: PHENOMENEX® Luna C, 18 column (4.6× 50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm).

Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B: 10% water, 89.9% methanol, 0.1% $NH_4OAc$, UV 220 nm).

Method E: BEH C18 2.1×50 mm; A: water+0.05% TFA; B: acetonitrile+0.05% TFA; wavelength 220 nm; flow rate 0.8 mL/min: 0% B to 100% B in 1 minute, gradient time 1.5 min.

Method F: BEH C18 2.1×50 mm; A: water+0.05% TFA; B: acetonitrile+0.05% TFA; wavelength 220 nm; flow rate 0.8 mL/min; 0% B to 50% B in 1 minute, gradient time 1.5 min.

Method G: BEH C18 2.1×50 mm; A: water+0.05% TFA; B: acetonitrile+0.05% TFA; wavelength 220 nm; flow rate 0.8 mL/min; 50% B to 100% B in 1 minute, gradient time 1.5 min.

Reverse phase preparative HPLC was carried out using a Shimadzu Preparative HPLC system running Discovery VP software using one of the following methods.

Method A: PHENOMENEX® Axia Luna 5 µM C, 18 30×75 mm column with a 10 min gradient at 40 mL/min from 100% A to 100% B (A: 10% acetonitrile, 89.9% water, 0.1% TFA; B: 10% water, 89.9%6 acetonitrile, UV 220 nm).

Method B: YMC Sunfire 5 µM C, 18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

Method C: XBridge C18, 19×200 mm column, 5-µm particles; Mobile Phase A: 5:95 acetonitrile:water with 0.1% trifluoroacetic acid; Mobile Phase B: 95:5 acetonitrile:water with 0.1% trifluoroacetic acid; Flow: 20 mL/min.

Method D: Waters XBridge C18, 19×100 mm column, 5-µm particles; Mobile Phase A: 5:95 acetonitrile:water with 10-mM ammonium acetate; Mobile Phase B: 95:5 acetonitrile:water with 10-mM ammonium acetate; Flow: 20 mL/min.

Method E: PHENOMENEX™ Luna 5 µM C18 30×100 mm column with a 10 min gradient at 40 mL/min from 100% A to 100% B (A: 10% acetonitrile, 89.9%6 water, 0.1% TFA; B: 10% water, 89.9% acetonitrile, 0.1% TFA, UV 220 nm).

Method F: PHENOMENEX® Luna 5 µM C18 30×100 mm column with a 10 min gradient at 40 mL/min from 100% to 100% B (A: 10% methanol, 89.9% water, 0.1% TFA; B: 10% water, 89.9%0 methanol, 0.1% TFA, UV 220 nm).

Method G: Waters XBridge C18, 19×200 mm, 5-µm particles; Mobile Phase A: 5:95 acetonitrile:water with 0.1% formic acid; Mobile Phase B: 95:5 acetonitrile:water with 0.1% formic acid; Flow: 20 mL/min.

LCMS chromatograms were obtained on a Shimadzu HPLC system running Discovery VP software, coupled with a Waters ZQ mass spectrometer running MassLynx version 3.5 software using:

Method A: A linear gradient using solvent A (10% acetonitrile, 90% water, 0.1% of TFA) and solvent B (90% acetonitrile, 10% water, 0.1% of TFA); 0-100% of solvent B over 2 min and then 100% of solvent B over 1 min. Column: PHENOMENEX® Luna 3u C18(2) (2.0×30 mm). Flow rate was 5 ml/min. And UV detection was set to 220 nm. The LC column was maintained at room temperature.

Method B: A linear gradient using solvent A (10% methanol, 90% water, 0.1% of TFA) and solvent B (90% methanol, 10% water, 0.16 of TFA); 0-100% of solvent B over 4 min and then 100% of solvent B over 1 min. Column: PHENOMENEX® Luna 5u C18 (4.5×30 mm). Flow rate was 4 ml/min. And UV detection was set to 220 nm. The LC column was maintained at room temperature.

Method C: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3u C18(2) (2.0×30 mm). Flow rate was 1 ml/min. And UV detection was set to 220 nm. The LC column was maintained at room temperature.

Method D: A linear gradient using solvent A (10% methanol, 90% water, 0.1% of TFA) and solvent B (90% methanol, 10% water, 0.1% of TFA): 0-100% of solvent B over 2 min and then 100% of solvent B over 1 min. Column: PHENOMENEX® Luna 3u C, 18(2) (4.5×30 mm). Flow rate was 5 ml/min. And UV detection was set to 220 nm. The LC column was maintained at room temperature.

Method E: 30-95% acetonitrile in water with 0.1% TFA in 8 min run, Waters Xbridge 4.6×50 mm 5 um C18, flow rate 1.2 mL/min and UV detection was set to 220 nm. The LC column was maintained at room temperature.

Method F: 10-95% methanol in water, 0.1% TFA in a 10 min run, PHENOMENEX® Onyx Monolithic 4.6×100 mm 5 um C18, flow rate 2.0 mL/mL and UV detection was set to 220 nm. The LC column was maintained at room temperature.

Method G: 5-95% acetonitrile in water, 10 mM of modifier in 6 min run, Waters Xbridge 2.1×50 mm 5 um C18, flow rate 1.0 mL/min and UV detection was set to 220 nm. The LC column was maintained at room temperature.

Method H: BEH C, 18 2.1×50 mm A: water+0.05% TFA; B: acetonitrile+0.05% TFA; wavelength 220 nm; flow rate 0.8 mL/min; gradient time 1.5 min; 2 to 98% B.

Method I: BEH C18 2.1×50 mm; A: water+0.05% TFA; B: acetonitrile+0.05% TFA; wavelength 220 nm; flow rate 0.8 mL/min; gradient time 1.5 min: 2 to 52% B.

Method J: BEH C18 2.1×50 mm; A: water+0.05% TFA; B: acetonitrile+0.05% TFA; wavelength 220 nm; flow rate 0.8 mL/min; gradient time 1.5 min; 48 to 98% B.

Method K: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate;

Temperature: 50° C.; Gradient: 0-100% B over 3 minutes, then a 0.75-minute hold at 100% B; Flow: 1.11 mL/min; Detection: UV at 220 nm.

Method L: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

In addition, the following orthogonal HPLC conditions were used to check the purity of the compounds:

Method A: Two analytical LC/MS injections were used to determine the final purity. Injection 1 condition: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 um (4.6×150 mm). Flow rate was 2 ml/min. And UV detection was set to 220 nm. The LC column was maintained at room temperature. Injection 2 conditions: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 um (4.6×150 mm). Flow rate was 2 ml/min. And UV detection was set to 220 nm. The LC column was maintained at room temperature.

Method B: Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

EXAMPLES

The invention is further defined in the following Examples. It should be understood that the Examples are given by the way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

ABBREVIATIONS

AcOH acetic acid
BINAP 2,2'-bis(diphenylphosphino)-1,1'-binaphthylene
Boc tert-butoxycarbonyl
$BOC_2O$ di(tert-butoxycarbonyl) ether
BuLi butyl lithium
DCM dichloromethane
DIPEA diisopropylethylamine
DMAP dimethylaminopyridine
DMF dimethylformamide
EDC 1-(3-dimethylaminopropyl)-3-ethylcarbodiimide hydrochloride
EtOAc ethyl acetate
HOBt hydroxybenzotriazole
MeCN acetonitrile
MeOH methanol
$NH_4OAc$ ammonium acetate
$PdCl_2(dppf)\text{-}CH_2Cl_2$ [1,1'-bis(diphenylphosphino)ferrocene]dichloropalladium(II), dichloromethane adduct
$Pd(Ph_3)_4$ tetrakis(triphenylphosphine)palladium
TEA triethylamine
TFA trifluoroacetate
THF tetrahydrofuran
HPLC high pressure liquid chromatography
MS mass spectrometry
g gram(s)
h or hr hour(s)
min. minute(s)
mL milliliter(s)
mmol millimole(s)
RT retention time Intermediate I-1

2-(difluoromethoxy)-7-methyl-5-(4,4,5,5-tetramethyl-1,3,2-dioxaborolan-2-yl) quinoxaline

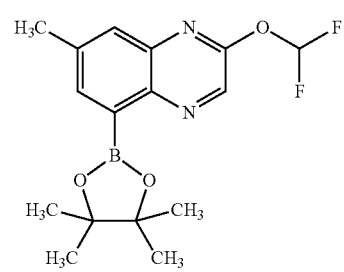

(I-1)

Intermediate I-1A: tert-butyl N-(2-bromo-4-methyl-6-nitrophenyl)-N-[(tert-butoxy) carbonyl]carbamate

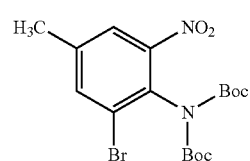

(I-1A)

To a solution of 2-bromo-4-methyl-6-nitroaniline (9.6 g, 41.6 mmol) in THF (60 mL) was added DMAP (0.508 g, 4.16 mmol), followed by $BOC_2O$ (22.67 g, 104 mmol) as a solid. The mixture was stirred at room temperature overnight. Solvent was removed by vacuum. The crude product was dissolved in a small amount of chloroform and charged to a 120 g silica gel cartridge (2 separate columns) which was eluted with 5% EtOAc in hexanes for 4 min., then a 12 min gradient from 5% to 30% EtOAc in hexanes. The desired fractions were combined and concentrated to give Intermediate I-1A (17.12 g, 39.7 mmol, 96% yield) as a white solid. $^1$H NMR (500 MHz, chloroform-d) δ 7.80-7.79

(m, 1H), 7.73 (dd, J=1.9, 0.8 Hz, 1H), 2.48 (s, 3H), 1.42 (s, 18H); LC-MS: method A, RT=1.90 min, MS (ESI) m/z: 230.0 and 232.0 (M−2 Boc)+.

Intermediate I-1B: tert-butyl (2-bromo-4-methyl-6-nitrophenyl)carbamate

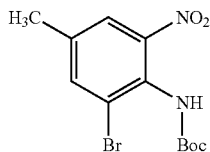

(I-1B)

To a solution of Intermediate I-1A (17.1 g, 39.6 mmol) in dichloromethane (60 mL) was added TFA (6.11 mL, 79 mmol) and the mixture was stirred at room temperature for 1.0 h. The reaction was quenched by addition of saturated sodium bicarbonate, extracted with dichloromethane (3×), dried over sodium sulfate. After evaporation of solvent, Intermediate I-1B was obtained as a yellow solid (12.88 g, 88% yield): $^1$H NMR (500 MHz, chloroform-d) δ 7.71 (d, J=1.1 Hz, 1H), 7.68 (dd, J=1.9, 0.8 Hz, 1H), 2.42 (s, 3H), 1.51 (s, 9H); LC-MS: method A, RT=1.53 min, MS (ESI) m/z: 231.0 and 233.0 (M-Boc)+.

Intermediate I-1C: methyl 2-((2-bromo-4-methyl-6-nitrophenyl)(tert-butoxycarbonyl) amino)acetate

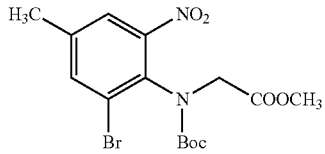

(I-1C)

Intermediate I-1B (12 g, 26.3 mmol) was dissolved in DMF (80 mL), cooled with a water bath. Cs$_2$CO$_3$ (25.8 g, 79 mmol) was added. The dark brown solution was stirred at room temperature for 10 min, then methyl 2-bromoacetate (4.37 mL, 47.6 mmol) was added dropwise. After addition of methyl bromoacetate, the brown color faded to yellow. The mixture was stirred at room temperature for 1.0 h, diluted with EtOAc, quenched with water. The organic layer was collected, washed with brine, dried over sodium sulfate. After evaporation of solvent, the crude product was dissolved in a small amount of chloroform and charged to a 330 g silica gel cartridge which was eluted with 5% EtOAc in hexanes for 5 min., then a 12 min gradient from 5% to 50% EtOAc in hexanes. The desired fractions were combined and concentrated to give Intermediate I-1C (15.2 g, 37.7 mmol, 95% yield) as an yellow oil. $^1$H NMR (500 MHz, chloroform-d) indicated a mixture of rotamers: δ 7.75-7.67 (m, 2H), 4.61-3.97 (m, 2H), 3.76 and 3.69 (s, 3H), 2.48 and 2.43 (s, 3H), 1.55 and 1.37 (s, 9H); LC-MS: method A, RT=1.70 min, MS (ESI) m/z: 303.0 and 305.0 (M-Boc)+.

Intermediate I-1D: methyl 2-((2-bromo-4-methyl-6-nitrophenyl)amino)acetate

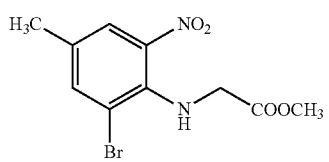

(I-1D)

To Intermediate I-1C (15.2 g, 37.7 mmol) was added 4.0 N HCl in dioxane (47.1 ml, 188 mmol) and the mixture was stirred at room temperature overnight. Solvent was removed under vacuum, chased with EtOAc (2×) to give Intermediate I-1D (13.6 g, 40.1 mmol, 106% yield) as a yellow solid. $^1$H NMR (500 MHz, methanol-d$_4$) δ 7.88 (dd, J=1.9, 0.6 Hz, 1H), 7.80 (dd, J=1.9, 0.6 Hz, 1H), 4.47 (d, J=17.3 Hz, 1H), 4.08 (d, J=17.1 Hz, 1H), 3.69 (s, 3H), 2.46 (s, 3H); LC-MS: Method A, RT=1.94 min, MS (ESI) m/z: 303.1 and 305.1 (M+H)+.

Intermediate I-1E: 5-bromo-7-methyl-3,4-dihydroquinoxalin-2(1H)-one

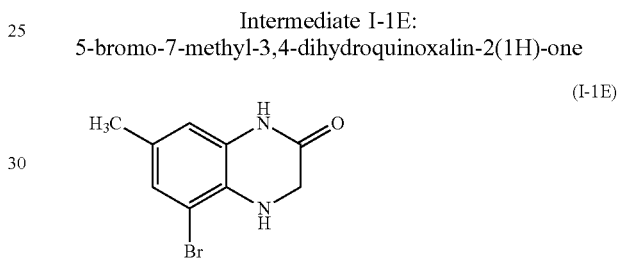

(I-1E)

To a solution of Intermediate I-ID (13.6 g, 40.1 mmol) in MeOH (100 mL) in a 1 L flask cooled with water bath was added concentrated HCl (13.35 mL, 160 mmol), followed by tin(II) chloride dihydrate (36.1 g, 160 mmol). The mixture was stirred at 68° C. for 2.5 h. MeOH was removed by vacuum. The crude was partitioned in water (100 mL)/EtOAc (200 mL), and the pH was adjusted to neutral with 4.0 N NaOH (ca 90 mL). The white precipitate formed was very fine particle that was very hard to remove by filtration. The mixture was transferred to a separatory funnel. The organic layer was collected. The aqueous was further extracted (2×200 mL) with EtOAc. The combined organic layer was washed with water (2×) and brine (2×), dried over sodium sulfate. After evaporation of solvent, Intermediate I-1E (8.36 g, 34.7 mmol, 87% yield) was obtained as a pale yellow solid. $^1$H NMR (500 MHz, DMSO-d$_6$) δ 10.37 (s, 1H), 6.87 (dd, J=1.8, 0.7 Hz, 1H), 6.56 (dd, J=1.1, 0.6 Hz, 1H), 5.46 (s, 1H), 3.76 (d, J=2.2 Hz, 2H), 2.14 (s, 3H); LC-MS: method A, RT=1.66 min. MS (ESI) m/z: 241.0 and 243.0 (M+H)+.

Intermediate I-1F: 5-bromo-7-methylquinoxalin-2-ol

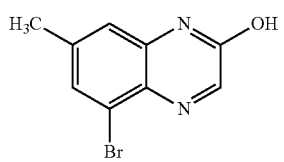

(I-1F)

To a suspension of Intermediate I-1E (6.7 g, 27.8 mmol) in MeOH (50 mL) in a 1 L flask was added 30% hydrogen peroxide (28.4 mL, 278 mmol), followed by 4.0 N NaOH (20.84 mL, 83 mmol). The mixture was stirred at room temperature for 5 min, then gently heated at 60° C. After 15 min heating, the reaction mixture turned strongly exothermic, suggesting an initiation of the reaction. The heating bath was removed and stirring continued for 30 min until the mixture turned completely clear. After cooled to room temperature with a water bath, MeOH was removed by vacuum. The mixture was then neutralized with 2.0 N HCl (to pH 2-3) and ice cooling. The precipitate formed was collected by filtration, washed with water, dried under vacuum in the air for 1.0 h and then at vacuum at 60° C. for 2.0 h, and under high vacuum to give Intermediate I-1F (6.55 g, 27.4 mmol, 99% yield) as an off-white solid. $^1$H NMR (500 MHz, DMSO-$d_6$) δ 12.52 (br. s., 1H), 8.17 (s, 1H), 7.49 (d, J=1.1 Hz, 1H), 7.08 (s, 1H), 2.40 (s, 3H; LC-MS: method A, RT=1.62 min, MS (ESI) m % z: 239.0 and 241.0 (M+H)$^+$.

Intermediate I-1G:
5-bromo-2-(difluoromethoxy)-7-methylquinoxaline

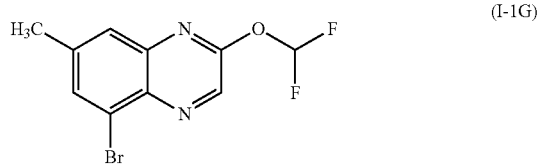 [SMILES: Cc1cc(Br)c2ncc(OC(F)F)nc2c1]

A mixture of Intermediate I-1F (7.4 g, 26.9 mmol) and potassium carbonate (18.56 g, 134 mmol) in DMF (120 mL) was heated at 100° C. for 5 min. Sodium 2-chloro-2,2-difluoroacetate (16.40 g, 107.6 mmol) was added in one portion, and the mixture was stirred at 100° C. for 10 min. The mixture turned from yellow slurry to brown. The mixture was cooled to room temperature, diluted with EtOAc and water, extracted with EtOAc (3×). The combined organic layer was washed with brine, dried over sodium sulfate. After evaporation of solvent, the crude product was dissolved in a small amount of chloroform/toluene and purified with a 330 g ISCO column eluted with 5% dichloromethane in hexanes for 3 min, then 5-70% DCM/hexanes for 40 min (12 min gradient time). The desired fractions were combined, concentrated to give Intermediate I-1G (6.0 g, 20.76 mmol, 77% yield) as a slightly yellow solid. $^1$H NMR (500 MHz, chloroform-d) δ 8.64 (s, 1H), 7.89 (d, J=1.7 Hz, 1H), 7.68 (dd, J=1.8, 1.0 Hz, 1H), 7.63 (t, $J_{HF}$=71.80 Hz, 1H), 2.59 (s, 3H); $^{19}$F NMR (471 MHz, chloroform-d) 8-89.82 (s, 2F); LC-MS: method A, RT=2.09 min, MS (ESI) m/z: 289.0 and 291.0 (M+H)$^+$.

Intermediate I-1

A mixture of Intermediate I-1G (1.04 g, 3.60 mmol), 4,4,4',4',5,5,5',5'-octamethyl-2,2'-bis(1,3,2-dioxaborolane) (1.370 g, 5.40 mmol), potassium acetate (0.883 g, 8.99 mmol) and [1,1'-bis(diphenylphosphino)ferrocene]dichloropalladium (II) complex with dichloromethane (1:1) (0.147 g, 0.180 mmol) in dioxane (14 mL) was degassed by bubbling argon for 10 min. The reaction vial was sealed and heated in microwave reactor at 135° C. for 30 min. The mixture was diluted with EtOAc/water, insoluble material was removed by filtration. The filtrate was extracted with EtOAc, washed with brine and dried over sodium sulfate. After evaporation of solvent, the crude product was dissolved in a small amount of toluene and charged to a 40 g silica gel cartridge which was eluted with 5% EtOAc in hexanes for 2 min., then a 18 min gradient from 5% to 75% EtOAc in hexanes. The desired fractions were concentrated and lyophilized to give Intermediate 1-1 (0.93 g, 72% yield) as a pale solid. $^1$H NMR was complicated by the presence of two sets of signals. $^{19}$F NMR indicated a single compound. $^{19}$F NMR (471 MHz, chloroform-d) δ −89.64 (s, 2F). LC-MS: method A, RT=2.01 min, MS (ESI) m/z: 225.0 (boronic acid)$^+$.

Intermediate I-2

2-(methoxymethyl)-7-methyl-5-(4,4,5,5-tetramethyl-1,3,2-dioxaborolan-2-yl)quinoxaline

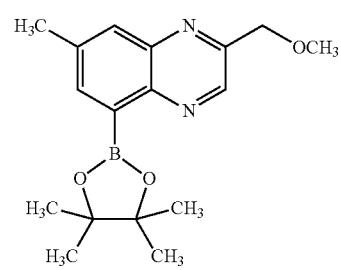

Intermediate I-2A: 1-diazo-3-methoxypropan-2-one

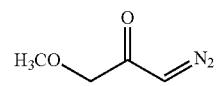

To 2-methoxyacetyl chloride (2.4 g, 22.12 mmol) in MeCN (40 mL) cooled with ice-bath was added (diazomethyl)trimethylsilane 2.0 M in diethyl ether (19.35 mL, 38.7 mmol). The mixture was allowed to stir at room temperature overnight. Solvent was removed under reduced pressure. The crude product was purified by flash chromatography (loading in chloroform, 0% to 50% EtOAc in hexane over 18 min using a 40 g silica gel cartridge). The desired fractions were combined and concentrated (bath temp below 35° C.) to yield Intermediate I-2A (1.82 g, 15.95 mmol, 72.1% yield) as a yellow liquid. $^1$H NMR (500 MHz, chloroform-d) δ 5.73 (br. s., 1H), 3.97 (br. s., 2H), 3.43 (s, 3H); LC-MS: method A, RT=0.43 min, MS (ESI) m/z: 137.0 (M+Na)$^+$.

Intermediate I-2B: 1-bromo-3-methoxypropan-2-one

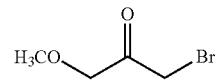

To Intermediate I-2A (1.6 g, 14.02 mmol) in diethyl ether (20 mL) at 0° C. was added aqueous HBr 48% (2.380 mL, 21.03 mmol) dropwise. After stirring at 0° C. for 5 min and at room temperature for 10 min, the reaction mixture was diluted with EtOAc, washed with water, saturated sodium bicarbonate (2×) and brine. The organic layer was dried over sodium sulfate, concentrated (keep bath temp below 30° C.) to give Intermediate I-2B (1.5 g, 8.98 mmol, 64.1% yield) as a slightly yellow liquid. $^1$H NMR indicated >92% purity. The compound was used immediately for the next step without further purification. $^1$H NMR (500 MHz, chloroform-d) δ 4.24 (s, 2H), 4.03 (s, 2H), 3.45 (s, 3H), consistent with literature report (J. Org. Chem. 1981, 217).

Intermediate I-2C: Tert-Butyl (2-bromo-4-methyl-6-nitrophenyl)(3-methoxy-2-oxopropyl)carbamate

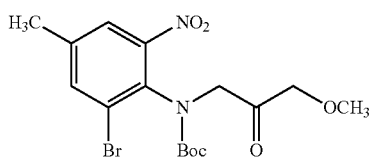

(I-2C)

To Intermediate I-1B (1.98 g, 5.98 mmol) in DMF (20 mL) at 0° C. was added Cs$_2$CO$_3$ (3.41 g, 10.46 mmol). The brown solution was stirred at 0° C. for 10 min, followed by addition of Intermediate I-2B (1.498 g, 8.97 mmol) in acetonitrile (5.0 mL). The brown solution turned yellow. The mixture was stirred at 0° C. for 15 min., diluted with EtOAc, washed with water, brine, dried over sodium sulfate and concentrated. The crude product was purified by flash chromatography (loading in chloroform, 0% to 60% EtOAc in hexane over 18 min using a 80 g silica gel cartridge). The desired fractions were combined and concentrated to yield Intermediate I-2C (2.4 g, 5.75 mmol, 96% yield) as a yellow oil. $^1$H NMR indicated presence of two rotamers. $^1$H NMR (500 MHz, chloroform-d) δ 7.70-7.65 (m, 2H), 4.55 (d, J=17.9 Hz, 1H), 4.18 (d, J=17.9 Hz, 1H), 4.32 and 4.14 (d, J=1.4 Hz, 2H), 3.44 and 3.40 (s, 3H), 2.45 and 2.40 (s, 3H), 1.49 and 1.35 (s, 9H); LC-MS: method A, RT=1.89 min, MS (ESI) m/z: 317 and 319 (M-Boc)$^+$.

Intermediate I-2D 6-bromo-3-hydroxy-3-(methoxymethyl)-8-methyl-1-oxo-1,3,4,5-tetrahydrobenzo[c][1,2,5]oxadiazepin-1-ium

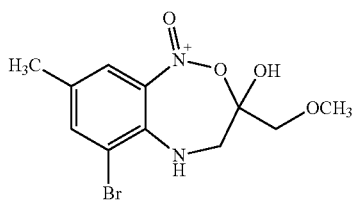

(I-2D)

To Intermediate I-2C (1.67 g, 4.00 mmol) in ethyl acetate (10 mL) was added 4.0 N HCl in dioxane (10.01 mL, 40.0 mmol) and the mixture was stirred at room temperature for 20 min. Solvent was removed under vacuum, chased with EtOAc once to give Intermediate I-2D (1.25 g, 99%) as a yellow oil. $^1$H NMR (400 MHz chloroform-d) δ 7.75-7.66 (m, 2H), 4.13-3.98 (m, 1H), 3.78-3.56 (m, 3H), 3.50 and 3.44 (m, 3H), 2.39 (s, 3H); LC-MS: method A, RT=1.47 min, MS (ESI) m/z: 317.0 and 319.0 (M+H)$^+$.

Intermediate I-2E:
5-bromo-2-(methoxymethyl)-7-methylquinoxaline

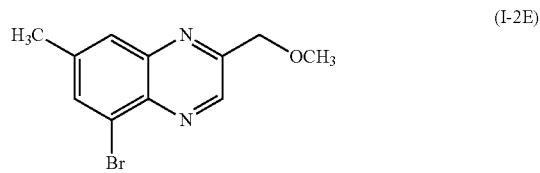

(I-2E)

Intermediate I-2D (1.25 g, 3.9 mmol) was dissolved in THF (30 mL). Concentrated HCl (0.986 mL, 12.01 mmol) was added, followed by tin(II) chloride dihydrate (3.61 g, 16.01 mmol). The mixture was placed and stirred in an oil bath pre-heated at 40° C. for 4.0 h. The reaction mixture was diluted with EtOAc/water, The organic phase was neutralized with saturated sodium bicarbonate and stirred at room temperature for 15 min, the precipitate was removed by filtration with a pad of wet celite. The filtrate was collected. The organic layer was washed with brine, dried over sodium sulfate and concentrated. The crude product was purified by flash chromatography (loading in chloroform, 0% to 60% EtOAc in hexane over 20 min using a 120 g silica gel cartridge). The desired fractions were combined and concentrated to yield Intermediate I-2D (0.57 g, 1.920 mmol, 48.0% yield) as a brown solid: $^1$H NMR (400 MHz, chloroform-d) δ 9.03 (s, 1H), 7.95 (d, J=1.5 Hz, 1H), 7.84 (dd, J=1.8, 1.1 Hz, 1H), 4.84 (s, 2H), 3.56 (s, 3H), 2.60 (s, 3H); Intermediate I-2D was contaminated with ca 10% of a side product 5-bromo-2,7-dimethylquinoxaline.

Intermediate I-2

A mixture of Intermediate I-2E (900 mg, 3.37 mmol), 4,4,4',4',5,5,5',5'-octamethyl-2,2'-bi(1,3,2-dioxaborolane) (1369 mg, 5.39 mmol), potassium acetate (661 mg, 6.74 mmol) and [1,1'-bis(diphenylphosphino)ferrocene]dichloropalladium (II) complex with dichloromethane (1:1) (110 mg, 0.135 mmol) in dioxane (15 mL) was degassed by bubbling argon for 10 min. The reaction vial was sealed and heated in microwave reactor at 130° C. for 30 min. The mixture was diluted with EtOAc/water, insoluble material was removed by filtration. The filtrate was extracted with EtOAc, washed with brine and dried over sodium sulfate, concentrated. The crude product was purified by flash chromatography (loading in chloroform, 0% to 20% dichloromethane in MeOH over 15 min using a 40 g silica gel cartridge). The desired fractions were combined and concentrated and further purified by prep HPLC (method A, 10-80% B in 8 mins; with a flow rate of 40 mL/min). The desired fractions were placed in a SpeedVac overnight to remove solvent. The material was dissolved in EtOAc, washed with diluted saturated sodium bicarbonate (to remove TFA), brine, dried over sodium sulfate, concentrated and lyophilized to give Intermediate I-2 (360 mg, 1.550 mmol, 46% yield) as a slightly colored solid. LC-MS: method A, RT=1.73 min, MS (ESI) m/z: 233.1 boronic acid (M+H)+.

Intermediate I-9

(2-methoxy-7-methylquinoxalin-5-yl)boronic acid

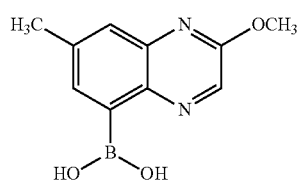
(I-9)

Intermediate I-9A:
5-bromo-2-methoxy-7-methylquinoxaline

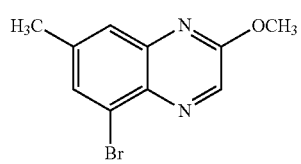
(I-9A)

To Intermediate I-1G (3.13 g, 10.83 mmol) dissolved in THF (20 mL) and MeOH (15 mL) at room temperature was added 4.3 M sodium methoxide in MeOH (7.55 mL, 32.5 mmol). The reaction mixture was stirred at room temperature over night. Methanol was removed under vacuum. The reaction mixture was diluted with EtOAc, quenched with 0.5 N HCl (30.0 mL). The organic layer was washed with saturated sodium bicarbonate, brine, dried and concentrated to give Intermediate I-9A (2.7 g, 10.67 mmol, 99% yield) as a slightly yellow solid. $^1$H NMR (500 MHz, chloroform-d) δ 8.48 (s, 1H), 7.72 (d, J=1.7 Hz, 1H), 7.60 (dd, J=1.8, 1.0 Hz, 1H), 4.10 (s, 3H), 2.53 (s, 3H); LC-MS: Method A, 30 to 100% B. RT=1.71 min, MS (ESI) m/z: 253.0 and 255.0 (M+H)+.

Intermediate I-9

A mixture of Intermediate I-9A (700 mg, 2.77 mmol), 4,4,4',4',5,5,5',5'-octamethyl-2,2'-bi(1,3,2-dioxaborolane) (1053 mg, 4.15 mmol), potassium acetate (679 mg, 6.91 mmol) and [1,1'-bis(diphenylphosphino)ferrocene]dichloropalladium (II) complex with dichloromethane (1:1) (113 mg, 0.138 mmol) in dioxane (14 mL) was degassed by bubbling argon for 5 min. It was then heated at 130° C. for 40 min. The reaction mixture was mixed with EtOAc/water and stirred at room temperature for 15 min. The insoluble material was removed by filtration through a pad of wet celite. The organic layer was washed with brine, dried over sodium sulfate and concentrated. The crude product was purified by flash chromatography (loading in chloroform, 5% to 100% EtOAc in hexane over 15 min using a 80 g silica gel cartridge). The desired fractions were combined, concentrated and lyophilized to yield to yield Intermediate I-9 (362 mg, 1.659 mmol, 60% yield) as a solid. $^1$H NMR (500 MHz, methanol-d$_4$) δ 8.41 (s, 1H), 7.69 (br. s., 1H), 7.49 (br. s., 1H), 4.10 (s, 3H), 2.56 (s, 3H). LC-MS: method H, RT=0.83 min, MS (ESI) m/z: 219.1 (M+H)+.

Intermediate I-10

5-bromo-2-(2-(difluoromethoxy)-7-methylquinoxalin-5-yl)thiazole

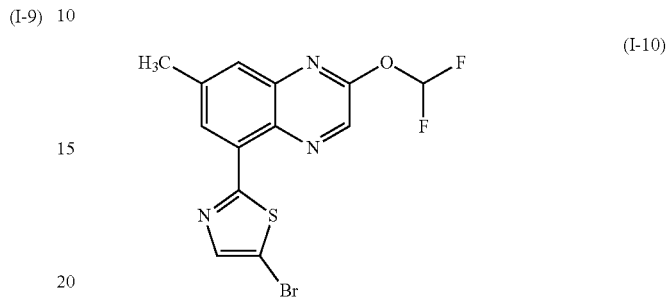
(I-10)

Intermediate I-10A: 2-(2-(difluoromethoxy)-7-methylquinoxalin-5-yl)thiazole

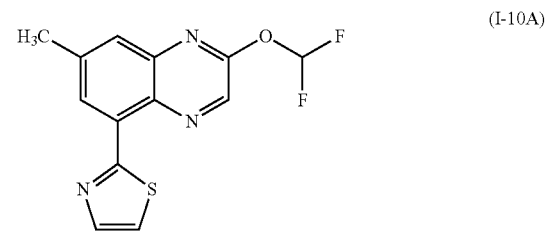 [SMILES: Cc1cc(-c2nccs2)c2ncc(OC(F)F)nc2c1]
(I-10A)

In a microwave tube to a degassed solution of Intermediate I-1G (0.200 g, 0.692 mmol), 2-(tributylstannyl)thiazole (0.259 g, 0.692 mmol) and potassium acetate (0.136 g, 1.384 mmol) in dioxane (10 mL) at room temperature was added Pd(Ph$_3$)$_4$ (0.040 g, 0.035 mmol). The reaction mixture was then heated at 120° C. for 2 hours. The reaction mixture was diluted with water and EtOAc. The layers were separated and the organic layer was washed with 1 N HCl, washed with brine, dried with sodium sulfate, and concentrated under reduced pressure to yield a yellow solid. The reaction mixture was purified on ISCO using a 0-100% gradient of EtOAc in hexanes on a 40 g column to yield Intermediate I-10A (0.126 g, 0.430 mmol, 62.1% yield) as a pale yellow solid. $^1$H NMR (400 MHz, CHLOROFORM-d) δ 8.68-8.64 (m, 2H), 8.01 (d, J=3.3 Hz, 1H), 7.86-7.45 (m, 3H), 2.65 (s, 3H). LC-MS: method H, RT=0.91 min, MS (ESI) m/z: 294.9 (M+H)+.

Intermediate I-10

Intermediate I-10A (0.126 g, 0.430 mmol) and sodium acetate (0.070 g, 0.859 mmol) were dissolved in AcOH (15 mL). Bromine (0.033 mL, 0.644 mmol) was added dropwise and the reaction mixture was allowed to stir at room temperature for 2.5 h. The reaction mixture was concentrated and the residue was redissolved in EtOAc and water. The solution was neutralized by addition of saturated aqueous sodium carbonate. The layers were separated and the organic layer was washed with water, washed with brine, dried with sodium sulfate, and concentrated under reduced pressure. This compound was used without further purification. ¹H NMR (400 MHz, CHLOROFORM-d) δ 8.64 (s, 1H), 8.60 (d, J=2.0 Hz, ¹H), 7.88 (s, 1H), 7.83-7.44 (m, 2H), 2.65 (s, 3H). LC-MS: method H, RT=1.30 min, MS (ESI) m/z: 371.9 (M+H)$^+$.

Intermediate I-11

2-(2-methoxy-7-methylquinoxalin-5-yl)thiazole

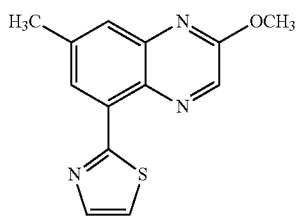

(I-11)

Intermediate I-10A (0.100 g, 0.341 mmol) was dissolved in MeOH (2.73 mL), THF (0.682 mL), and 1 N NaOH (1.023 mL, 1.023 mmol). The reaction mixture was allowed to stir at room temperature for 18 h. The reaction mixture was diluted with EtOAc and washed with water, washed with brine, dried with sodium sulfate, filtered, and concentrated under reduced pressure to yield Intermediate I-11 (0.088 g, 3.41 mmol, 100%). ¹H NMR (400 MHz, CHLOROFORM-d) δ 8.53 (s, 1H), 8.51 (d, J=2.0 Hz, 1H), 7.99 (d, J=3.3 Hz, 1H), 7.70 (dd, J=1.9, 0.9 Hz, 1H), 7.53 (d, J=3.3 Hz, 1H), 4.12 (s, 3H), 2.62 (s, 3H). LC-MS: method H, RT=1.05 min, MS (ESI) m/z: 258.0 (M+H)$^+$.

Intermediate I-12

2-methoxy-7-methylquinoxaline-5-carbothioamide

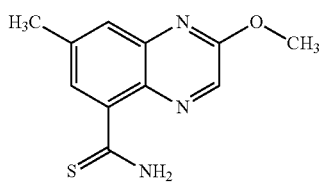

(I-12)

Intermediate I-12A: 2-methoxy-7-methylquinoxaline-5-carbonitrile

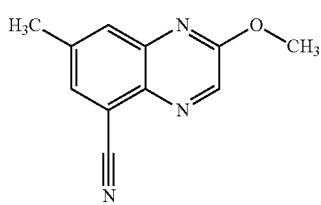

(I-12A)

Intermediate I-9A (0.458 g, 1.810 mmol) and copper(I) cyanide (0.600 g, 6.70 mmol) were dissolved in DMF (18.10 mL) and heated to reflux for 20 hours. The reaction mixture was cooled to ambient temperature. The reaction mixture was diluted with saturated NaHCO₃ and extracted with EtOAc. The organic layer was further washed with water then brine, dried (Na₂SO₄), filtered, and concentrated in vacuo. The crude material was purified by column chromatography (ISCO, 12 g silica gel column, 17 minute gradient from 0 to 1000/EtOAc in hexanes) to give Intermediate I-12A (247 mg, 1.24 mmol, 68.5%) as a white solid: ¹H NMR (400 MHz, CHLOROFORM-d) δ 8.55 (s, 1H), 7.86 (d, J=0.8 Hz, 1H), 7.78 (s, 1H), 4.11 (s, 3H), 2.58 (s, 3H); LC-MS: Method H, RT=0.92 min, MS (ESI) m/z: 200.1 (M+H)$^+$.

Intermediate I-12

Intermediate I-12A (0.247 g, 1.240 mmol), sodium hydrosulfide (1.043 g, 18.60 mmol), and magnesium chloride (1.771 g, 18.60 mmol) were dissolved in DMF (12.40 mL) and stirred for 18 hours. The reaction mixture was diluted with water, which formed copious amounts of precipitates. The reaction mixture was extracted thrice with EtOAc. The combined organic layers were washed with brine, dried (Na₂SO₄), filtered, and concentrated in vacuo. The solid was sonicated with DCM then filtered. The resulting solution was concentrated in vacuo to give Intermediate I-12 (111 mg, 0.476 mmol, 38.4%) as an orange solid: ¹H NMR (400 MHz, CHLOROFORM-d) δ 11.86 (br. s., 1H), 9.04 (d, J=2.0 Hz, 1H), 8.40 (s, 1H), 8.32 (br. s., 1H), 7.82 (dd, J=1.9, 0.9 Hz, 1H), 4.11 (s, 3H), 2.61 (s, 3H); LC-MS: Method H, RT=0.88 min. MS (ESI) m/z: 234.0 (M+H)$^+$.

Intermediate I-13

5-bromo-2-(2-(methoxymethyl)-7-methylquinoxalin-5-yl)thiazole

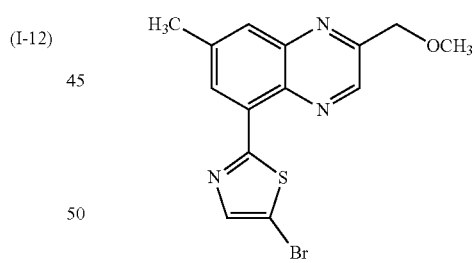

(I-13)

Intermediate I-13A: (5-bromo-7-methylquinoxalin-2-yl)methanol

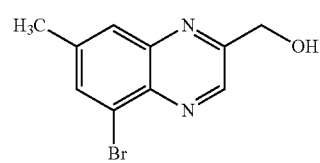

(I-13A)

NaBH$_4$ (135 mg, 3.56 mmol) and calcium chloride (197 mg, 1.779 mmol) were dissolved in THF (5270 µl). A solution of Intermediate I-8 (500 mg, 1.779 mmol) in THF (1318 µl) was added dropwise, and the reaction mixture was allowed to stir at room temperature for 18 h. The reaction mixture was diluted with EtOAc, washed with water, washed with brine, dried with sodium sulfate, filtered, and concentrated under reduced pressure. The crude material was purified by column chromatography (ISCO, 40 g silica gel column, 19 minute gradient from 0 to 100% EtOAc in hexanes) to yield Intermediate I-13A (0.263 g, 1.04 mmol, 58%) as a yellow solid. $^1$H NMR (500 MHz, CHLOROFORM-d) δ 8.85 (s, 1H), 7.92 (d, J=1.7 Hz, 1H), 7.79 (dd, J=1.7, 1.1 Hz, 1H), 5.04 (s, 2H), 3.73 (br. s., 1H), 2.58 (s, 3H). LC-MS: method H, RT=0.93 min, MS (ESI) m/z: 253.1 (M+H)$^+$.

Intermediate I-13B:
(5-bromo-7-methylquinoxalin-2-yl)methyl methanesulfonate

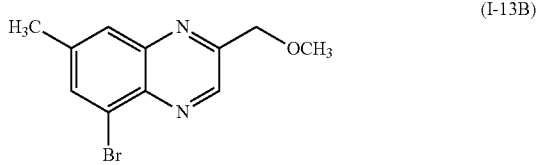

(I-13B)

Intermediate I-13A (262.5 mg, 1.037 mmol) and TEA (0.434 mL, 3.11 mmol) were dissolved in DCM (20 mL) and methanesulfonic anhydride (217 mg, 1.245 mmol) was added. The reaction mixture was stirred at room temperature for 1 h. The reaction mixture was diluted with DCM and washed with saturated NaHCO$_3$, dried with sodium sulfate, filtered, and concentrated in vacuo to yield Intermediate I-13B (0.343 g, 1.04 mmol, 100%6) as an orange solid. The material will be used crude in the next step. LC-MS: method H, RT=1.00 min, MS (ESI) m/z: 331.0 (M+H)$'$.

Intermediate I-13C:
5-bromo-2-(methoxymethyl)-7-methylquinoxaline

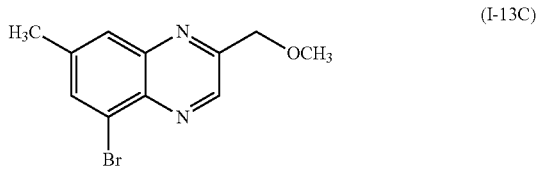

(I-13C)

Intermediate I-13B (343 mg, 1.036 mmol) was dissolved in THF (20 mL). Sodium methoxide (4143 µl, 2.071 mmol) was added, and the reaction mixture was stirred at room temperature for 18 h. The reaction mixture was partially concentrated in vacuo to remove THF, diluted with EtOAc and washed with water, washed with brine, dried with sodium sulfate, filtered, and concentrated in vacuo to yield Intermediate I-13C (0.205 g, 0.767 mmol, 74%) as an orange solid. $^1$H NMR (500 MHz, CHLOROFORM-d) δ 9.02 (s, 1H), 7.94 (d, J=1.9 Hz, 1H), 7.83 (dd, J=1.8, 1.0 Hz, 1H), 4.82 (s, 2H), 3.55 (s, 3H), 2.59 (s, 3H). LC-MS: method H, RT=1.08 min, MS (ESI) m/z: 267.1 (M+H)$^+$.

Intermediate I-13D: 2-(2-(methoxymethyl)-7-methylquinoxalin-5-yl)thiazole

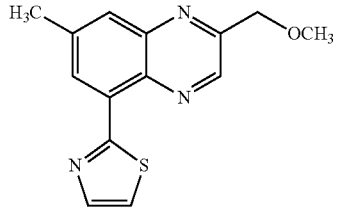

(I-13D)

Intermediate I-13C (205 mg, 0.767 mmol), 2-tributylstannylthiazole (241 µl, 0.767 mmol), and potassium acetate (151 mg, 1.535 mmol) were dissolved in dioxane (20 mL) and degassed by bubbling with argon for 15 minutes. Pd(Ph$_3$)$_4$ (44.3 mg, 0.038 mmol) was added and the reaction mixture was heated to 120° C. in the microwave for 2 hours. The reaction mixture was diluted with EtOAc, washed with water, washed with 1 N HCl, washed with brine, dried sodium sulfate, filtered, and concentrated in vacuo. The crude material was purified by column chromatography (ISCO, 40 g silica gel column, 19 minute gradient from 0 to 100% EtOAc in hexanes) to yield Intermediate I-13D (0.125 g, 0.461 mmol, 60%) as a yellow solid. $^1$H NMR (400 MHz, CHLOROFORM-d) δ 9.09 (s, 1H), 8.76 (d, J=1.8 Hz, 1H), 8.04 (d, J=3.3 Hz, 1H), 7.93 (s, 1H), 7.59 (d, J=3.3 Hz, 1H), 486 (s, 2H), 3.59 (s, 3H), 2.70 (s, 3H). LC-MS: method H, RT=1.12 min, MS (ESI) m/z: 272.2 (M+H)$^+$.

Intermediate I-13

Intermediate I-13D (125 mg, 0.461 mmol) and sodium acetate (76 mg, 0.921 mmol) were dissolved in AcOH (14 mL). A stock solution of bromine (35.6 µl, 0.691 mmol) was prepared in AcOH (1.4 mL) and added to the starting material solution. The reaction mixture was allowed to stir at room temperature for 1 h. The reaction mixture was concentrated in vacuo. The residue was dissolved in EtOAc and washed with saturated NaHCO$_3$, washed with water, washed with brine, dried with sodium sulfate, filtered, and concentrated in vacuo to yield Intermediate I-13 (0.167 g, 0.477 mmol, 100%) as a yellow solid. $^1$H NMR (400 MHz, CHLOROFORM-d) δ 9.06 (s, 1H), 8.70 (d, J=1.8 Hz, 1H), 7.95-7.93 (m, 1H), 7.92-7.89 (m, 1H), 4.86 (s, 2H), 3.60 (s, 3H), 2.69 (s, 3H). LC-MS: method H, RT=1.34 min, MS (ESI) m/z: 350.1 (M+H)$^+$.

Intermediate I-18

5-bromo-2-(2-(difluoromethoxy)-7-methylquinoxalin-5-yl)-4-methylthiazole

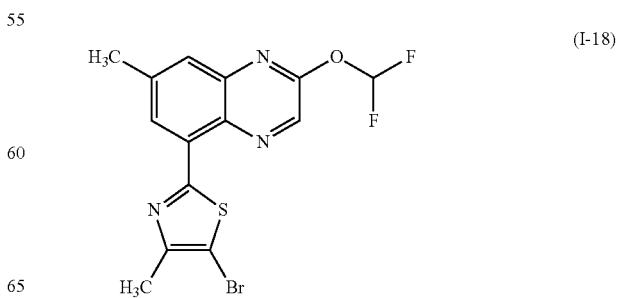

(I-18)

Intermediate I-18A: 2-(2-(difluoromethoxy)-7-methylquinoxalin-5-yl)-4-methylthiazole

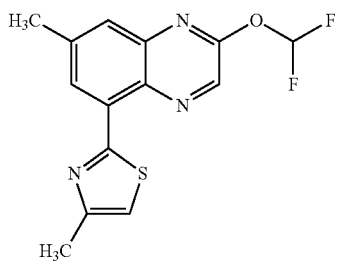

(18A)

Intermediate I-1 (18.4 mg, 0.055 mmol) and 2-bromo-4-methylthiazole (14.62 mg, 0.082 mmol) were dissolved in DMF (547 μL). PdCl$_2$(dppf)-CH$_2$Cl$_2$ (2.68 mg, 3.28 μmol) was added and the reaction mixture was degassed by bubbling with argon for 15 minutes. Sodium carbonate (2 M, 32.8 μL, 0.066 mmol) was added and the reaction mixture was degassed for 5 minutes, then sealed and heated to 90° C. in the microwave for 30 minutes. More 2-bromo-4-methylthiazole (14.62 mg, 0.082 mmol), Sodium carbonate (2 M, 32.8 μL, 0.066 mmol), and PdCl$_2$(dppf)-CH$_2$Cl$_2$ (2.68 mg, 3.28 μmol) were added and the reaction mixture was heated to 100° C. in the microwave for an additional 30 minutes. The reaction mixture was diluted with MeOH, filtered, and purified by preparative HPLC (Method A, 30 to 100% B in 18 minutes) to give Intermediate I-18A (14.2 mg, 0.046 mmol, 84%) as a red solid: $^1$H NMR (400 MHz, CHLOROFORM-d) δ 8.69-8.63 (m, 2H), 7.93-7.89 (m, 1H), 7.84-7.45 (m, 1H), 7.36 (d, J=0.8 Hz, 1H), 2.70 (d, J=1.0 Hz 3H), 2.67 (s, 3H); LC-MS: Method H, RT=1.15 min, MS (ESI) m/z: 308.1 (M+H)$^+$.

Intermediate I-18

Intermediate I-18A (14.2 mg, 0.046 mmol) and sodium acetate (7.58 mg, 0.092 mmol) were dissolved in AcOH (1400 μL). A stock solution of bromine (3.57 μL, 0.069 mmol) was prepared in AcOH (140 μL) and added to the starting material solution and the reaction mixture was stirred for 1 hour. The reaction mixture was concentrated in vacuo. The residue was diluted with EtOAc and washed with saturated Sodium carbonate, water, then brine, dried (Na$_2$SO$_4$), filtered, and concentrated in vacuo to give I-18 (13.2 mg, 0.034 mmol, 74%) as a yellow solid: $^1$H NMR (400 MHz, CHLOROFORM-d) δ 8.63 (s, 1H), 8.58 (d, J=1.8 Hz, 1H), 7.84-7.44 (m, 2H), 2.64 (s, 3H), 2.52 (s, 3H) LC-MS: Method H, The compound did not ionize.

Intermediate I-19

4-bromo-2-(2-(difluoromethoxy)-7-methylquinoxalin-5-yl)thiazole

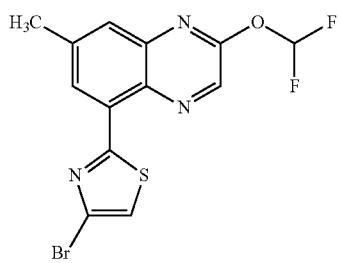

(I-19)

Intermediate I-1G (50 mg, 0.173 mmol), 4-bromo-2-tributylstannyl)thiazole (59.6 μL, 0.173 mmol), and potassium acetate (34.0 mg, 0.346 mmol) were dissolved in dioxane (2507 μL) and degassed by bubbling with argon for 15 minutes. Palladium tetrakistriphenylphosphine (9.99 mg, 8.65 μmol) was added and the reaction mixture was sealed and heated to 120° C. in the microwave for 2 hours. More palladium tetrakistriphenylphosphine (9.99 mg, 8.65 μmol) was added and the reaction mixture was heated for an additional 1 hour in the microwave at 120° C. The reaction mixture was diluted with EtOAc, washed with water, 1 N HCl, then brine, dried (Na$_2$SO$_4$), filtered, and concentrated in vacuo. The crude material was purified by column chromatography (ISCO, 12 g silica gel column, 17 minute gradient from 0 to 100% DCM in hexanes) then repurified by preparative HPLC (Method A, 30 to 100%/c B in 20 minutes) to give Intermediate I-19 (9 mg, 0.024 mmol, 14%) as a light yellow solid: $^1$H NMR (400 MHz, CHLOROFORM-d) δ 8.67 (d, J=1.5 Hz, 1H), 8.64 (s, 1H), 7.84-7.46 (m, 2H), 7.43 (s, 1H), 2.65 (s, 3H); LC-MS: Method H, RT=1.25 min, MS (ESI) m/z: 372/374 (M+H)$^+$.

Intermediate I-23

2-(2-methoxy-7-methylquinoxalin-5-yl)thiazole-5-carboxylic acid

Intermediate I-23A: methyl

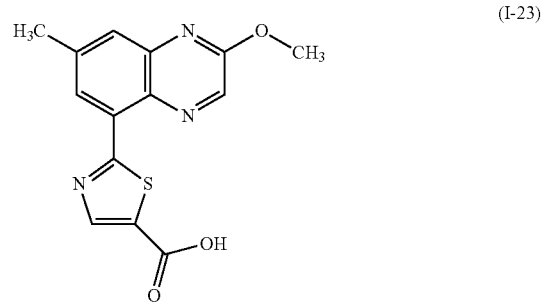

(I-23)

2-(2-methoxy-7-methylquinoxalin-5-yl)thiazole-5-carboxylate 2-(2-(difluoromethoxy)-7-methylquinoxalin-5-yl)thiazole-4-carboxylate

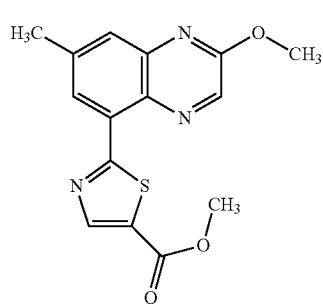
(I-23A)

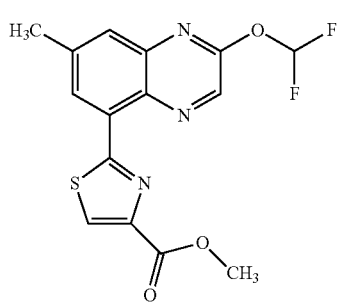
(I-24A)

To a stirred solution of Intermediate I-12 (1.0 g, 4.29 mmol) in DMF (10 mL) was added ethyl 2-chloro-3-oxo-propanoate (0.807 g, 5.36 mmol) and the reaction mixture was heated to 90° C. for 2 hours. The reaction mixture was diluted with EtOAc and washed with water, then brine, dried (Na$_2$SO$_4$), filtered, and concentrated in vacuo to give Intermediate I-23A (500 mg, 1.586 mmol, 37%) as a white solid: LC-MS: Method H, RT=1.56 min, MS (ESI) m/z: 316.4 (M+H)$^+$.

Intermediate I-23

Intermediate I-23A (500 mg, 1.586 mmol) was dissolved in THF (15 mL) and water (5 mL). LiOH was added (152 mg, 6.344 mmol) was added and the reaction mixture stirred for 4 hours. The reaction mixture was concentrated in vacuo to remove the organic layer. The aqueous layer was then washed with EtOAc, acidified with 1.5 N HCl, and the solid collected by suction filtration to give Intermediate I-23 (340 mg, 0.869 mmol, 54.8%): $^1$H NMR (300 MHz, DMSO-d$_6$) δ 8.76 (s, 1H), 8.52 (s, 1H), 8.51 (2, 1H), 7.83 (t, J=0.9 Hz, 1H), 4.08 (s, 3H), 2.61 (s, 3H), one peak buried under DMSO peak: LC-MS: Method G, RT=1.6 min, MS (ESI) m/z: 301.4 (M+H)$^+$.

Intermediate I-24

2-(2-(difluoromethoxy)-7-methylquinoxalin-5-yl)thiazole-4-carboxylic acid

Intermediate I-24A: methyl

Intermediate I-1 (880 mg, 3.46 mmol), methyl 2-bromothiazole-4-carboxylate (769 mg, 3.46 mmol), and potassium acetate (850 mg, 8.66 mmol) were dissolved in dioxane (10 mL). Palladium tetrakistriphenylphosphine (320 mg, 0.277 mmol) was added and the reaction mixture was heated to 125° C. for 2 hours in the microwave. The reaction mixture was diluted with EtOAc, washed with water, then brine, dried (Na$_2$SO$_4$), filtered, and concentrated in vacuo. The crude material was purified by column chromatography (10% EtOAc in petroleum ether) to give Intermediate I-24A (300 mg, 0.649 mmol, 18.7%): LC-MS: Method G, RT=2.07 min. MS (ESI) m/z: 352.2 (M+H)$^+$.

Intermediate I-24

To a solution of Intermediate I-24A (300 mg, 0.649 mmol) in THF (10 mL) and water (3 mL) was added lithium hydroxide monohydrate (18.7 mg, 0.779 mmol) at −10° C. for 2 hours. The reaction mixture was warmed to 0° C. for 12 hours. The reaction mixture was concentrated in vacuo. The crude material was diluted with water, acidified with citric acid then extracted with EtOAc. The organic layer was dried (Na$_2$SO$_4$), filtered, and concentrated in vacuo to give Intermediate I-24 (175 mg, 0.498 mmol, 77%) as an off-white solid: $^1$H NMR (400 MHz, DMSO-d$_6$) δ 8.98 (s, 1H), 8.63 (m, 2H), 7.91 (m, 2H), 2.68 (s, 3H); LC-MS: Method G, RT=1.89 min, MS (ESI) nm/z: 338.0 (M+H)$^+$.

Example 1

5-(2-methoxy-7-methylquinoxalin-5-yl)-3-phenylisoxazole

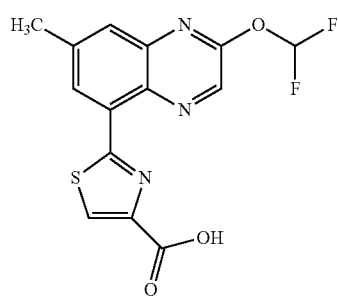
(I-24)

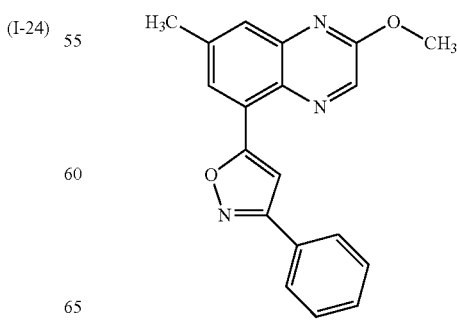
(1)

Intermediate 1A:
5-iodo-2-methoxy-7-methylquinoxaline

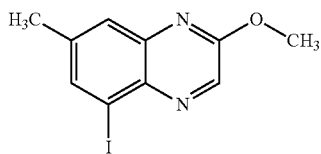
(1A)

5-iodo-7-methylquinoxalin-2(1H)-one (500 mg, 1.748 mmol) was suspended in toluene (11.7 mL). Silver oxide (1013 mg, 4.37 mmol) then iodomethane (153 μL, 2.447 mmol) were added. The reaction mixture was allowed to stir at ambient temperature for 18 hours. The reaction mixture was diluted with EtOAc and filtered through a micron filter to remove the silver oxide. The residue was concentrated in vacuo and purified by column chromatography (ISCO, 40 g silica gel column, 19 minute gradient from 0 to 100% EtOAc in hexanes) to give Intermediate 1A (81 mg, 0.27 mmol, 15.4%) as a white solid: $^1$H NMR (400 MHz, chloroform-d) δ 8.42 (s, 1H), 8.00 (d, J=1.5 Hz, 1H), 7.62 (dd, J=1.8, 0.8 Hz, 1H), 4.10 (s, 3H), 2.51 (s, 3H); LC-MS: Method H, RT=1.09 min, MS (ESI) m/z: 301.1 (M+H)$^+$.

Example 1

Intermediate 1A (15 mg, 0.050 mmol) and (3-phenylisoxazol-5-yl)boronic acid (14.17 mg, 0.075 mmol) were dissolved in DMF (500 μL). PdCl$_2$(dppf)-CH$_2$Cl$_2$ (2.449 mg, 3.00 μmol) was added and the reaction mixture was degassed by bubbling with argon for 15 minutes. Sodium carbonate (2 M, 30.0 μL, 0.060 mmol) was added and the reaction mixture was degassed for 5 minutes, then sealed and heated to 90° C. in the microwave for 30 minutes. The reaction mixture was diluted with DMF, filtered, and purified by preparative HPLC (Method D, 35 to 100% B in 10 minutes). The material was repurified by preparative HPLC (Method D, 50 to 85% B in 20 minutes) to give Example 1 (4.1 mg, 0.013 mmol, 25.5%): $^1$H NMR (500 MHz, METHANOL-d$_4$) δ 8.54 (s, 1H), 8.09 (d, J=1.7 Hz, 1H), 7.95-7.89 (m, 2H), 7.81 (s, 1H), 7.77-7.73 (m, 1H), 7.55-7.46 (m, 3H), 4.13 (s, 3H), 2.63 (s, 3H); LC-MS: Method H, RT=1.33 min. MS (ESI) m/z: 318 (M+H)$^+$ Analytical HPLC Method B: 98.5% purity.

Example 2

2-(difluoromethoxy)-7-methyl-5-(1-phenyl-1H-pyrazol-4-yl)quinoxaline

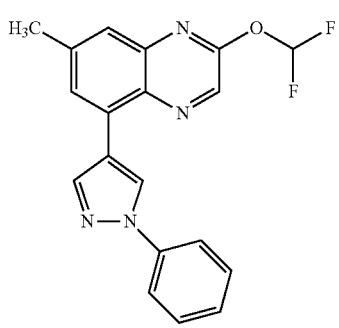
(2)

Intermediate I-1 (15 mg, 0.045 mmol) and 4-bromo-1-phenyl-1H-pyrazole (14.93 mg, 0.067 mmol) were dissolved in DMF (446 μL). PdCl$_2$(dppf)-CH$_2$Cl$_2$ (2.187 mg, 2.68 μmol) was added and the reaction mixture was degassed by bubbling with argon for 15 minutes. Sodium carbonate (2 M, 26.8 μL, 0.054 mmol) was added and the reaction mixture was degassed for 5 minutes, then sealed and heated to 90° C. in the microwave for 30 minutes. The reaction mixture was diluted with DMF, filtered, and purified by preparative HPLC (Method D, 40 to 75% B in 20 minutes) to give Example 2 (3.0 mg, 0.00823 mmol, 18.4%): $^1$H NMR (500 MHz, METHANOL-d$_4$) δ 8.89 (s, 1H), 8.61 (s, 1H), 8.34 (s, 1H), 7.86-7.75 (m, 3H), 7.70-7.56 (m, 2H), 7.55-7.48 (m, 2H), 7.40-7.33 (m, 1H), 2.62 (s, 3H); LC-MS: Method H, RT=1.18 min, MS (ESI) m/z: 352.9 (M+H)$^+$ Analytical HPLC Method B: 96.6%6 purity.

Example 3

5-(2-(difluoromethoxy)-7-methylquinoxalin-5-yl)-2-phenylthiazole

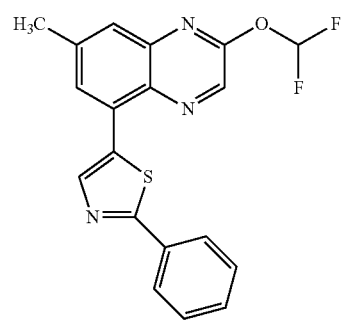
(3)

Intermediate I-1 (17.2 mg, 0.051 mmol) and 5-bromo-2-phenylthiazole (18.43 mg, 0.077 mmol) were dissolved in DMF (512 μL). PdCl$_2$(dppf)-CH$_2$Cl$_2$ (2.507 mg, 3.07 μmol) was added and the reaction mixture was degassed by bubbling with argon for 15 minutes. Sodium carbonate (2 M, 30.7 μL, 0.061 mmol) was added and the reaction mixture was degassed for 5 minutes, then sealed and heated to 90° C. in the microwave for 30 minutes. The reaction mixture was diluted with DMF and purified by preparative HPLC (Method D, 50 to 95% B in 10 minutes) to give Example 3 (13.3 mg, 0.036 mmol, 69.7%): $^1$H NMR (500 MHz, METHANOL-d$_4$) δ 8.64 (s, 1H), 8.46 (s, 1H), 8.04-7.97 (m, 3H), 7.84-7.53 (m, 2H), 7.52-7.44 (m, 3H), 2.65 (s, 3H); LC-MS: Method H, RT=1.23 min, MS (ESI) m/z: 369.9 (M+H) Analytical HPLC Method B: 99% purity.

Example 4

2-(2-(difluoromethoxy)-7-methylquinoxalin-5-yl)-5-methylthiazole

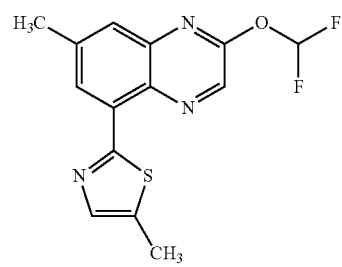
(4)

Intermediate I-1 (17.1 mg, 0.051 mmol) and 2-bromo-5-methylthiazole (13.59 mg, 0.076 mmol) were dissolved in DMF (509 μL). PdCl$_2$(dppf)-CH$_2$Cl$_2$ (2.493 mg, 3.05 μmol) was added and the reaction mixture was degassed by bubbling with argon for 15 minutes. Sodium carbonate (2 M, 30.5 μL, 0.061 mmol) was added and the reaction mixture was degassed for 5 minutes, then sealed and heated to 90° C. in the microwave for 30 minutes. The reaction mixture was diluted with DMF and purified by preparative HPLC (Method D, 45 to 85% B in 10 minutes) then repurified by preparative HPLC (Method D, 40 to 75% B in 20 minutes) to give Example 4 (2.6 mg, 0.00821 mmol, 16.1%): $^1$H NMR (500 MHz, METHANOL-d$_4$) δ 8.65 (s, 1H), 8.44 (d, J=1.7 Hz, 1H), 7.85-7.52 (m, 3H), 2.64 (s, 3H), 2.58 (s, 3H); LC-MS: Method H, RT=1.12 min, MS (ESI) m/z: 307.9 (M+H)$^+$ Analytical HPLC Method B: 97.0% purity.

Example 5

3-(2-(difluoromethoxy)-7-methylquinoxalin-5-yl)isothiazole

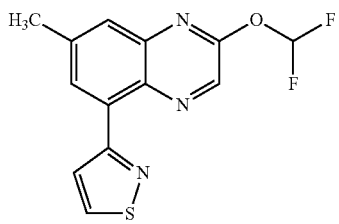

(5)

Intermediate I-1 (15 mg, 0.045 mmol) and 3-bromoisothiazole (10.98 mg, 0.067 mmol) were dissolved in DMF (446 μL). PdCl$_2$(dppf)-CH$_2$Cl$_2$ (2.187 mg, 2.68 μmol) was added and the reaction mixture was degassed by bubbling with argon for 15 minutes. Sodium carbonate (2 M, 26.8 μL, 0.054 mmol) was added and the reaction mixture was degassed for 5 minutes, then sealed and heated to 90° C. in the microwave for 30 minutes. The reaction mixture was diluted with DMF, filtered, and purified by preparative HPLC (Method D, 35 to 80% B in 10 minutes) to give Example 5 (5.0 mg, 0.017 mmol, 37.2%): $^1$H NMR (500 MHz, METHANOL-d$_4$) δ 8.89 (d, J=4.7 Hz, 1H), 8.59 (s, 1H), 8.13 (d, J=1.9 Hz, 1H), 8.10 (d, J=4.7 Hz, 1H), 7.84-7.52 (m, 2H), 2.64 (s, 3H); LC-MS: Method H, RT=1.08 min, MS (ESI) m/z: 293.9 (M+H)$^+$; Analytical HPLC Method B: 97.4% purity.

Example 6

3-(2-(2-(difluoromethoxy)-7-methylquinoxalin-5-yl)-4-methylthiazol-5-yl)phenol

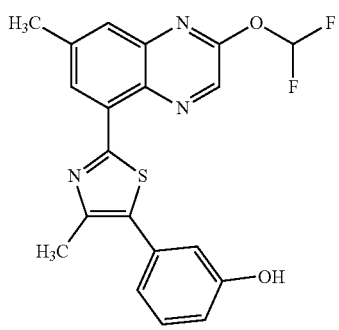

(6)

Intermediate I-18 (13.2 mg, 0.034 mmol) and (3-hydroxyphenyl)boronic acid (7.07 mg, 0.051 mmol) were dissolved in DMF (342 μL). PdCl$_2$(dppf)-CH$_2$Cl$_2$ (1.675 mg, 2.051 μmol) was added and the reaction mixture was degassed by bubbling with argon for 15 minutes. Sodium carbonate (2 M, 20.51 μL, 0.041 mmol) was added and the reaction mixture was degassed for 5 minutes, then sealed and heated to 100° C. in the microwave for 30 minutes. The compound was diluted with DMF and purified by preparative HPLC (Method D, 40 to 85% B in 10 minutes) to give Example 6 (6.8 mg, 0.017 mmol, 48.8%): $^1$H NMR (500 MHz, METHANOL-d$_4$) δ 8.66 (s, 1H), 8.54 (d, J=1.9 Hz, 1H), 7.85-7.52 (m, 2H), 7.29 (t, J=7.8 Hz, 1H), 7.06-7.00 (m, 2H), 6.85 (dt, J=8.2, 1.1 Hz, 1H), 2.67 (s, 3H), 2.60 (s, 3H); LC-MS: Method H, RT=1.16 min, MS (ESI) m/z: 400.0 (M+H)$^+$; Analytical HPLC Method B: 98.0% purity.

Example 7

5-benzyl-2-(2-(difluoromethoxy)-7-methylquinoxalin-5-yl)thiazole

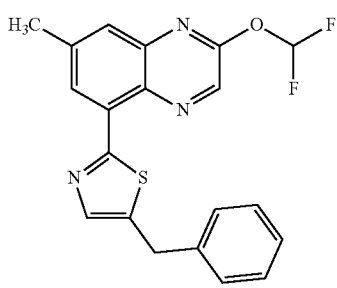

(7)

Intermediate 7A: 5-benzyl-2-bromothiazole

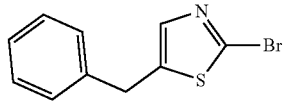

(7A)

Copper(II) bromide (49.9 mg, 0.223 mmol) was suspended in MeCN (526 μL). t-Butyl nitrite (27.3 μL, 0.230 mmol) was added and the reaction mixture was stirred for 10 minutes. The above solution was added to a suspension of 5-benzylthiazol-2-amine (25 mg, 0.131 mmol) in MeCN (788 μL) and stirred for 2 hours. The reaction mixture was diluted with EtOAc and washed twice with 1 N HCl, saturated NaHCO$_3$, then brine, dried (Na$_2$SO$_4$), filtered, and concentrated in vacuo. The crude material was purified by preparative HPLC (Method A, 30 to 100% B in 17 minutes) to give 7A (11.5 mg, 0.045 mmol, 34.4%) as a yellow solid: $^1$H NMR (400 MHz, CHLOROFORM-d) δ 7.41-7.12 (m, 6H), 4.10 (s, 2H); LC-MS: Method H, RT=1.08 min, MS (ESI) m/z: 254/256 (M+H)$^+$.

Example 7

Intermediate I-1 (15 mg, 0.045 mmol) and 7 (11.34 mg, 0.045 mmol) were dissolved in DMF (446 μL). PdCl$_2$(dppf)-

CH$_2$Cl$_2$ (2.187 mg, 2.68 µmol) was added and the reaction mixture was degassed by bubbling with argon for 15 minutes. Sodium carbonate (2 M, 26.8 µL, 0.054 mmol) was added and the reaction mixture was degassed for 5 minutes, then sealed and heated to 100° C. in the microwave for 30 minutes. The compound was diluted with DMF and purified by preparative HPLC (Method D, 50 to 90% B in 10 minutes) to give Example 7 (2.7 mg, 0.00691 mmol, 15.5%): $^1$H NMR (500 MHz, METHANOL-d$_4$) δ 8.61 (s, 1H), 8.45 (d, J=1.9 Hz, 1H), 7.82-7.49 (m, 3H), 7.36-7.28 (m, 4H), 7.27-7.22 (m, 1H), 4.25 (s, 2H), 2.63 (s, 3H); LC-MS: Method H, RT=1.22 min, MS (ESI) m/z: 383.8 (M+H)$^+$; Analytical HPLC Method B: 98.1% purity.

Example 8

2-(2-(difluoromethoxy)-7-methylquinoxalin-5 yl)-4-vinylthiazole

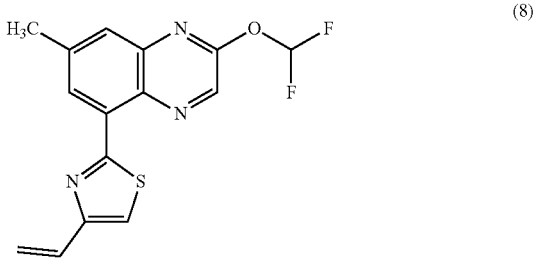 [SMILES: C=Cc1csc(-c2cc(C)cc3nc(OC(F)F)cnc23)n1]

(8)

Intermediate I-19 (9 mg, 0.024 mmol) and 2,4,6-trivinylcyclotriboroxane pyridine complex (5.82 mg, 0.024 mmol) were dissolved in DMF (242 µL). PdCl$_2$(dppf)-CH$_2$Cl$_2$ (1.185 mg, 1.451 µmol) was added and the reaction mixture was degassed by bubbling with argon for 15 minutes. Sodium carbonate (2 M, 14.51 µL, 0.029 mmol) was added and the reaction mixture was degassed for 5 minutes, then sealed and heated to 90° C. in the microwave for 30 minutes. The reaction mixture was diluted with DMF and purified by preparative HPLC (Method D, 50 to 95% B in 10 minutes) to give Example 8 (4.3 mg, 0.013 mmol, 54.9%): $^1$H NMR (500 MHz, METHANOL-d$_4$) δ 8.66 (s, 1H), 8.63 (d, J=1.7 Hz, 1H), 7.84-7.51 (m, 2H), 7.45 (s, 1H), 6.85 (dd, J=17.5, 10.9 Hz, 1H), 6.16 (dd, J=17.3, 1.4 Hz, 1H), 5.42 (dd, J=10.9, 1.5 Hz, 1H), 2.66 (s, 3H); LC-MS: Method H, RT=1.23 min, MS (ESI) m/z: 320.0 (M+H)$^+$; Analytical HPLC Method B: 98.6% purity.

Example 9

2-(2-(difluoromethoxy)-7-methylquinoxalin-5-yl)-4-methyl-5-(1H-pyrazol-5-yl)thiazole

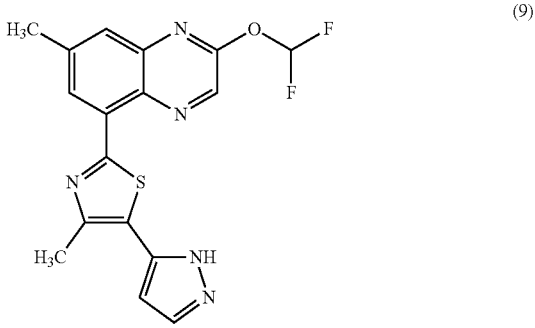 [SMILES: Cc1cc(-c2nc(C)c(-c3ccn[nH]3)s2)c2ncc(OC(F)F)nc2c1]

(9)

Intermediate I-18 (20.4 mg, 0.053 mmol) and (1H-pyrazol-5-yl)boronic acid (8.87 mg, 0.079 mmol) were dissolved in DMF (528 µL). PdCl$_2$(dppf)-CH$_2$Cl$_2$ (2.59 mg, 3.17 µmol) was added and the reaction mixture was degassed by bubbling with argon for 15 minutes. Sodium carbonate (31.7 µL, 0.063 mmol) was added and the reaction mixture was degassed for 5 minutes, then sealed and heated to 100° C. in the microwave for 30 minutes. The compound was diluted with DMF and purified by preparative HPLC (Method D, 35 to 75% B in 10 minutes) to give Example 9 (10.6 mg, 0.028 mmol, 52.7%): $^1$H NMR (500 MHz, METHANOL-d$_4$) δ 8.65 (s, 1H), 8.55 (s, 1H), 7.74 (s, 1H), 7.68 (br. s., 1H), 7.84-7.49 (m, 1H), 6.59 (br. s., 1H), 2.69 (br. s., 3H), 2.66 (s, 3H); LC-MS: Method H, RT=1.07 min, MS (ESI) m/z: 374.0 (M+H)$^+$; Analytical HPLC Method B: 98% purity.

Example 10

4-cyclopropyl-2-(2-(difluoromethoxy)-7-methylquinoxalin-5-yl)thiazole

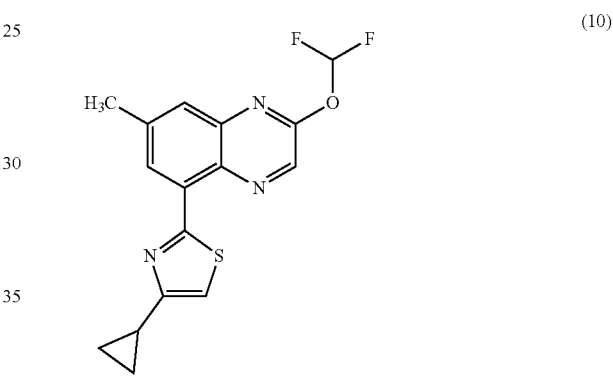

(10)

Intermediate I-19 (16.7 mg, 0.045 mmol), cyclopropylboronic acid (5.01 mg, 0.058 mmol), palladium(II) acetate (0.504 mg, 2.243 µmol), tricyclohexylphosphine (1.258 mg, 4.49 µmol), and potassium phosphate tribasic (33.3 mg, 0.157 mmol) were degassed by HIVAC/nitrogen backfill thrice. Toluene (285 µL) and water (14.24 µL) were added and the reaction mixture was degassed by bubbling 30 minutes with argon. The reaction mixture was heated to 100° C. for 18 hours. The reaction mixture was diluted with EtOAc and washed with water, then twice with saturated NaHCO$_3$, dried (Na$_2$SO$_4$), filtered, and concentrated in vacuo. The crude material was diluted with DMF, filtered, and purified by preparative HPLC (Method D, 55 to 100% B in 25 minutes) to give Example 10 (2.7 mg, 0.00794 mmol, 17.7%): $^1$H NMR (500 MHz, METHANOL-d$_4$) δ 8.64 (s, 1H), 8.52 (d, J=1.9 Hz, 1H), 7.73 (d, J=0.8 Hz, 1H), 7.85-7.50 (m, 1H), 7.11 (s, 1H), 2.65 (s, 3H), 2.22-2.13 (m, 1H), 1.04-0.97 (m, 2H), 0.98-0.91 (m, 2H); LC-MS: Method H, RT=1.24 min, MS (ESI) m/z: 334.1 (M+H)$^+$; Analytical HPLC Method B: 98% purity.

Example 11

2-(2-(2-(difluoromethoxy)-7-methylquinoxalin-5-yl)-4-methylthiazol-5-yl)-4-fluoropheno

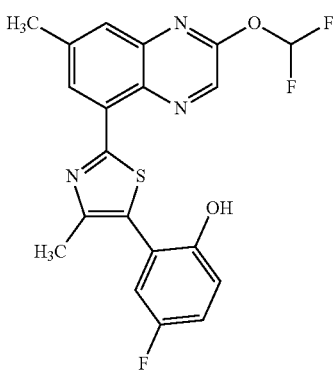

(11)

Intermediate I-18 (20 mg, 0.052 mmol) and (5-fluoro-2-hydroxyphenyl)boronic acid (12.11 mg, 0.078 mmol) were dissolved in DMF (518 μL). PdCl$_2$(dppf)-CH$_2$Cl$_2$ (2.54 mg, 3.11 μmol) was added and the reaction mixture was degassed by bubbling with argon for 15 minutes. Sodium carbonate (2 M, 31.1 μL, 0.062 mmol) was added and the reaction mixture was degassed for 5 minutes, then sealed and heated to 100° C. in the microwave for 30 minutes. The crude material was diluted with MeOH and purified by preparative HPLC (Method A, 40 to 100% B in 20 minutes) to give Example 11 (12.8 mg, 0.031 mmol, 59.2%) as a yellow solid: $^1$H NMR (400 MHz, CHLOROFORM-d) δ 8.65-8.56 (m, 2H), 7.74 (s, 1H), 7.86-7.44 (m, 1H), 7.05 (dd, J=8.7, 2.9 Hz, 1H), 7.02-6.96 (m, 1H), 6.95-6.90 (m, 1H), 2.66 (s, 3H), 2.51-2.45 (m, 3H); LC-MS: Method H, RT=1.13 min. MS (ESI) m/z: 418.0 (M+H)$^+$; Analytical HPLC Method A: 100% purity.

Example 12

2-(2-(2-(difluoromethoxy)-7-methylquinoxalin-5-yl)-4-methylthiazol-5-yl)-3-fluoropheno

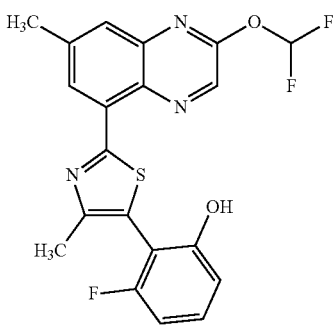

(12)

Intermediate I-18 (20 mg, 0.052 mmol) and (2-fluoro-6-hydroxyphenyl)boronic acid (12.11 mg, 0.078 mmol) were dissolved in DMF (518 μL). PdCl$_2$(dppf)-CH$_2$Cl$_2$ (2.54 mg, 3.11 μmol) was added and the reaction mixture was degassed by bubbling with argon for 15 minutes. Sodium carbonate (2 M, 31.1 μL, 0.062 mmol) was added and the reaction mixture was degassed for 5 minutes, then sealed and heated to 100° C. in the microwave for 30 minutes. The crude material was diluted with MeOH and purified by preparative HPLC (Method A, 40 to 100% B in 20 minutes) to give Example 12 (7.6 mg, 0.018 mmol, 35.2%) as a yellow solid: $^1$H NMR (400 MHz, CHLOROFORM-d) δ 8.64-8.57 (m, 2H), 7.77-7.71 (m, 1H), 7.85-7.45 (m, 1H), 7.27-7.21 (m, 1H), 6.81 (d, J=8.3 Hz, 1H), 6.78-6.71 (m, 1H), 2.67 (s, 3H), 2.43 (s, 3H); LC-MS: Method H, RT=1.12 min, MS (ESI) m/z: 418.1 (M+H)$^+$; Analytical HPLC Method A: 100% purity.

Example 13

2-(2-(difluoromethoxy)-7-methylquinoxalin-5-yl)-5-(piperidin-1-yl)thiazole

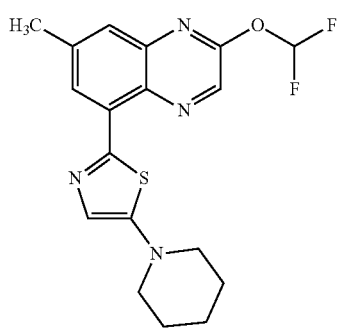

(13)

Intermediate I-10 (25 mg, 0.067 mmol), piperidine (6.86 mg, 0.081 mmol), cesium carbonate (65.7 mg, 0.202 mmol), palladium(II) acetate (1.508 mg, 6.72 μmol), and BINAP (8.37 mg, 0.013 mmol) were dissolved in dioxane (672 μL) and degassed for 15 minutes, then heated to 100° C. for 18 hours. The reaction mixture was diluted with EtOAc, washed with water then brine, dried (Na$_2$SO$_4$), filtered, and concentrated in vacuo. The crude material was diluted with DMF, filtered, and purified by preparative HPLC (Method D, 55 to 95% B in 10 minutes) then repurified by preparative HPLC (Method D, 50 to 90% B in 10 minutes) to give Example 13 (2.2 mg, 0.00567 mmol, 8.4%): $^1$H NMR (500 MHz, METHANOL-d$_4$) δ 8.61 (s, 1H), 8.34 (d, J=1.7 Hz, 1H), 7.83-7.52 (m, 3H), 3.30-3.23 (m, 4H), 2.62 (s, 3H), 1.78 (dt, J=11.3, 5.7 Hz, 4H), 1.69-1.60 (m, 2H); LC-MS: Method H, RT=1.16 min, MS (ESI) m/z: 377.1 (M+H)$^+$; Analytical HPLC Method B: 97% purity.

Example 14

5-(2-(2-(difluoromethoxy)-7-methylquinoxalin-5-yl)thiazol-5-yl)pyridin-3-ol

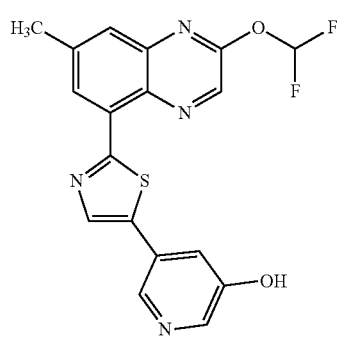

(14)

Intermediate 14A: 3-(benzyloxy)-5-bromopyridine

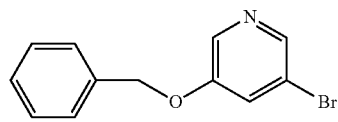

(14A)

5-bromopyridin-3-ol (100 mg, 0.575 mmol), silver carbonate (475 mg, 1.724 mmol), and benzyl bromide (68.4 µL, 0.575 mmol) were dissolved in CHCl₃ (2874 µL) and stirred for 18 hours. The reaction mixture was filtered to remove the silver salts and concentrated in vacuo. The crude material was purified by column chromatography (ISCO, 12 g silica gel column, 19 minute gradient from 0 to 100% EtOAc in hexanes) to give Intermediate 14A (41.2 mg, 0.156 mmol, 27.1%) as a yellow oil: $^1$H NMR (400 MHz, CHLOROFORM-d) δ 8.30 (dd, J=4.4, 2.4 Hz, 2H), 7.45-7.33 (m, 6H), 5.10 (s, 2H); LC-MS: Method H, RT=0.99 min, MS (ESI) m/z: 264/266 (M+H)⁺.

Intermediate 14B: 3-(benzyloxy)-5-(tributylstannyl)pyridine

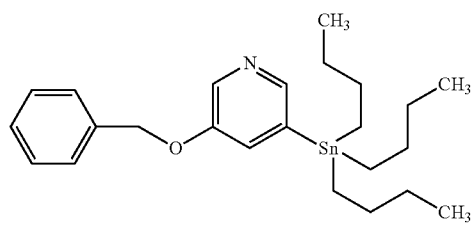

(14B)

Intermediate 14A (41 mg, 0.155 mmol) was dissolved in Et₂O (621 µL) and cooled to −78° C. BuLi (2.5 M, 68.3 µL, 0.171 mmol) was added and the reaction mixture was stirred for 40 minutes. Tributylchlorostannane (42.1 µL, 0.155 mmol) was added and the reaction mixture was allowed to stir for 3 hours. The reaction mixture was warmed to ambient temperature and concentrated in vacuo. The crude material was suspended in hexanes and filtered through dry celite. The residue was concentrated in vacuo to give Intermediate 14B, which was used directly in the subsequent reaction.

Intermediate 14C 5-(5-(benzyloxy)pyridin-3-yl)-2-(2-(difluoromethoxy)-7-methylquinoxalin-5-yl)thiazole

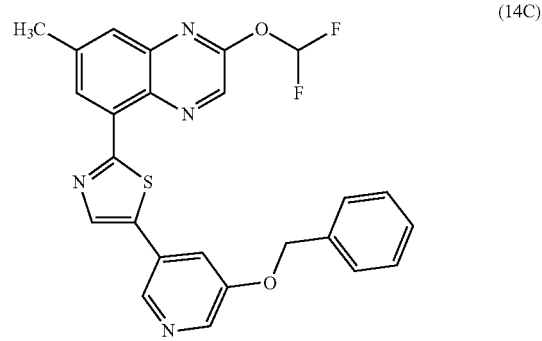 [SMILES: Cc1cc(-c2ncc(-c3cncc(OCc4ccccc4)c3)s2)c2ncc(OC(F)F)nc2c1]

(14C)

Intermediate I-10 (25 mg, 0.067 mmol), Intermediate 14B (39.8 mg, 0.084 mmol), and potassium acetate (13.18 mg, 0.134 mmol) were dissolved in dioxane (973 µL) and degassed by bubbling with argon for 15 minutes. Palladium tetrakistriphenylphosphine (3.88 mg, 3.36 µmol) was added and the reaction mixture was sealed and heated to 120° C. in the microwave for 2 hours. The reaction mixture was diluted with EtOAc, washed with water, 1 N HCl, then brine, dried (Na₂SO₄), filtered, and concentrated in vacuo. The crude material was purified by preparative HPLC (Method A, 30 to 100% B in 20 minutes) to give Intermediate 14C (7.4 mg, 0.016 mmol, 21.1%) as a brown oil: $^1$H NMR (400 MHz, chloroform-d) δ 8.72-8.66 (m, 3H), 8.46 (d, J=2.5 Hz, 1H), 8.26 (s, 1H), 7.89 (s, 1H), 7.80 (d, J=0.8 Hz, 1H), 7.86-7.49 (m, 1H), 7.48-7.38 (m, 5H), 5.28 (s, 2H), 2.68 (s, 3H); LC-MS: Method H, RT=1.13 min, MS (ESI) m/z: 477.0 (M+H)⁺.

Example 14

Intermediate 14C (7.4 mg, 0.016 mmol) was dissolved in MeOH (1553 µL). Palladium on carbon (1.653 mg, 1.553 µmol) was added and the reaction mixture was sealed under a balloon of hydrogen (0.031 mg, 0.016 mmol) for 1.5 hours. The reaction mixture was filtered and purified by preparative HPLC (Method D, 20 to 55% B in 13 minutes) to give Example 14 (2.8 mg, 0.00717 mmol, 46.2%): $^1$H NMR (500 MHz, METHANOL-d₄) δ 8.73 (s, 1H), 8.60 (d, J=1.7 Hz, 1H), 8.39 (s, 1H), 8.21 (s, 1H), 8.11 (br. s., 1H), 7.97 (s, 1H), 7.81 (s, 1H), 7.87-7.56 (m, 1H), 7.52 (s, 1H), 2.68 (s, 3H); LC-MS: Method H, RT=0.89 min, MS (ESI) m/z: 387.0 (M+H)⁺; Analytical HPLC Method B: 99% purity.

Example 15

2-(2-(2-(difluoromethoxy)-7-methylquinoxalin-5-yl)-4-methylthiazol-5-yl)phenol

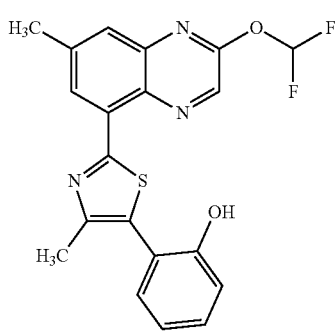

(15)

Intermediate I-18 (16 mg, 0.041 mmol) and (2-hydroxyphenyl)boronic acid (8.57 mg, 0.062 mmol) were dissolved in DMF (414 μL). PdCl$_2$(dppf)-CH$_2$Cl$_2$ (2.030 mg, 2.486 μmol) was added and the reaction mixture was degassed by bubbling with argon for 15 minutes. Sodium carbonate (2 M, 24.86 μL, 0.050 mmol) was added and the reaction mixture was degassed for 5 minutes, then sealed and heated to 100° C. in the microwave for 30 minutes. The crude material was diluted with DMF, filtered, and purified by preparative HPLC (Method D, 45 to 85% B in 10 minutes) to give Example 15 (13.7 mg, 0.034 mmol, 83%): $^1$H NMR (500 MHz, DMSO-d$_6$) δ 9.91 (br. s., 1H), 8.92 (s, 1H), 8.59 (d, J=1.7 Hz, 1H), 7.82 (d, J=0.5 Hz, 1H), 8.06-7.71 (m, 1H), 7.34 (dd, J=7.6, 1.5 Hz, 1H), 7.30-7.22 (m, 1H), 7.01 (d, J=7.7 Hz, 1H), 6.95-6.87 (m, 1H), 2.66 (s, 3H), 2.42 (s, 3H); LC-MS: Method H, RT=1.10 min, MS (ESI) min: 400.0 (M+H)$^+$; Analytical HPLC Method B: 100% purity.

Example 16

2-(2-(difluoromethoxy)-7-methylquinoxalin-5-yl)-5-(2-(trifluoromethyl)phenyl)thiazole

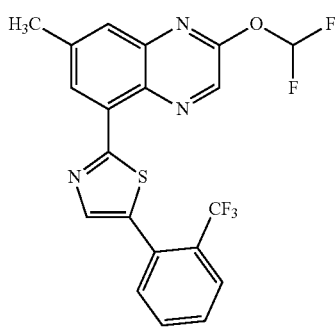

(16)

Intermediate I-10 (20 mg, 0.054 mmol) and (2-(trifluoromethyl)phenyl)boronic acid (15.31 mg, 0.081 mmol) were dissolved in DMF (537 μL). PdCl$_2$(dppf)-CH$_2$Cl$_2$ (2.63 mg, 3.22 μmol) was added and the reaction mixture was degassed by bubbling with argon for 15 minutes. Sodium carbonate (2 M, 32.2 μL, 0.064 mmol) was added and the reaction mixture was degassed for 5 minutes, then sealed and heated to 100° C. in the microwave for 30 minutes. The crude material was diluted with DMF, filtered, and purified by preparative HPLC (Method D, 55 to 95% B in 10 minutes) to give Example 16 (9.1 mg, 0.021 mmol, 38.7%): $^1$H NMR (500 MHz, DMSO-d$_6$) δ 8.95 (s, 1H), 8.67 (d, J=1.7 Hz, 1H), 8.07-7.69 (m, 7H), 2.67 (s, 3H); LC-MS: Method H, RT=1.25 min, MS (ESI) m/z: 437.9 (M+H)$^+$; Analytical HPLC Method B: 100% purity.

Example 17

5-cyclohexyl-2-(2-(difluoromethoxy)-7-methyl quinoxalin-5-yl)thiazole

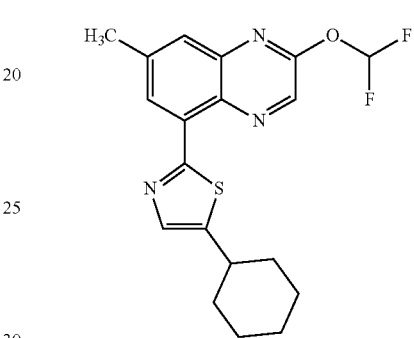

(17)

Intermediate 17A 5-(cyclohex-1-en-1-yl)-2-(2-(difluoromethoxy)-7-methylquinoxalin-5-yl)thiazole

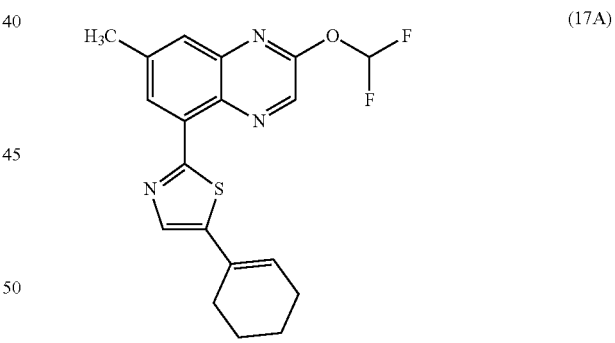

(17A)

Intermediate I-10 (20 mg, 0.054 mmol) and cyclohex-1-en-1-ylboronic acid (13.54 mg, 0.107 mmol) were dissolved in DMF (537 μL). PdCl$_2$(dppf)-CH$_2$Cl$_2$ (2.63 mg, 3.22 μmol) was added and the reaction mixture was degassed by bubbling with argon for 15 minutes. Sodium carbonate (2 M, 32.2 μL, 0.064 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 55 to 95% B in 10 minutes) to give 1A (7.1 mg, 0.018 mmol, 33.3%): $^1$H NMR (500 MHz, METHANOL-d$_4$) δ 8.66 (s, 1H), 8.46 (d, J=1.7 Hz, 1H), 7.75 (s, 1H), 7.74 (d, J=0.8 Hz, 1H), 7.84-7.53 (m, 1H), 6.34 (t, J=4.1 Hz, 1H), 2.64 (s, 3H), 2.52-2.45 (m, 2H), 2.26 (d, J=3.6 Hz, 2H), 1.87-1.80 (m, 2H), 1.75-1.68 (m, 2H); LC-MS: Method H, RT=1.31 min, MS (ESI) m/z: 374.1 (M+H)⁺; Analytical HPLC Method B: 94% purity.

Example 17

Intermediate 17A (6.05 mg, 0.016 mmol) was dissolved in EtOAc (405 µL) and MeOH (405 µL). Palladium on carbon (1.724 mg, 0.016 mmol) was added and the reaction mixture was sealed under an atmosphere of hydrogen for 3 hours. The reaction mixture was filtered and concentrated in vacuo. The crude material was diluted with DMF, filtered, and purified by preparative HPLC (Method D, 50 to 95% B in 22 minutes) then repurified by preparative HPLC (Method D, 55 to 92% B in 22 minutes) to give Example 17 (0.7 mg, 0.001865 mmol, 11.5%): ¹H NMR (500 MHz, METHANOL-d₄) δ 8.67 (s, 1H), 8.44 (d, J=1.4 Hz, 1H), 7.85-7.53 (m, 3H), 3.02-2.92 (m 1H), 2.65 (s, 3H), 2.14 (d, J=11.8 Hz, 2H), 1.88 (d, J=13.2 Hz, 2H), 1.78 (d, J=12.7 Hz, 1H), 1.63-1.52 (m, 2H), 1.52-1.41 (m, 2H), 1.38-1.30 (m, 1H); LC-MS: Method H, RT=1.28 min, MS (ESI) m/z: 376.1 (M+H)⁺; Analytical HPLC Method B: 100% purity.

Example 18

2-(2-(methoxy methyl)-7-methylquinoxalin-5-yl)-5-phenylthiazole

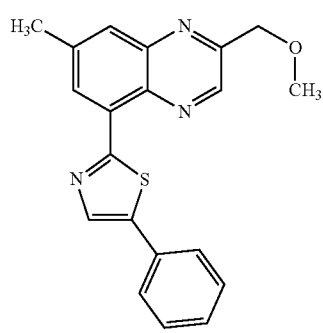

(18)

Intermediate I-13 (12.5 mg, 0.036 mmol) and phenylboronic acid (6.53 mg, 0.054 mmol) were dissolved in DMF (357 µL). PdCl₂(dppf)-CH₂Cl₂ (1.749 mg, 2.141 µmol) was added and the reaction mixture was degassed by bubbling with argon for 15 minutes. Sodium carbonate (2 M, 21.41 µL, 0.043 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 50 to 90% B in 20 minutes) then repurified by preparative HPLC (Method D, 45 to 85% B in 20 minutes) to give Example 18 (2.6 mg, 0.00748 mmol, 21%): ¹H NMR (500 MHz, DMSO-d₆) δ 9.10 (s, 1H), 8.70 (s, 1H), 8.45 (s, 1H), 7.99 (s, 1H), 7.81 (d, J=8.0 Hz, 2H), 7.51 (t, J=7.6 Hz, 2H), 7.44-7.39 (m, 1H), 4.82 (s, 2H), 3.48 (s, 3H), 2.67 (s, 3H); LC-MS: Method H, RT=1.37 min, MS (ESI) m/z: 348.2 (M+H)⁺; Analytical HPLC Method B: 100% purity.

Example 19

2-(2-(2-(difluoromethoxy)-7-methylquinoxalin-5-yl)thiazol-5-yl)-6-fluorophenol

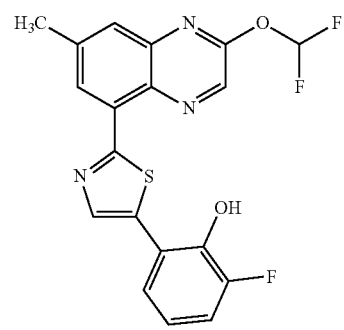

(19)

Intermediate I-10 (18 mg, 0.048 mmol) and (3-fluoro-2-hydroxyphenyl)boronic acid (15.1 mg, 0.097 mmol) were dissolved in DMF (4.8 mL). Potassium carbonate (20 mg, 0.145 mmol) was dissolved in water (0.12 mL) and added to the reaction mixture. PdCl₂(dppf)-CH₂Cl₂ (3.16 mg, 0.00387 mmol) was added and the reaction mixture was heated to 110° C. for 1.5 hours. The reaction mixture was cooled to ambient temperature, filtered, and purified by purified by preparative HPLC (Method D, 20 to 95% B in 10.9 minutes) to give Example 19 (7.7 mg): ¹H NMR (500 MHz, DMSO-d₆) δ 8.96 (s, 1H), 8.66 (d, J=1.8 Hz, 1H), 8.56 (s, 1H), 8.06-7.75 (m, 2H), 7.66 (d, J=7.9 Hz, 1H), 7.21 (t, J=9.5 Hz, 1H), 6.93 (d, J=5.5 Hz, 1H), 2.66 (s, 3H); LC-MS: Method G, RT=4.52 min, MS (ESI) m/z: 404.3 (M+H)⁺; Analytical HPLC Method B: 93% purity.

Example 20

2-(2-(2-(difluoromethoxy)-7-methylquinoxalin-5-yl)thiazol-5-yl)-4-methylphenol

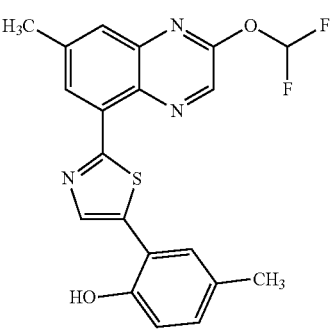

(20)

Example 20 (1.0 mg) was prepared in a manner analogous to Example 19: ¹H NMR (500 MHz, DMSO-d₆) δ 8.98 (s, 1H), 8.64 (d, J=1.8 Hz, 1H), 8.51 (s, 1H), 8.06-7.75 (m, 2H), 7.61 (d, J=1.5 Hz, 1H), 7.03 (dd, J=8.2, 1.8 Hz, 1H), 6.92 (d, J=8.2 Hz, 1H), 2.66 (s, 3H), 2.30 (s, 3H); LC-MS: Method G, RT=3.42 min, MS (ESI) m/z: 400.2 (M+H)⁺; Analytical HPLC Method B: 92% purity.

Example 21

2-(2-(2-(difluoromethoxy)-7-methylquinoxalin-5-yl)thiazol-5-yl)-4-fluorophenol

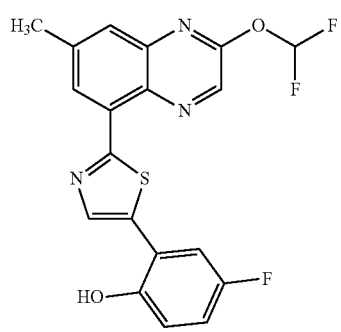

(21)

Example 21 (2.0 mg) was prepared in a manner analogous to Example 19: $^1$H NMR (500 MHz, DMSO-d$_6$) δ 8.98 (s, 1H), 8.65 (d, J=1.5 Hz, 1H), 8.60 (s, 1H), 8.06-7.75 (m, 2H), 7.72 (dd, J=10.1, 3.1 Hz, 1H), 7.11-7.04 (m, 1H), 7.03-6.97 (m, 1H), 2.66 (s, 3H); LC-MS: Method G, RT=4.53 min, MS (ESI) m/z: 404.0 (M+H)$^+$; Analytical HPLC Method B: 94% purity.

Example 22

2-(2-(2-(difluoromethoxy)-7-methylquinoxalin-5-yl)thiazol-5-yl)-4-chlorophenol

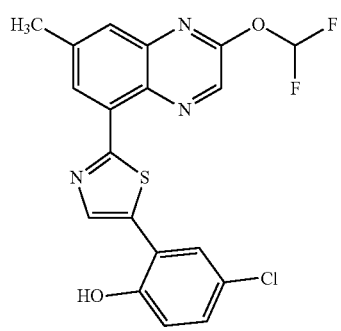

(22)

Example 22 (3.3 mg) was prepared in a manner analogous to Example 19: $^1$H NMR (500 MHz, DMSO-d$_6$) δ 8.98 (s, 1H), 8.65 (d, J=1.8 Hz, 1H), 8.61 (s, 1H), 8.07-7.72 (m, 3H), 7.24 (dd, J=8.7, 2.6 Hz, 1H), 7.02 (d, J=8.9 Hz, 1H), 2.66 (s, 3H); LC-MS: Method G, RT=3.99 min, MS (ESI) m/z: 419.9 (M+H)$^+$; Analytical HPLC Method B: 100% purity.

Example 23

2-(2-(2-(difluoromethoxy)-7-methyl quinoxalin-5-yl)thiazol-5-yl)-6-chlorophenol

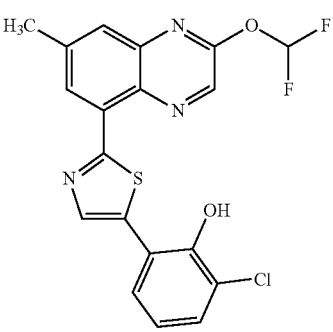

(23)

Example 23 (7.4 mg) was prepared in a manner analogous to Example 19: $^1$H NMR (500 MHz, DMSO-d) δ 8.94 (s, 1H), 8.66 (d, J=1.8 Hz, 1H), 8.56 (s, 1H), 8.07-7.75 (m, 3H), 7.42 (dd, J=7.9, 1.2 Hz, 1H), 6.99 (t, J=7.8 Hz, 1H), 2.66 (s, 3H); LC-MS: Method G, RT=4.60 min, MS (ESI) m/z: 420.4 (M+H)$^+$; Analytical HPLC Method B: 95% purity.

Example 24

2-(2-(2-(difluoromethoxy)-7-methylquinoxalin-5-yl)thiazol-5-yl)-3-fluorophenol

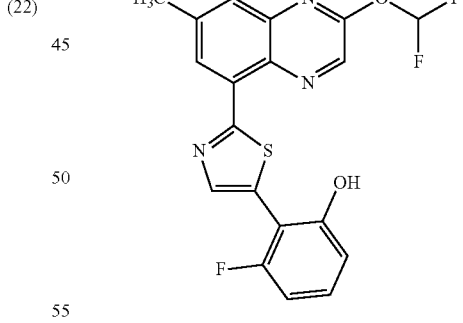

(24)

Example 24 (2.9 mg) was prepared in a manner analogous to Example 19: $^1$H NMR (500 MHz, DMSO-d) δ 8.96 (s, 1H), 8.66 (d, J=1.8 Hz, 1H), 8.56 (s, 1H), 8.08-7.74 (m, 2H), 7.66 (d, J=7.9 Hz, 1H), 7.21 (t, J=9.5 Hz, 1H), 6.93 (d, J=5.5 Hz, 1H), 2.66 (s, 3H); LC-MS: Method G, RT=3.73 min, MS (ESI) m/z: 403.9 (M+H)$^+$; Analytical HPLC Method B: 100% purity.

Example 25

3-(2-(2-(difluoromethoxy)-7-methylquinoxalin-5-yl)thiazol-5-yl)-4-fluorophenol

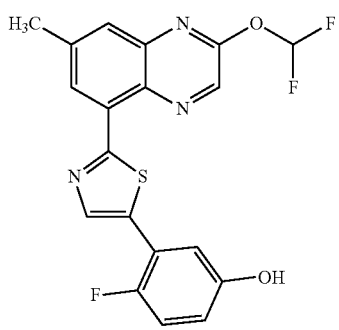

(25)

Example 25 (6.8 mg) was prepared in a manner analogous to Example 19: $^1$H NMR (500 MHz, DMSO-$d_6$) δ 9.72 (br. s., 1H), 9.01 (s, 1H), 8.67 (s, 1H), 8.43 (s, 1H), 8.07-7.75 (m, 2H), 7.26-7.20 (m, 2H), 6.87-6.80 (m, 1H), 2.67 (s, 3H); LC-MS: Method G, RT=4.60 min, MS (ESI) m/z: 404.1 (M+H)$^+$; Analytical HPLC Method B: 97% purity.

Example 26

3-(2-(2-(difluoromethoxy)-7-methylquinoxalin-5-yl)thiazol-5-yl)-5-fluorophenol

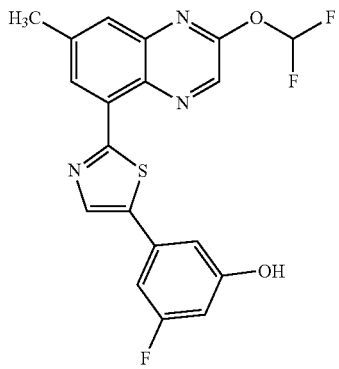

(26)

Example 26 (6.2 mg) was prepared in a manner analogous to Example 19: $^1$H NMR (500 MHz, DMSO-$d_6$) δ 8.99 (s, 1H), 8.64 (s, 1H), 8.48 (s, 1H), 8.06-7.75 (m, 2H), 7.15 (d, J=9.5 Hr, 1H), 7.01 (s, 1H), 6.61 (d, J=10.7 Hz, 1H), 2.66 (s, 3H); LC-MS: Method G, RT=4.66 min, MS (ESI) m/z: 404.2 (M+H)$^+$; Analytical HPLC Method B: 100% purity.

Example 27

3-(2-(2-difluoromethoxy)-7-methylquinoxalin-5-yl)thiazol-5-yl)-4-(trifluoromethoxy)phenol

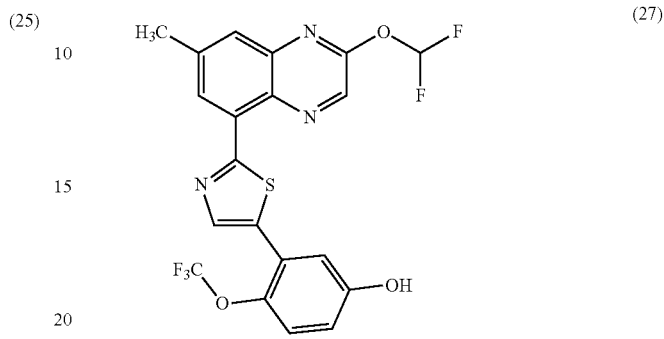

(27)

Example 27 (6.9 mg) was prepared in a manner analogous to Example 19: $^1$H NMR (500 MHz, DMSO-$d_6$) δ 8.97 (s, 1H), 8.66 (s, 1H), 8.36 (s, 1H), 8.06-7.74 (m, 2H), 7.39 (d, J=8.9 Hz, 1H), 7.26 (d, J=2.7 Hz, 1H), 6.92 (dd, J=8.9, 2.7 Hz, 1H), 2.67 (s, 3H); LC-MS: Method G, RT=4.71 min, MS (ESI) m/z: 470.2 (M+H)$^+$; Analytical HPLC Method B: 100% purity.

Example 28

2-(2-(difluoromethoxy)-7-methylquinoxalin-5-yl)-5-phenyl thiazole

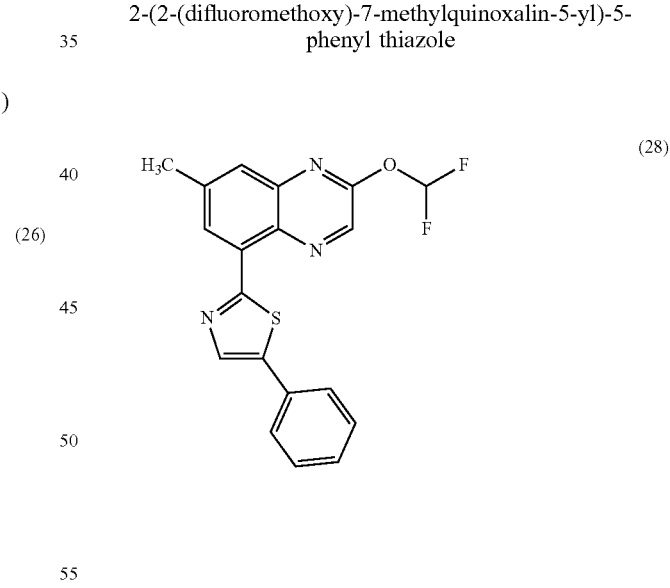

(28)

Intermediate I-10 (20 mg, 0.054 mmol), phenylboronic acid (7.86 mg, 0.064 mmol) and potassium phosphate tribasic (22.8 mg, 0.107 mmol) were dissolved in acetonitrile (1 mL) and water (0.2 mL). The reaction mixture was degassed for 5 minutes. Tetrakis(triphenylphosphine)palladium polymer bound (3.35 mg, 0.00269 mmol) was added. The reaction mixture was heated to 110° C. in the microwave for 30 minutes. The reaction mixture was purified by preparative HPLC (Method D, 10 to 100% B in 20 minutes) to give Example 28 (2.2 mg): LC-MS: Method G, MS (ESI) m/z: 370 (M+H)$^+$; 95.3% purity.

Example 29

2-(2-(difluoromethoxy)-7-methylquinoxalin-5-yl)-5-(pyridin-3-yl)thiazole

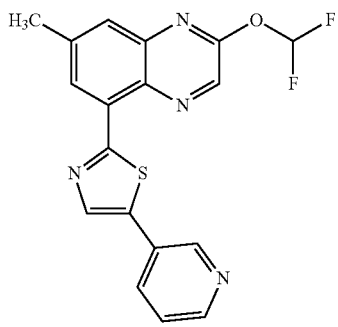
(29)

Example 29 (2.2 mg) was prepared in a manner analogous to Example 28: LC-MS: Method G, MS (ESI) m/z: 371 (M+H)+; 94.5% purity.

Example 30

2-(2-(2-(difluoromethoxy)-7-methylquinoxalin-5-yl)thiazol-5-yl)phenol

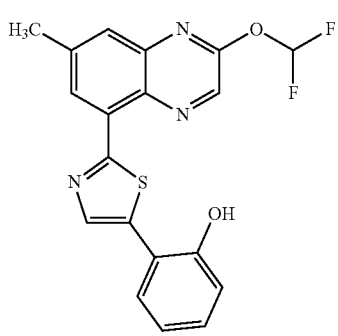
(30)

Example 30 (4.1 mg) was prepared in a manner analogous to Example 28: LC-MS: Method G, MS (ESI) m/z: 386 (M+H)+; 99.2% purity.

Example 31

N-ethyl-2-(2-methoxy-7-methylquinoxalin-5-yl)thiazole-5-carboxamide

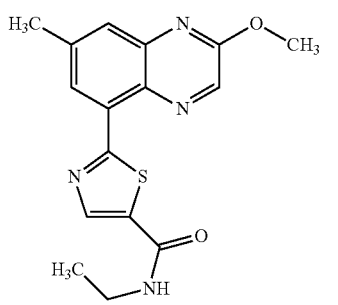
(31)

Intermediate I-23 (10 mg, 0.033 mmol), PyBOP (20.7 mg, 0.04 mmol), and ethylamine (1.8 mg, 0.040 mmol) was dissolved in DMF (1 mL) and DIPEA (0.017 mL, 0.100 mmol) and stirred for 3 hours. The reaction mixture was heated to 65° C. for 3 hours. The reaction mixture was purified by preparative HPLC (Method D, 10 to 100% B in 18 minutes) to give Example 31 (1.4 mg, 0.00414 mmol, 12.5%): LC-MS: Method G, MS (ESI) m/z: 329 (M+H)+: 97.1% purity.

Example 32

2-(2-(difluoromethoxy)-7-methylquinoxalin-5-yl)-N-(4-methoxyphenyl)thiazole-4-carboxamide

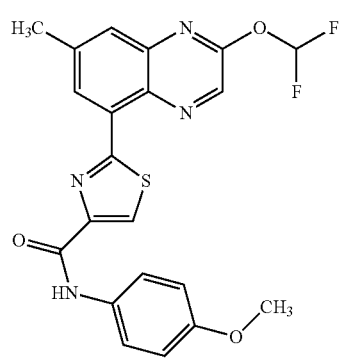
(32)

Intermediate I-24 (12 mg, 0.036 mmol), EDC (8.18 mg, 0.043 mmol), HOBt (6.54 mg, 0.043 mmol), 4-methoxyaniline (5.70 mg, 0.046 mmol), and DIPEA (0.019 mL, 0.107 mmol) were dissolved in DMF (1 mL) and stirred for 18 hours. The reaction mixture was purified by preparative HPLC (Method D, 10 to 100% B in 18 minutes) to give Example 32 (0.97 mg, 0.00209 mmol, 5.9%).

Example 33

(2-(2-(difluoromethoxy)-7-methylquinoxalin-5-yl)thiazol-4-yl)(4-(hydroxymethyl)piperidin-1-yl)methanone

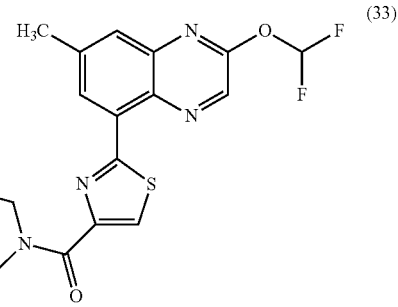
(33)

Example 33 (1.0 mg, 0.00217 mmol, 5.6%) was prepared in a manner analogous to Example 32: LC-MS: Method G, MS (ESI) m/z: 435.2 (M+H); 94.2% purity.

Example 34

2-(2-(difluoromethoxy)-7-methylquinoxalin-5-yl)thiazole

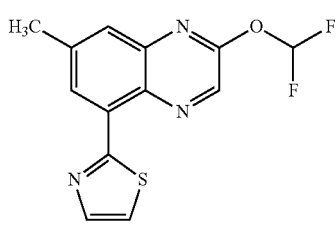

(34)

Intermediate I-1 (0.007 g, 0.028 mmol) and 2-bromothiazole (4.52 mg, 0.028 mmol) were dissolved in DMF (3 mL). PdCl$_2$(dppf)-CH$_2$Cl$_2$ Adduct (1.350 mg, 1.654 μmol) was added and the reaction mixture was degassed by bubbling with argon for 15 minutes. 3 M Na$_2$CO; (0.018 mL, 0.055 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was diluted with DMF, filtered, and purified by preparative HPLC (Method D, 35 to 75% B in 10 minutes) to yield Example 34 (0.0047 g, 0.016 mmol, 57.0% yield): $^1$H NMR (500 MHz, METHANOL-d$_4$) δ 8.69 (s, 1H), 8.55 (d, J=1.9 Hz, 1H), 7.98 (d, J=3.3 Hz, 1H), 7.85-7.55 (m, 3H), 2.66 (s, 2H). LC-MS: method H, RT=1.18 min, MS (ESI) m/z: 294.0 (M+H)$^+$. Analytical HPLC Method B: 100% purity.

Example 35

2-(2-(difluoromethoxy)-7-methylquinoxalin-5-yl)-5-phenyl-1,3,4-thiadiazole

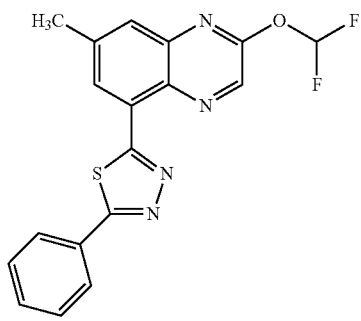

(35)

Intermediate I-1

2-(difluoromethoxy)-7-methyl-5-(4,4,5,5-tetramethyl-1,3,2-dioxaborolan-2-yl)quinoxaline (0.025 g, 0.074 mmol) and 2-bromo-5-phenyl-1,3,4-thiadiazole (0.018 g, 0.074 mmol) were dissolved in DMF (1 mL). PdCl$_2$(dppf)-CH$_2$Cl$_2$ adduct (3.64 mg, 4.46 μmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was diluted with DMF, filtered, and purified by preparative HPLC (Method D, 50 to 90% B in 10 minutes) to yield Example 35 (0.0155 g, 0.041 mmol, 55.1% yield): $^1$H NMR (500 MHz, METHANOL-d$_4$) δ 8.75 (d, J=1.9 Hz, 1H), 8.70 (s, 1H), 8.08-8.05 (m, 2H), 7.88 (d, J=0.8 Hz, 1H), 7.84-7.57 (m, 1H), 7.57 (s, 1H), 7.56-7.54 (m, 2H), 2.70 (s, 3H). LC-MS: method H. RT=1.19 min, MS (ESI) m/z: 370.8 (M+H)$^+$. Analytical HPLC Method B: 98% purity.

Example 36

2-(2-(difluoromethoxy)-7-methylquinoxalin-5-yl)-4-methylthiazole

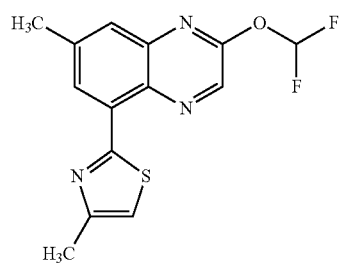

(36)

Intermediate I-1 (0.015 g, 0.045 mmol) and 2-bromo-4-methylthiazole (7.95 mg, 0.045 mmol) were dissolved in DMF (1 mL). PdCl$_2$(dppf)-CH$_2$Cl$_2$Adduct (2.187 mg, 2.68 μmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was diluted with DMF, filtered, and purified by preparative HPLC (Method D, 45% to 85% B in 10 minutes) to yield Example 36 (0.006 g, 0.019 mmol, 43.3% yield): $^1$H NMR (500 MHz, METHANOL-d$_4$) δ 8.65 (s, 1H), 8.50 (d, J=1.7 Hz, 1H), 7.82-7.51 (m, 3H), 2.65 (s, 3H), 2.56 (d, J=0.6 Hz, 3H). LC-MS: method H, RT=1.11 min, MS (ESI) m/z: 307.9 (M+H)$^+$. Analytical HPLC Method B: 99% purity.

Example 37

2-(2-(difluoromethoxy)-7-methylquinoxalin-5-yl)-5-(1H-indol-7-yl)thiazole

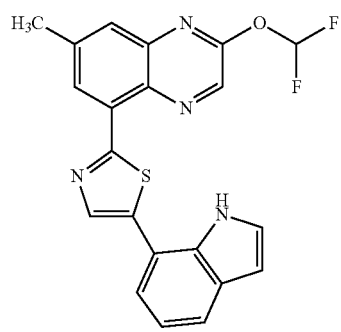

(37)

Intermediate I-10 (0.020 g, 0.054 mmol) and (1H-indol-7-yl)boronic acid (8.65 mg, 0.054 mmol) were dissolved in DMF (1 mL). PdCl$_2$(dppf)-CH$_2$Cl$_2$ adduct (2.63 mg, 3.22 μmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was diluted with DMF, filtered, and purified by preparative HPLC (Method D, 50% to 90% B in 10 minutes) to yield Example 37 (0.0048 g, 0.012 mmol, 21.87% yield): $^1$H NMR (500 MHz, METHANOL-d$_4$) δ 8.71 (s, 1H), 8.53 (d, J=1.4 Hz, 1H), 8.12 (s, 1H), 7.86-7.54 (m, 5H), 7.42 (dd, J=8.3, 1.4 Hz, 1H), 7.29 (d, J=3.0 Hz, 1H), 6.51 (d, J=2.8 Hz, 1H), 2.67 (s, 3H). LC-MS: method H, RT=1.17 min, MS (ESI) m/z: 409.1 (M+H)$^+$. Analytical HPLC Method B: 100% purity.

Example 38

2-(2-(difluoromethoxy)-7-methylquinoxalin-5-yl)-5-(1H-indol-4-yl)thiazole

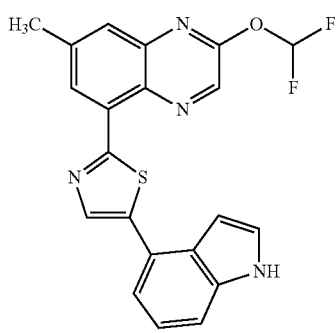

(38)

Intermediate I-10 (0.020 g, 0.054 mmol) and (1H-indol-4-yl)boronic acid (8.65 mg, 0.054 mmol) were dissolved in DMF (1 mL). PdCl$_2$(dppf)-CH$_2$Cl$_2$ adduct (2.63 mg, 3.22 μmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was diluted with DMF, filtered, and purified by preparative HPLC (Method D, 55% to 95% B in 10 minutes) to yield Example 38 (0.0027 g, 6.35 μmol, 11.81% yield. $^1$H NMR (500 MHz, METHANOL-d$_4$) δ 8.71 (s, 1H), 8.57 (d, J=1.7 Hz, 1H), 8.28 (s, 1H), 7.85-7.53 (m, 3H), 7.47 (d, J=8.0 Hz, 1H), 7.40 (dd, J=7.3, 0.7 Hz, 1H), 7.37 (d, J=3.0 Hz, 1H), 7.26-7.19 (m, 1H), 6.90 (dd, J=3.2, 0.7 Hz, 1H), 2.68 (s, 3H). LC-MS: method H, RT=1.29 min, MS (ESI) m/z: 409.1 (M+H)$^+$. Analytical HPLC Method B: 96% purity.

Example 39

(2-(2-(difluoromethoxy)-7-methylquinoxalin-5-yl)thiazol-5-yl)methanol

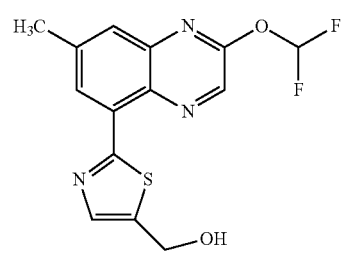

(39)

Intermediate I-1 (0.025 g, 0.074 mmol) and (2-bromothiazol-5-yl)methanol (0.012 g, 0.062 mmol) were dissolved in DMF (1 mL). PdCl$_2$(dppf)-CH$_2$Cl$_2$ adduct (3.04 mg, 3.72 μmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was diluted with DMF, filtered, and purified by preparative HPLC (Method D, 25% to 70% B in 10 minutes) to yield Example 39 (0.0059 g, 0.018 mmol, 29.4% yield): $^1$H NMR (500 MHz, METHANOL-d$_4$) δ 8.66 (s, 1H), 8.50 (d, J=1.7 Hz, 1H), 7.83-7.81 (m, 1H), 7.79-7.52 (m, 2H), 4.90 (d, J=0.8 Hz 2H), 2.65 (s, 3H). LC-MS: method H, RT=0.93 min, MS (ESI) m/z: 323.9 (M+H)$^+$. Analytical HPLC Method B: 100% purity.

Example 40

2-(2-(difluoromethoxy)-7-methylquinoxalin-5-yl)-5-(1H-pyrazol-5-yl)thiazole

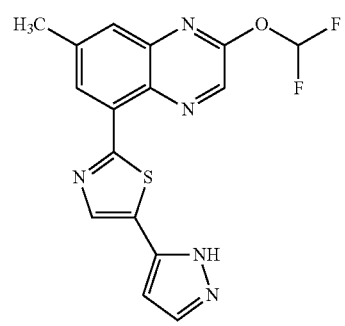

(40)

Intermediate I-10 (0.020 g, 0.054 mmol) and (1H-pyrazol-5-yl)boronic acid (6.01 mg, 0.054 mmol) were dissolved in DMF (1 mL). PdCl$_2$(dppf)-CH$_2$Cl$_2$ adduct (2.63 mg, 3.22 μmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was diluted with DMF, filtered, and purified by preparative HPLC (Method D, 30% to 75% B in 10 minutes) to yield Example 40 (0.005 g, 0.014 mmol, 25.9% yield): $^1$H NMR (500 MHz, METHANOL-$d_4$) δ 8.68 (s, 1H), 8.56 (d, J=1.7 Hz, 1H), 8.18 (s, 1H), 7.86-7.52 (m, 4H), 6.66 (d, J=2.2 Hz, 1H), 2.66 (s, 3H). LC-MS: method H, RT=1.04 min, MS (ESI) m/z: 360.1 (M+H)$^+$. Analytical HPLC Method B: 100% purity.

Example 41

4-(tert-butyl)-2-(2-difluoromethoxy)-7-methylquinoxalin-5-yl)thiazole

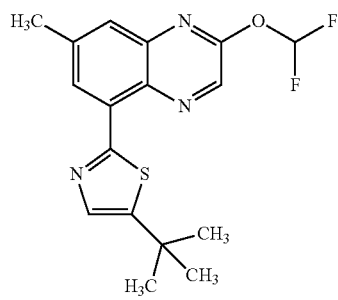

(41)

Intermediate I-1 (0.015 g, 0.045 mmol) and 2-bromo-4-(tert-butyl)thiazole (9.82 mg, 0.045 mmol) were dissolved in DMF (3 mL). PdCl$_2$(dppf)-CH$_2$Cl$_2$ adduct (2.187 mg, 2.68 µmol) was added and the reaction mixture was degassed by bubbling with argon for 15 minutes. Na$_2$CO$_3$, 3 M aqueous solution (0.3 mL, 0.900 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was diluted with DMF, filtered, and purified by preparative HPLC (Method D, 60% to 100% B in 10 minutes) to yield Example 41 (0.0079 g, 0.023 mmol, 50.7% yield): $^1$H NMR (500 MHz, METHANOL-d) δ 8.64 (s, 1H), 8.58 (d, J=1.7 Hz, 1H), 7.72 (d, J=0.8 Hz, 1H), 7.53 (s, 1H), 7.83-7.51 (m, 1H), 2.66 (s, 3H), 1.44 (s, 9H). LC-MS: method H, RT=1.33 min, MS (ESI) m/z: 350.2 (M+H)$^+$. Analytical HPLC Method B: 97% purity.

Example 42

2-(2-(difluoromethoxy)-7-methylquinoxalin-5-yl)-5-(1H-indol-6-yl)thiazole

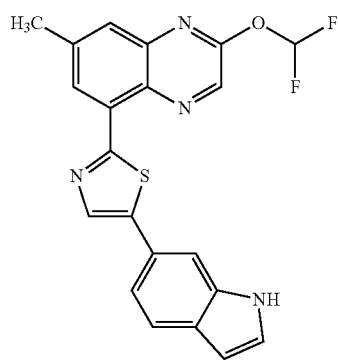

(42)

Intermediate I-10 (0.020 g, 0.054 mmol) and (1H-indol-6-yl)boronic acid (8.65 mg, 0.054 mmol) were dissolved in DMF (3 mL). PdCl$_2$(dppf)-CH$_2$Cl$_2$ adduct (2.63 mg, 3.22 µmol) was added and the reaction mixture was degassed by bubbling with argon for 15 minutes. Na$_2$CO$_3$, 3 M aqueous solution (0.3 mL, 0.900 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was diluted with DMF, filtered, and purified by preparative HPLC (Method D, 50% to 95% B in 10 minutes) to yield Example 42 (0.0054 g, 0.013 mmol, 24.60% yield): $^1$H NMR (500 MHz, METHANOL-$d_4$) δ 8.71 (s, 1H), 8.53 (d, J=1.7 Hz, 1H), 8.12 (s, 1H), 7.76 (s, 1H), 7.65 (d, J=8.3 Hz, 1H), 7.57 (d, J=1.4 Hz, 2H), 7.85-7.54 (m, 1H), 7.42 (dd, J=8.1, 1.5 Hz, 1H), 7.29 (d, J=3.0 Hz, 1H), 6.51 (d, J=3.0 Hz, 1H), 2.67 (s, 3H). LC-MS: method H, RT=1.21 min, MS (ESI) m/z: 408.9 (M+H)$^+$. Analytical HPLC Method B: 100% purity.

Example 43

2-(2-(difluoromethoxy)-7-methylquinoxalin-5-yl)-5-(pyridin-4-yl)thiazole

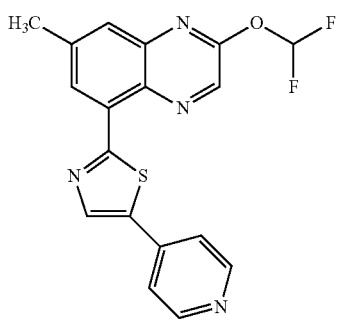

(43)

In a microwave tube to a degassed solution of Intermediate I-10 (0.020 g, 0.054 mmol), 2-(tributylstannyl)thiazole (0.020 g, 0.054 mmol) and potassium acetate (10.55 mg, 0.107 mmol) in dioxane (3 mL) at room temperature was added Pd(Ph$_3$)$_4$ (3.10 mg, 2.69 µmol). The reaction mixture was then heated at 120° C. for 2 hours. The reaction mixture was diluted with water and EtOAc. The layers were separated and the organic layer was washed with brine, dried with sodium sulfate, and concentrated under reduced pressure to yield a yellow solid. The reaction mixture was diluted with DMF, filtered, and purified by preparative HPLC (Method D, 40% to 100% B in 10 minutes) to yield Example 43 (0.0064 g, 0.016 mmol, 30.5% yield): $^1$H NMR (500 MHz, DMSO-$d_6$) δ 8.99 (s, 1H), 8.73 (s, 1H), 8.69-8.65 (m, 3H), 7.91-7.89 (m, 1H), 7.81-7.78 (m, 2H), 8.05-7.75 (m, 1H), 2.67 (s, 3H) LC-MS: method H, RT=0.87 min, MS (ESI) m/z: 371.1 (M+H)$^+$. Analytical HPLC Method B: 95% purity.

Example 44

2-(2-(difluoromethoxy)-7-methylquinoxalin-5-yl)-5-(pyridin-2-yl)thiazole

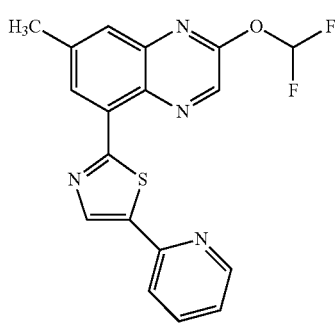

(44)

Intermediate I-10 (0.020 g, 0.054 mmol) and 2-(4,4,5,5-tetramethyl-1,3,2-dioxaborolan-2-yl)pyridine (0.011 g, 0.054 mmol) were dissolved in DMF (1 mL). PdCl$_2$(dppf)-CH$_2$Cl$_2$ adduct (2.63 mg, 3.22 µmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was diluted with DMF, filtered, and purified by preparative HPLC (Method D, 45% to 85% B in 10 minutes) to yield Example 44 (0.0017 g, 4.41 µmol, 8.20% yield): $^1$H NMR (500 MHz, METHANOL-d) δ 8.71 (s, 1H), 8.62-8.57 (m, 2H), 8.43 (s, 1H), 7.86 (d, J=1.1 Hz, 1H), 7.80 (s, 1H), 7.87-7.54 (m, 1H), 7.57 (s, 2H), 2.68 (s, 3H). LC-MS: method H, RT=1.11 min, MS (ESI) m/z: 371.9 (M+H)$^+$. Analytical HPLC Method B: 96% purity.

Example 45

5-(2-(difluoromethyl)phenyl)-2-(2-methoxy-7-methylquinoxalin-5-yl)thiazole

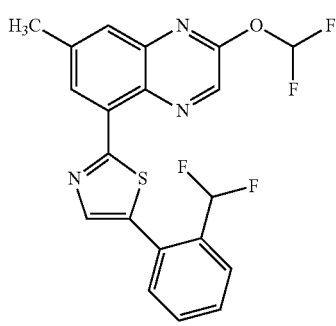

(45)

Palladium (11) acetate (0.397 mg, 1.767 µmol), tricyclohexylphosphonium tetrafluoroborate (1.301 mg, 3.53 µmol). K$_2$CO$_3$ (7.32 mg, 0.053 mmol), and pivalic acid (1.230 µl, 10.60 µmol) were charged to a vial. Intermediate I-11 (0.010 g, 0.039 mmol) was added and the vial was flushed with argon. A solution of 1-bromo-2-(difluoromethyl)benzene (7.31 mg, 0.035 mmol) in DMA (0.118 mL) was added and the reaction mixture was allowed to stir at 100° C. for 18 h. Reaction mixture was diluted with EtOAc and filtered. The filtrate was concentrated. The reaction mixture was diluted with DMF, filtered, and purified by preparative HPLC (Method D, 55% to 95% B in 10 minutes) to yield Example 45 (0.0043 g, 10.88 µmol, 30.8% yield): $^1$H NMR (500 MHz, METHANOL-d$_4$) δ 8.52 (s, 1H), 8.45 (d, J=1.1 Hz, 1H), 7.90 (s, 1H), 7.82 (d, J=6.6 Hz, 1H), 7.75 (s, 1H), 7.60-7.57 (m, 3H), 6.90-6.66 (m, 1H), 4.13 (s, 3H), 2.65 (s, 3H). LC-MS: method H, RT=1.14 min, MS (ESI) m/z: 384.9 (M+H)$^+$. Analytical HPLC Method B: 97% purity.

Example 46

2,3-difluoro-5-(2-(2-methoxy-7-methylquinoxalin-5-yl)thiazol-5-yl)phenol

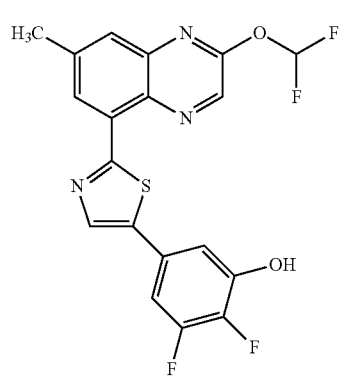

(46)

Palladium (II) acetate (0.397 mg, 1.767 µmol), tricyclohexylphosphonium tetrafluoroborate (1.301 mg, 3.53 µmol), K$_2$CO$_3$ (7.32 mg, 0.053 mmol), and pivalic acid (1.230 µl, 10.60 µmol) were charged to a vial. Intermediate I-11 (0.010 g, 0.039 mmol) was added and the vial was flushed with argon. A solution of 5-bromo-2,3-difluorophenol (7.38 mg, 0.035 mmol) in DMA (0.118 mL) was added and the reaction mixture was allowed to stir at 100° C. for 18 h. Reaction mixture was diluted with EtOAc and filtered. The filtrate was concentrated. The reaction mixture was diluted with DMF, filtered, and purified by preparative HPLC (Method D, 50% to 85% B in 10 minutes) to yield Example 46 (0.0008 g, 2.055 µmol, 5.82% yield) $^1$H NMR (500 MHz, METHANOL-d$_4$) δ 8.54 (s, 1H), 8.39 (d, J=1.4 Hz, 1H), 8.03 (s, 1H), 7.73 (s, 1H), 7.06 (d, J=6.9 Hz, 1H), 7.00 (ddd, J=10.7, 6.4, 1.9 Hz, 1H), 4.25 (br. s., 1H), 4.13 (s, 3H), 2.63 (s, 3H). LC-MS: method H, RT=1.17 min. MS (ESI) m/z: 386.1 (M+H)$^+$. Analytical HPLC Method B: 99% purity.

Example 47

Cyclohexyl(2-(2-methoxy-7-methylquinoxalin-5-yl)-4-(trifluoromethyl)thiazol-5-yl) methanone

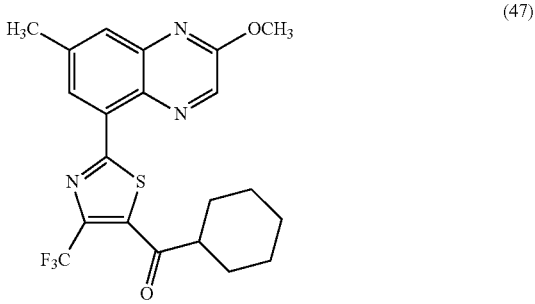 [SMILES: COc1cnc2c(-c3nc(C(F)(F)F)c(C(=O)C4CCCCC4)s3)cc(C)cc2n1]

(47)

Intermediate I-12 (20 mg, 0.086 mmol), magnesium chloride (8.16 mg, 0.086 mmol), and NBS (15.26 mg, 0.086 mmol) were dissolved in dioxane (857 µl) and heated to 70° C. for 2 hours. 2-methoxy-7-methylquinoxaline-5-carbothioamide (20 mg, 0.086 mmol) was added and the reaction mixture was heated to 110° C. for 18 h. Reaction mixture was diluted with water and EtOAc. The layers were separated and the organic layer was washed with brine, dried with sodium sulfate, and concentrated under reduced pressure. The reaction mixture was diluted with DMF, filtered, and purified by preparative HPLC (Method D, 60% to 100% B in 10 minutes) to yield Example 47 (1.4 mg, 3.21 µmol, 3.75% yield): $^1$H NMR (500 MHz, METHANOL-d$_4$) δ 8.60 (s, 1H), 8.59 (d, J=1.9 Hz, 1H), 7.82 (dd, J=1.8, 1.0 Hz, 1H), 4.15 (s, 3H), 3.08-2.99 (m, 1H), 2.66 (s, 3H), 2.02 (dd, J=13.5, 2.5 Hz, 2H), 1.88 (dt. J=13.1, 3.5 Hz, 2H), 1.76 (dt. J=13.1, 3.4 Hz, 1H), 1.58-1.39 (m, 4H), 1.35-1.26 (m, 1H). LC-MS: method H, RT=1.59 min, MS (ESI) m/z: 436.1 (M+H)$^+$. Analytical HPLC Method B: 100% purity.

Example 48

2-(2-(methoxymethyl)-7-methylquinoxalin-5-yl)-5-(1H-pyrazol-5-yl)thiazole

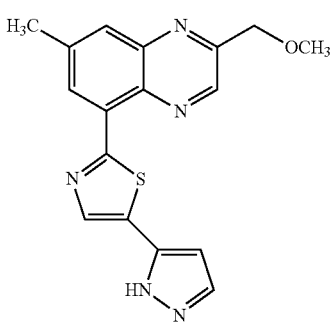

(48)

Intermediate I-13 (0.0125 g, 0.036 mmol) and (1H-pyrazol-5-yl)boronic acid (3.99 mg, 0.036 mmol) were dissolved in DMF (1 mL). PdCl$_2$(dppf)-CH$_2$Cl$_2$ adduct (1.749 mg, 2.141 µmol) was added and the reaction mixture was degassed by bubbling with argon for 15 minutes. Na$_2$CO$_3$, 3 M aqueous solution (0.050 mL, 0.150 mmol) was added and the reaction mixture was degassed for 5 minutes, then sealed and heated to 90° C. in the microwave for 30 minutes. The reaction mixture was diluted with DMF, filtered, and purified by preparative HPLC (Method D, 10% to 45% B in 10 minutes) to yield Example 48 (0.0032 g, 9.48 µmol, 26.6% yield): $^1$H NMR (500 MHz, DMSO-d$_6$) δ 9.11 (s, 1H), 8.70 (s, 1H), 8.33 (s, 1H), 7.97 (s, 1H), 7.87 (s, 1H), 6.80 (s, 1H), 4.82 (s, 2H), 3.48 (s, 3H), 2.67 (s, 3H). LC-MS: method H, RT=1.10 min, MS (ESI) m/z: 338.3 (M+H)$^+$. Analytical HPLC Method B: 100% purity.

Example 49

3-(2-(2-(methoxymethyl)-7-methylquinoxalin-5-yl)thiazol-5-yl)phenol

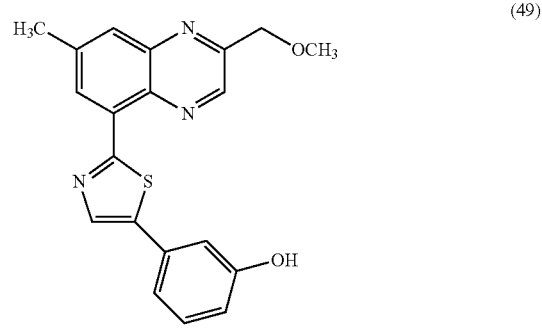 [SMILES: COCc1cnc2c(-c3ncc(-c4cccc(O)c4)s3)cc(C)cc2n1]

(49)

Intermediate I-13 (0.0125 g, 0.036 mmol) and (3-hydroxyphenyl)boronic acid (4.92 mg, 0.036 mmol) were dissolved in DMF (1 mL). PdCl$_2$(dppf)-CH$_2$Cl$_2$ adduct (1.749 mg, 2.141 µmol) was added and the reaction mixture was degassed by bubbling with argon for 15 minutes. Na$_2$CO$_3$, 3 M aqueous solution (0.050 mL, 0.150 mmol) was added and the reaction mixture was degassed for 5 minutes, then sealed and heated to 90° C. in the microwave for 30 minutes. The reaction mixture was diluted with DMF, filtered, and purified by preparative HPLC (Method D, 15% to 50% B in 20 minutes) to yield Example 49 (0.00565 g, 0.016 mmol, 43.6% yield): $^1$H NMR (500 MHz, DMSO-d$_6$) 9.72 (br. s., 1H), 9.10 (s, 1H), 8.69 (s, 1H), 8.36 (s, 1H), 7.98 (s, 1H), 7.32-7.28 (m, 1H), 7.25-7.22 (m, 1H), 7.17 (s, 1H), 6.81 (dd, J=8.0, 1.1 Hz, 1H), 4.82 (s, 2H), 3.48 (s, 3H), 2.67 (s, 3H). LC-MS: method H, RT=1.20 min, MS (ESI) m/z: 364.3 (M+H)$^+$. Analytical HPLC Method B: 100% purity.

Example 50

4-fluoro-2-(2-(2-(methoxymethyl)-7-methylquinoxalin-5-yl)thiazol-5-yl)phenol

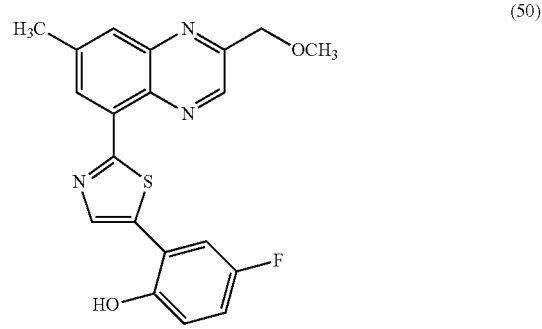 [SMILES: COCc1cnc2c(-c3ncc(-c4cc(F)ccc4O)s3)cc(C)cc2n1]

(50)

Intermediate I-13 (0.0125 g, 0.036 mmol) and (5-fluoro-2-hydroxyphenyl)boronic acid (5.56 mg, 0.036 mmol) were dissolved in DMF (1 mL). PdCl$_2$(dppf)-CH$_2$Cl$_2$ adduct (1.749 mg, 2.141 µmol) was added and the reaction mixture was degassed by bubbling with argon for 15 minutes. Na$_2$CO$_3$, 3 M aqueous solution (0.050 mL, 0.150 mmol) was added and the reaction mixture was degassed for 5 minutes, then sealed and heated to 90° C. in the microwave for 30 minutes. The reaction mixture was diluted with DMF, filtered, and purified by preparative HPLC (Method D, 35% to 75% B in 10 minutes) to yield Example 50 (0.0031 g, 8.13 µmol, 22.77% yield): $^1$H NMR (500 MHz, DMSO-d) δ 10.57 (br. s., 1H), 9.10 (s, 1H), 8.71 (s, 1H), 8.59 (s, 1H), 7.97 (s, 1H), 7.70 (dd, J=9.9, 2.8 Hz, 1H), 7.10-7.04 (m, 1H), 7.04-6.99 (m, 1H), 4.81 (s, 2H), 3.47 (s, 3H), 2.67 (s, 3H). LC-MS method H, RT=1.21 min. MS (ESI) m/z: 382.3 (M+H)$^+$. Analytical HPLC Method B: 100% purity.

Example 51

3-(2-(2-(difluoromethoxy)-7-methylquinoxalin-5-yl)thiazol-5-yl)phenol

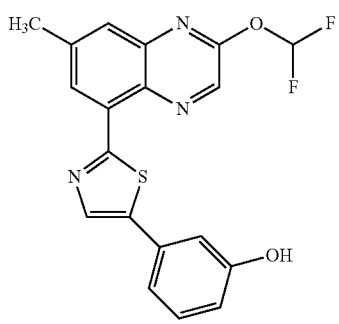

(51)

Intermediate I-10 (0.025 g, 0.067 mmol) and (3-hydroxyphenyl)boronic acid (9.26 mg, 0.067 mmol) were dissolved in DMF (3 mL). PdCl$_2$(dppf)-CH$_2$Cl$_2$ adduct (3.29 mg, 4.03 µmol) was added and the reaction mixture was degassed by bubbling with argon for 15 minutes. 3 M Na$_2$CO$_3$, 3 M aqueous solution (0.3 mL, 0.900 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was purified on Prep HPLC using Method A to yield Example 51 (0.014 g, 0.035 mmol, 51.4% yield) as a yellow solid: $^1$H NMR (400 MHz, CHLOROFORM-d) δ 8.68 (s, 1H), 8.65 (s, 1H), 8.15 (s, 1H), 7.75 (s, 1H), 7.85-7.50 (m, 1H), 7.33-7.30 (m, 2H), 7.19 (br. s., 1H), 6.85-6.81 (m, 1H), 2.66 (s, 3H). LC-MS: method H, RT=1.11 min, MS (ESI) m/z: 386.0 (M+H)$^+$. Analytical HPLC: Method A: 95.8% purity.

Example 52

2-(2-methoxy-7-methylquinoxalin-5-yl)-5-(5-methoxypyridin-2-yl)thiazole

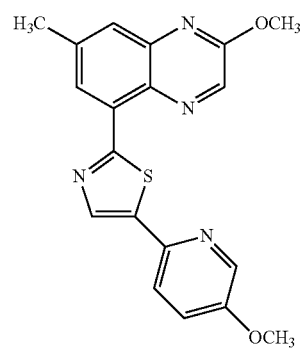

(52)

Intermediate 52A:
5-(5-methoxypyridin-2-yl)thiazole

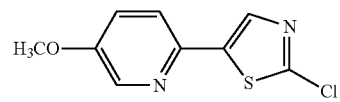

(52A)

A solution of 5-(tributylstannyl)thiazole (295 mg, 0.788 mmol) and 2-chloro-5-methoxypyridine (75 mg, 0.526 mmol) in toluene (2.0 mL) was degassed with argon for 3 min. Pd(PPh$_3$)$_4$ (24.29 mg, 0.021 mmol) was added. The reaction mixture was sealed and heated in an oil bath at 105° C. for 4 h. After being cooled to room temperature, the reaction mixture was directly loaded on a column for purification. The crude product was purified by flash chromatography (loading in chloroform, 0% to 85% EtOAc in hexane over 10 min using a 4 g silica gel cartridge). The desired fractions were combined and concentrated to yield Intermediate 52A (70 mg, 0.364 mmol, 69.3% yield) as a white solid. $^1$H NMR (400 MHz, METHANOL-d$_4$) δ 8.94 (s, 1H), 8.26 (s, 1H), 8.19 (d, J=2.9 Hz, 1H), 7.75 (d, J=8.6 Hz, 1H), 7.36 (did, J=8.7, 3.0 Hz, 1H), 3.88 (s, 3H); LC-MS: method C, RT=0.64 min, MS (ESI) m/z: 193.3 (M+H)$^+$.

Intermediate 52B:
2-chloro-5-(5-methoxypyridin-2-yl)thiazole (52B)

To diisopropylamine (0.062 mL, 0.437 mmol) in THF (2.0 mL) at −78° C. was added 1.6 N n-BuLi in hexanes (0.273 mL, 0.437 mmol). The mixture was stirred at −78° C. for 20 min. A solution of Intermediate 52A (70 mg, 0.364 mmol) in THF (1.0 mL) was added. The mixture was stirred at −78° C. for 20 min, followed by addition of perchloroethane (103 mg, 0.437 mmol) in THF (1.0 mL). The reaction mixture was stirred at −78° C. for 45 min. And at room temperature overnight, at which time LCMS indicate a completion of reaction. The reaction mixture was diluted with EtOAc, washed with 0.2 N HCl, saturated sodium bicarbonate, brine and dried over sodium sulfate. The crude product was purified by flash chromatography (loading in chloroform, 0% to 50% EtOAc in hexane over 10 min using a 4 g silica gel cartridge). The desired fractions were combined and concentrated to yield Intermediate 52B (43 mg, 0.190 mmol, 52.1% yield) as a white solid. $^1$H NMR (400 MHz, CHLOROFORM-d) δ 8.24 (dd, J=2.9, 0.4 Hz, 1H), 7.80 (s, 1H), 7.54 (dd, J=8.6, 0.7 Hz, 1H), 7.22 (dd, J=8.6, 2.9 Hz, 1H), 3.88 (s, 3H); LC-MS: method C. RT=0.89 min, MS (ESI) m/z: 227.3 and 227.5 (M+H)$^+$.

Example 52

To Intermediate I-9 (21.16 mg, 0.097 mmol), Intermediate 52B (20 mg, 0.088 mmol) and PdCl$_2$(dppf)-CH$_2$Cl$_2$ adduct (1:1) (3.60 mg, 4.41 μmol) was added toluene (1.8 mL) and EtOH (0.6 mL). The mixture was sonicated for 1 min, and flushed with Argon. To this was added sodium carbonate (2M, 0.088 mL, 0.176 mmol). The reaction mixture was heated in a microwave reactor at 135° C. for 45 min, at which time LCMS indicated a completion of reaction. The reaction mixture was diluted with EtOAc and brine. The organic layer was collected, dried over sodium sulfate and concentrated. The crude was dissolved in DMSO and purified via preparative LC/MS (method C, 50-80% B over 20 minutes, then a 7-minute hold at 100% B). Fractions containing the desired product were combined and dried via centrifugal evaporation to yield Example 52 (11.0 mg). $^1$H NMR (500 MHz, DMSO-d$_6$) δ 9.11 (s, 1H), 8.68 (s, 1H), 8.42 (s, 1H), 8.28 (d, J=6.7 Hz, 1H), 7.96 (d, J=8.2 Hz, 1H), 7.74 (s, 1H), 7.48 (d, J=8.5 Hz, 1H), 4.04 (s, 3H), 3.86 (s, 3H), 2.57 (s, 3H); LC-MS: method H, RT=2.15 min, MS (ESI) m/z: 365.1 (M+H)$^+$.

Analytical HPLC purity (method B): 80%.

Example 53

2-(2-(methoxymethyl)-7-methylquinoxalin-5-yl)-5-(5-methoxypyridin-2-yl)thiazole

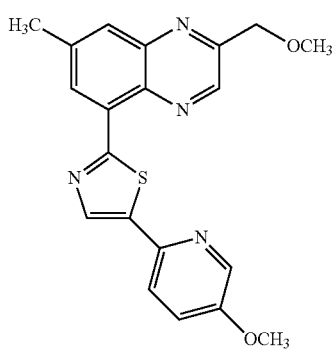

(53)

To Intermediate I-2 (22.52 mg, 0.097 mmol), Intermediate 52B (20 mg, 0.088 mmol) and PdCl$_2$(dppf)-CH$_2$Cl$_2$ adduct (1:1) (3.60 mg, 4.41 μmol) was added toluene (1.8 mL) and EtOH (0.6 mL). The mixture was sonicated for 1 min, and flushed with Argon. To this was added sodium carbonate (2M, 0.088 mL, 0.176 mmol). The reaction mixture was heated in a microwave reactor at 135° C. for 45 min. at which time LCMS indicated a completion of reaction. The reaction mixture was diluted with EtOAc and brine. The organic layer was collected, dried over sodium sulfate and concentrated. The crude was dissolved in DMSO and purified via preparative LC/MS (method C, 30-70% B over 20 minutes, then a 7-minute hold at 100% B). Fractions containing the desired product were combined and dried via centrifugal evaporation to yield Example 53 (11.0 mg). $^1$H NMR (500 MHz, DMSO-d$_6$) δ 9.09 (s, 1H), 8.66 (s, 1H), 8.51 (s, 1H), 8.32 (d, J=2.7 Hz, 1H), 7.99 (d, J=8.8 Hz, 1H), 7.95 (s, 1H), 7.49 (dd, J=8.8, 2.7 Hz, 1H), 4.79 (s, 2H), 3.88 (s, 3H), 3.45 (s, 3H), 2.63 (s, 3H); LC-MS: method H, RT=1.89 min, MS (ESI) m/z: 379.1 (M+H)$^+$. Analytical HPLC purity (method B): 98%.

What is claimed is:

1. A compound of Formula (I):

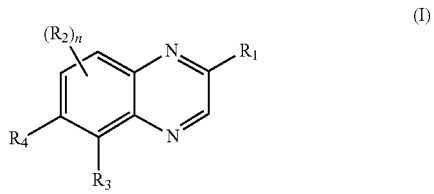

(I)

or a salt thereof; wherein:

R$_1$ is F, Cl, —OH, C$_{1-4}$ alkyl, C$_{1-4}$ fluoroalkyl, C$_{2-4}$ alkenyl, C$_{2-4}$ alkynyl, C$_{3-7}$ cycloalkyl, C$_{3-7}$ fluorocycloalkyl, C$_{1-4}$ alkoxy, C$_{1-4}$ fluoroalkoxy, C$_{2-4}$ hydroxyalkoxy, C$_{3-6}$ cycloalkoxy, (C$_{1-3}$ alkoxy)-(C$_{1-3}$ alkylene), (C$_{1-3}$ alkoxy)-(C$_{1-3}$ fluoroalkylene), (C$_{1-3}$ deuteroalkoxy)-(C$_{1-3}$ deuteroalkylene), (C$_{1-3}$ fluoroalkoxy)-(C$_{1-3}$ alkylene), (C$_{1-3}$ fluoroalkoxy)-(C$_{1-3}$ fluoroalkylene), —(CH$_2$)$_{1-3}$O(phenyl), —(CH$_2$)$_{1-3}$NR$_a$R$_a$, —C(O)O(C$_{1-6}$ alkyl), —C(O)NR$_a$R$_a$, —C(O)NR$_b$R$_b$, —NH$_2$, —NH(C$_{1-6}$ alkyl), —N(C$_{1-6}$ alkyl)$_2$, azetidin-1-yl, pyrrolidin-1-yl, furanyl, pyranyl, piperidin-1-yl, morpholin-4-yl, piperazin-1-yl, —S(O)$_2$(C$_{1-3}$ alkyl), —S(O)$_2$NR$_a$R$_a$, C$_{1-3}$ alkylthio, or C$_{1-3}$ fluoroalkylthio;

R$_2$, at each occurrence, is independently H, F, Cl, Br, —OH, —CN, C$_{1-4}$ alkyl, C$_{1-4}$ fluoroalkyl, C$_{1-4}$ hydroxyalkyl, C$_{1-3}$ aminoalkyl, C$_{2-4}$ alkenyl, C$_{2-4}$ alkynyl, C$_{3-7}$ cycloalkyl, C$_{3-7}$ fluorocycloalkyl, C$_{1-6}$ alkoxy, C$_{1-3}$ fluoroalkoxy, C$_{1-3}$ alkylthio, C$_{1-3}$ fluoroalkylthio, (C$_{1-3}$ alkoxy)-(C$_{1-3}$ alkylene), (C$_{1-3}$ fluoroalkoxy)-(C$_{1-3}$ alkylene), —C(O)NH$_2$, —C(O)NH (C$_{1-6}$ alkyl), —C(O)N(C$_{1-6}$ alkyl)$_2$, —C(O)NR$_b$R$_b$, —CH(OH)(C$_{3-6}$ cycloalkyl), —CH(OH)(phenyl), —CH(OH)(pyridyl), —S(O)$_2$(C$_{1-3}$ alkyl), —S(O)$_2$NR$_a$R$_a$, or a cyclic group selected from phenyl, 5- to 6-membered heteroaryl, and 5- to 7-membered heterocycle, wherein said cyclic group is substituted with zero to 5 substituents independently selected from F, Cl, C$_{1-3}$ alkoxy, and —CN;

R₃ is:

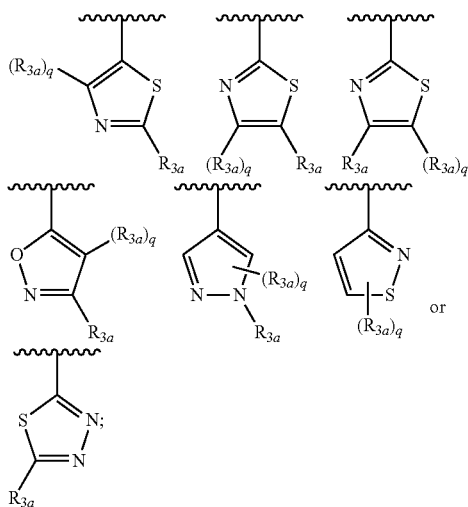

R₃ₐ, at each occurrence, is independently H, F, Cl, —CN, —OH, C₁₋₆ alkyl, C₂₋₆ alkenyl, C₁₋₆ fluoroalkyl, C₁₋₆ hydroxyalkyl, C₁₋₆ alkoxy, C₁₋₃ fluoroalkoxy, C₁₋₆ alkylthio, —(CH₂)ₘ—C₃₋₇ cycloalkyl, —(CH₂)ₘ-aryl, —(CH₂)ₘ-heteroaryl, —(CH₂)ₘ-heterocyclyl, —(CH₂)₁₋₃NRₐRₐ, —(CH₂)₁₋₃NHS(O)₂(aryl), (C₁₋₃ alkoxy)-(C₁₋₆ alkoxy), —C(O)OH, —C(O)O(C₁₋₆ alkyl), —C(O)NRₐRₐ, —C(O)NRᵦRᵦ, —S(O)₂NRₐRₐ, —S(O)₂NRᵦRᵦ, —C(O)(C₁₋₄ alkyl), —C(O)aryl, —C(O)heteroaryl, —C(O)(C₃₋₇ cycloalkyl), —S(O)₂(C₁₋₄ alkyl), —S(O)₂aryl, —S(O)₂heteroaryl, —S(O)₂ (C₃₋₇ cycloalkyl), —NRₐRₐ, or —NRᵦRᵦ, wherein each of said cycloalkyl, heterocyclyl, aryl, and heteroaryl is substituted with zero to 5 substituents independently selected from F, Cl, —OH, oxo, —CN, C₁₋₃ alkyl, C₁₋₃ fluoroalkyl, C₁₋₄ hydroxyalkyl, C₁₋₃ alkoxy, C₁₋₃ fluoroalkoxy, C₁₋₆ alkylthio, —NH₂, —NHC(O) (C₁₋₆ alkyl), C₁₋₃ hydroxyalkoxy, COOH, —C(O)O (C₁₋₆ alkyl) —C(O)NRₐRₐ, —C(O)NRᵦRᵦ, —S(O)₂NRₐRₐ, —S(O)₂NRᵦRᵦ, —C(O)(C₁₋₄ alkyl), —C(O)aryl, —C(O)heteroaryl, —C(O)(C₃₋₇ cycloalkyl), —S(O)₂(C₁₋₄ alkyl), —S(O)₂aryl, —S(O)₂heteroaryl, —S(O)₂ (C₃₋₇ cycloalkyl), —NRₐRₐ, or —NRᵦRᵦ;

R₄ is H, F, Cl, or —CH₃;

Rₐ, at each occurrence, is independently H, C₁₋₃ alkyl, C₁₋₃ fluoroalkyl, C₃₋₆ cycloalkyl, aryl, or heteroaryl;

two Rᵦ along with the nitrogen atom to which they are attached form a 4- to 7-membered heterocyclo ring;

m, at each occurrence, is zero, 1, or 2;

n, at each occurrence, is zero, 1, or 2; and q is zero or 1.

2. The compound according to claim 1 or a salt thereof; wherein:

R₁ is methyl, —OCH₃, —OCHF₂, —OCH₂CH₃, or —CH₂OCH₃;

R₂ is H, F, Cl, Br, —OH, —CN, C₁₋₃ alkyl, C₁₋₃ fluoroalkyl, C₁₋₃ hydroxyalkyl, or C₁₋₃ aminoalkyl; and R₃ₐ, at each occurrence, is independently H, —CH₃, —C(CH₃)₃, —CF₃, —CH₂OH, —CH=CH₂, cyclopropyl, cyclohexyl, —CH₂(phenyl), —C(O)(hydroxymethyl piperidinyl), —C(O)(cyclohexyl), —C(O)NHCH₂CH₃, —C(O)NH(methoxy phenyl), piperidinyl, pyrazolyl, methyl pyrazolyl, indole, phenyl substituted with zero to 3 substituents independently selected from F, Cl, —OH, —CH₃, —CHF₂, —CF₃, and —OCF₃; or pyridinyl substituted with zero to 2 substituents independently selected from —OH, —CH₃, and —OCH₃.

3. The compound according to claim 2, wherein R₁ is —OCH₃, —OCF₂, or —CH₂OCH₃;
n is zero or 1; and
q is zero or 1.

4. The compound according to claim 3 having the structure of Formula (Ia):

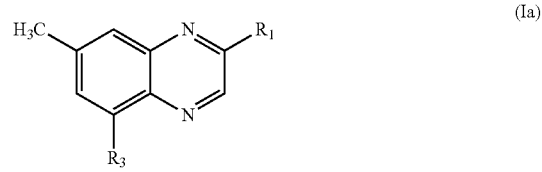

or a salt thereof.

5. The compound according to claim 4 or a salt thereof, wherein R₃ is:

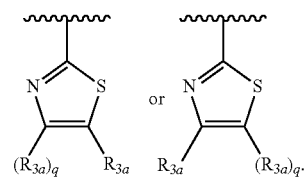

6. The compound according to claim 1 or a salt thereof, wherein said compound is selected from: 5-(2-methoxy-7-methylquinoxalin-5-yl)-3-phenylisoxazole (1); 2-(difluoromethoxy)-7-methyl-5-(1-phenyl-1H-pyrazol-4-yl)quinoxaline (2); 5-(2-(difluoromethoxy)-7-methylquinoxalin-5-yl)-2-phenylthiazole (3); 2-(2-(difluoromethoxy)-7-methylquinoxalin-5-yl)-5-methylthiazole (4); 3-(2-(difluoromethoxy)-7-methylquinoxalin-5-yl)isothiazole (5); 3-(2-(2-(difluoromethoxy)-7-methylquinoxalin-5-yl)-4-methylthiazol-5-yl)phenol (6); 5-benzyl-2-(2-(difluoromethoxy)-7-methylquinoxalin-5-yl)thiazole (7); 2-(2-(difluoromethoxy)-7-methylquinoxalin-5-yl)-4-vinylthiazole (8); 2-(2-(difluoromethoxy)-7-methylquinoxalin-5-yl)-4-methyl-5-(1H-pyrazol-5-yl)thiazole (9); 4-cyclopropyl-2-(2-(difluoromethoxy)-7-methylquinoxalin-5-yl)thiazole (10); 2-(2-(2-(difluoromethoxy)-7-methylquinoxalin-5-yl)-4-methylthiazol-5-yl)-4-fluorophenol (11); 2-(2-(2-(difluoromethoxy)-7-methylquinoxalin-5-yl)-4-methylthiazol-5-yl)-3-fluorophenol (12); 2-(2-(difluoromethoxy)-7-methylquinoxalin-5-yl)-5-(piperidin-1-yl)thiazole (13); 5-(2-(2-(difluoromethoxy)-7-methylquinoxalin-5-yl)thiazol-5-yl)pyridin-3-ol (14); 2-(2-(2-(difluoromethoxy)-7-methylquinoxalin-5-yl)-4-methylthiazol-5-yl)phenol (15); 2-(2-(difluoromethoxy)-7-methylquinoxalin-5-yl)-5-(2-(trifluoromethyl)phenyl)thiazole (16); 5-cyclohexyl-2-(2-(difluoromethoxy)-7-methylquinoxalin-5-yl)thiazole (17); 2-(2-(methoxymethyl)-7-methylquinoxalin-5-yl)-5-phenylthiazole (18); 2-(2-(2-(difluoromethoxy)-7-methylquinoxalin-5-yl)thiazol-5-yl)-6-fluorophenol (19); 2-(2-(2-(difluoromethoxy)-7-methylquinoxalin-5-yl)thiazol-5-yl)-4-methylphenol (20); 2-(2-(2-(difluoromethoxy)-

7-methylquinoxalin-5-yl)thiazol-5-yl)-4-fluorophenol (21); 2-(2-(2-(difluoromethoxy)-7-methylquinoxalin-5-yl)thiazol-5-yl)-4-chlorophenol (22); 2-(2-(2-(difluoromethoxy)-7-methylquinoxalin-5-yl)thiazol-5-yl)-6-chlorophenol (23); 2-(2-(2-(difluoromethoxy)-7-methylquinoxalin-5-yl)thiazol-5-yl)-3-fluorophenol (24); 3-(2-(2-(difluoromethoxy)-7-methylquinoxalin-5-yl)thiazol-5-yl)-4-fluorophenol (25); 3-(2-(2-(difluoromethoxy)-7-methylquinoxalin-5-yl)thiazol-5-yl)-5-fluorophenol (26); 3-(2-(2-(difluoromethoxy)-7-methylquinoxalin-5-yl)thiazol-5-yl)-4-(trifluoromethoxy)phenol (27); 2-(2-(difluoromethoxy)-7-methylquinoxalin-5-yl)-5-phenylthiazole (28); 2-(2-(difluoromethoxy)-7-methylquinoxalin-5-yl)-5-(pyridin-3-yl)thiazole (29); 2-(2-(2-(difluoromethoxy)-7-methylquinoxalin-5-yl)thiazol-5-yl)phenol (30); N-ethyl-2-(2-methoxy-7-methylquinoxalin-5-yl)thiazole-5-carboxamide (31); 2-(2-(difluoromethoxy)-7-methylquinoxalin-5-yl)-N-(4-methoxyphenyl)thiazole-4-carboxamide (32); (2-(2-(difluoromethoxy)-7-methylquinoxalin-5-yl)thiazol-4-yl)(4-(hydroxymethyl)piperidin-1-yl)methanone (33); 2-(2-(difluoromethoxy)-7-methylquinoxalin-5-yl)thiazole (34); 2-(2-(difluoromethoxy)-7-methylquinoxalin-5-yl)-5-phenyl-1,3,4-thiadiazole (35); 2-(2-(difluoromethoxy)-7-methylquinoxalin-5-yl)-4-methylthiazole (36); 2-(2-(difluoromethoxy)-7-methylquinoxalin-5-yl)-5-(1H-indol-7-yl)thiazole (37); 2-(2-(difluoromethoxy)-7-methylquinoxalin-5-yl)-5-(1H-indol-4-yl)thiazole (38); (2-(2-(difluoromethoxy)-7-methylquinoxalin-5-yl)thiazol-5-yl)methanol (39); 2-(2-(difluoromethoxy)-7-methylquinoxalin-5-yl)-5-(1H-pyrazol-5-yl)thiazole (40); 4-(tert-butyl)-2-(2-(difluoromethoxy)-7-methylquinoxalin-5-yl)thiazole (41); 2-(2-(difluoromethoxy)-7-methylquinoxalin-5-yl)-5-(1H-indol-6-yl)thiazole (42); 2-(2-(difluoromethoxy)-7-methylquinoxalin-5-yl)-5-(pyridin-4-yl)thiazole (43); 2-(2-(difluoromethoxy)-7-methylquinoxalin-5-yl)-5-(pyridin-2-yl)thiazole (44); 5-(2-(difluoromethyl)phenyl)-2-(2-methoxy-7-methylquinoxalin-5-yl)thiazole (45); 2,3-difluoro-5-(2-(2-methoxy-7-methylquinoxalin-5-yl)thiazol-5-yl)phenol (46); cyclohexyl(2-(2-methoxy-7-methylquinoxalin-5-yl)-4-(trifluoromethyl)thiazol-5-yl)methanone (47); 2-(2-(methoxymethyl)-7-methylquinoxalin-5-yl)-5-(1H-pyrazol-5-yl)thiazole (48); 3-(2-(2-(methoxymethyl)-7-methylquinoxalin-5-yl)thiazol-5-yl)phenol (49); 4-fluoro-2-(2-(2-(methoxymethyl)-7-methylquinoxalin-5-yl)thiazol-5-yl)phenol (50); 3-(2-(2-(difluoromethoxy)-7-methylquinoxalin-5-yl)thiazol-5-yl)phenol (51); 2-(2-methoxy-7-methylquinoxalin-5-yl)-5-(5-methoxypyridin-2-yl)thiazole (52); and 2-(2-(methoxymethyl)-7-methylquinoxalin-5-yl)-5-(5-methoxypyridin-2-yl)thiazole (53).

7. A pharmaceutical composition, which comprises a pharmaceutically acceptable carrier and a compound according to claim 1 or a pharmaceutically acceptable salt thereof, alone or in combination with another therapeutic agent.

8. A method for the treatment of a thromboembolic disorder or the primary prophylaxis of a thromboembolic disorder, which comprises the steps of administering to a patient in need thereof a therapeutically effective amount of a compound according to claim 1 or a pharmaceutically acceptable salt thereof, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

9. The method according to claim 8 wherein the thromboembolic disorder is selected from the group consisting of unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, and procedures in which blood is exposed to an artificial surface that promotes thrombosis.

10. A method of inhibiting or preventing platelet aggregation, which comprises the step of administering to a subject in need thereof a therapeutically effective amount of a compound according to claim 1 or a salt thereof.

* * * * *

UNITED STATES PATENT AND TRADEMARK OFFICE
CERTIFICATE OF CORRECTION

PATENT NO. : 10,815,224 B2
APPLICATION NO. : 16/317232
DATED : October 27, 2020
INVENTOR(S) : Jeremy Richter et al.

Page 1 of 1

It is certified that error appears in the above-identified patent and that said Letters Patent is hereby corrected as shown below:

In the Claims

In Column 91, Line 44, Claim 1, after "($C_{1-6}$ alkyl)" insert -- , --.

In Column 92, Line 9, Claim 3, delete "—$OCF_2$," and insert -- —$OCHF_2$, --, therefor.

In Column 92, Line 10 (Approx.), Claim 3, above "11 is zero or 1; and" insert -- $R_4$ is H; --.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*